United States Patent [19]

Maduskuie, Jr. et al.

[11] Patent Number: 5,942,544

[45] Date of Patent: Aug. 24, 1999

[54] α-BRANCHED ANILINES, TOLUENES, AND ANALOGS THEREOF AS FACTOR XA INHIBITORS

[75] Inventors: Thomas Peter Maduskuie, Jr., Wilmington; Joseph Cacciola, Newark, both of Del.; John Matthew Fevig, Lincoln University, Pa.; Mimi Lifen Quan, Newark; Petrus Fredericus Wilhelmus Stouten, Wilmington, both of Del.

[73] Assignee: DuPont Pharmaceuticals Company, Wilmington, Del.

[21] Appl. No.: 08/801,220

[22] Filed: Feb. 19, 1997

Related U.S. Application Data

[60] Provisional application No. 60/012,104, Feb. 22, 1996, provisional application No. 60/091,788, Feb. 3, 1997, and provisional application No. 60/036,823, Feb. 3, 1997.

[51] Int. Cl.[6] ............... A61K 31/215; A61K 31/195; A61K 31/23; C07C 229/14; C07C 211/00; C07C 213/02

[52] U.S. Cl. ............... 514/539; 514/416; 514/535; 514/561; 514/568; 514/647; 514/649; 546/334; 546/336; 548/494; 548/504; 560/34; 560/35; 560/55; 562/426; 562/429; 562/430; 562/433; 564/149; 564/162; 564/164; 564/336

[58] Field of Search ............... 514/357, 419, 514/478, 539, 588, 631, 634, 647, 649, 416, 535, 561, 568, 637; 546/334, 336; 548/494, 504; 564/48, 161, 230, 307, 147, 149, 162, 164, 336; 560/34, 35, 55; 562/426, 429, 430, 433

[56] References Cited

U.S. PATENT DOCUMENTS 5,187,157 2/1993 Kettner et al. ............... 514/18
5,492,895 2/1996 Vlasuk et al. ............... 514/18

FOREIGN PATENT DOCUMENTS

| 2 054 850 | 5/1992 | Canada . |
|---|---|---|
| 2 073 776 | 5/1992 | Canada . |
| 4 45 796 | 9/1991 | European Pat. Off. . |
| 5 13 810 | 11/1992 | European Pat. Off. . |
| 5 607 30 | 9/1993 | European Pat. Off. . |
| 4 421 052 | 12/1995 | Germany . |
| 5-078344 | 3/1993 | Japan . |
| 7-330695 | 12/1995 | Japan . |
| 9 30 733 | 5/1993 | South Africa . |
| 9 21 5607 | 9/1992 | WIPO . |
| 9 30 7867 | 4/1993 | WIPO . |
| 9 308 164 | 4/1993 | WIPO . |
| 9 316 036 | 8/1993 | WIPO . |
| 9 633 970 | 10/1996 | WIPO . |

OTHER PUBLICATIONS

Tidwell et al., *Thrombosis Research* 1980, 19, 339–349, "Strategies for Anticoagulation with Synthetic Protease Inhibitors. Xa Inhibitors Versus Thrombin Inhibitors".

*Primary Examiner*—Yogendra N. Gupta
*Attorney, Agent, or Firm*—David H. Vance

[57] ABSTRACT

The present application describes m-amidino phenyl analogs of formula I:

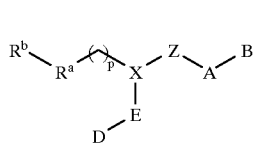

I wherein D can be amidino and E can be phenyl, which are useful as inhibitors of factor Xa.

18 Claims, No Drawings

α-BRANCHED ANILINES, TOLUENES, AND ANALOGS THEREOF AS FACTOR XA INHIBITORS

This application claims benefit of Provisional Applications Ser. No. 60/012,104, filed Feb. 22, 1996, Ser. No. 60/091,788 filed Feb. 3, 1997, Ser. No. 60/036,823 Feb. 3, 1997.

FIELD OF THE INVENTION

This invention relates generally to m-amidino phenyl analogs which are inhibitors of factor Xa, pharmaceutical compositions containing the same, and methods of using the same as anticoagulant agents for treatment and prevention of thromboembolic disorders.

BACKGROUND OF THE INVENTION

Activated factor Xa, whose major practical role is the generation of thrombin by the limited proteolysis of prothrombin, holds a central position that links the intrinsic and extrinsic activation mechanisms in the final common pathway of blood coagulation. The generation of thrombin, the final serine protease in the pathway to generate a fibrin clot, from its precursor, is amplified by formation of prothrombinase complex (factor Xa, factor V, $Ca^{2+}$ and phospholipid). Since it is calculated that one molecule of factor Xa can generate 138 molecules of thrombin (Elodi, S., Varadi, K.: *Optimization of conditions for the catalytic effect of the factor IXa-factor VIII Complex: Probable role of the complex in the amplification of blood coagulation. Thromb. Res.* 1979, 15, 617–629), inhibition of factor Xa may be more efficient than inactivation of thrombin in interrupting the blood coagulation system.

Stuerzebecher et al, *Thrombosis Research* 1976, 9, 637–646, report comparative studies of a number of benzamidine derivatives as factor Xa inhibitors. The most active inhibitors were 3-amidino-phenylaryl derivatives. In *Thrombosis Research* 1980, 17, 545–548, Stuerzebecher et al detail factor Xa inhibitory activity of a series of a,a'-bis-(4-amidinobenzyl)cycloalkanones, a,a'-bis-(4-aminobenzylidene)- and a,a'-bis-(3-aminobenzylidene) cycloalkanones with 5 to 8-membered rings, the corresponding non-cyclic derivatives, and derivatives containing only one amidino group.

Tidwell et al, *Thrombosis Research* 1980, 19, 339–349, describe factor Xa inhibitory activity of a series of aromatic mono- and di-amidines. The amidino aromatic moieties are either bicyclic heterocycles or amidino-phenoxy groups.

Hauptmann et al, *Blood Coagulation and Fibrinolysis* 1993, 4, 577–582, and *Thromb. Haemostasis* 1990, 63(2), 220–223, address testing of several synthetic compounds as factor Xa inhibitors: Na-tosylglycyl-3-amidinophenylalanine methyl ester; 2,7-bis(4-amidinobenzylidene)-cycloheptanone-(1); Na-tosyl-4-amidinophenylalanine piperidide; Na-naphthylsulphonylglycyl-4-amidinophenylalanine piperidide; 4-methyl-1-$N^2$-(methyl-1,2,3,4-tethydro-8-quinolinesulphonyl-L-arginyl-2-piperidine carbonic acid; and D-phenylalanyl-L-propyl-L-arginine chloromethyl ketone.

Nagahara et al, EP 0,540,051 A1 and *J. Med. Chem.* 1994, 37, 1200–1207 and Hara et al, *Thromb. Haemostas* 1994, 71(3), 314–319, discuss amidino aromatic bicycles which have factor Xa inhibitory activity. Examples include amidino naphthylenes, amidino-indoles, amidino-benzimidazoles, and amidino-benzothiophenes. Amidino phenyl derivatives are not addressed. JP 05078344, another publication in the above-noted family, describes symmetrical factor Xa inhibitors containing terminal amidino aromatic bicycles.

Bovy et al, WO 93/08164, report substituted heterocyclic derivatives of the formula:

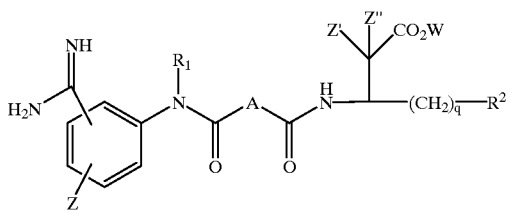

which are useful as platelet aggregation modulators or inhibitors. No mention is made of using the above compounds as factor Xa inhibitors.

Himmelsbach et al in CA 2,054,850 discuss aggregation inhibiting compounds of the formula:

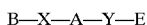

wherein A may be a cyclic imino such as pyrrolidine and amidst the various definitions of B and X one can find groups such as amidino and arylene. The combination of A—Y—E, however, is not considered to be useful for the present invention. Thus, the compounds of Himmelsbach et al differ from those of the present invention. Moreover, inhibition of factor Xa is not discussed in Himmelsbach et al as a use for the compounds of the above formula.

Despite the foregoing, more efficacious and specific inhibitors of factor Xa are needed as potentially valuable therapeutic agents for the treatment of thromboembolic disorders. Thus, it is desirable to discover new factor Xa inhibitors.

SUMMARY OF THE INVENTION

Accordingly, one object of the present invention is to provide novel amidino-phenyl factor Xa inhibitors.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention is to provide a method for treating thromboembolic disorders comprising administering to a host in need of such treatment a therapeutically effective amount of at least one of the compounds of the present invention or a pharmaceutically acceptable salt or prodrug form thereof.

These and other objects, which will become apparent during the following detailed description, have been achieved by the inventors' discovery that compounds of formula (I):

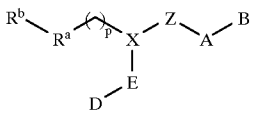

or a pharmaceutically acceptable salt or prodrug forms thereof, wherein A, B, D, E, $R^a$, $R^b$, X, Z and p are defined below, are effective factor Xa inhibitors.

DETAILED DESCRIPTION OF PREFERRED EMBODIMENTS

[1] Thus, in a first embodiment, the present invention provides novel compounds of formula I:

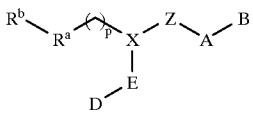

or stereoisomers or pharmaceutically acceptable salt forms thereof, wherein:

D is selected from CN, $C(=NR^7)NR^8R^9$, $NHC(=NR^7)NR^8R^9$, $NR^8CH(=NR^7)$, $C(O)NR^8R^9$, and $(CH_2)_tNR^8R^9$, provided that D is substituted meta or para to G on E;

E is selected from phenyl, 2-pyridyl, 4-pyridyl, pyrimidyl, and piperidinyl substituted with 1 $R^2$;

$R^a$ is a bond or $CH=CH$;

$R^b$ is $C(O)R$ or G

G is selected from H, $OG^1$, $SG^1$, $NG^1G^2$, $OC(O)NG^2G^3$, $C_{3-10}$ carbocyclic residue substituted with 0–2 $R^4$, and a 5–10 membered heterocyclic system containing from 1–3 heteroatoms selected from the group consisting of N, O, and S substituted with 0–2 $R^4$;

$G^1$ is selected from H, $C_{1-6}$ alkyl, $C_{3-10}$ carbocyclic residue substituted with 0–2 $R^4$, and a 5–10 membered heterocyclic system containing from 1–3 heteroatoms selected from the group consisting of N, O, and S substituted with 0–2 $R^4$ provided that if $Y^1$ is a heterocyclic system, then it is not attached to Y through one of the heteroatoms of the heterocyclic system;

$G^2$ is selected from H and $C_{1-6}$ alkyl;

$G^3$ is selected from $C_{3-10}$ carbocyclic residue substituted with 0–2 $R^4$ and a 5–10 membered heterocyclic system containing from 1–3 heteroatoms selected from the group consisting of N, O, and S substituted with 0–2 $R^4$;

R is selected from H, OH, $C_{1-6}$ alkoxy, $C_{3-6}$ cycloalkoxy, $C_{6-10}$ aryloxy substituted with 0–2 $R^4$, $C_{1-6}$ alkyl substituted with 0–2 $R^5$, $NH_2$, $NR^1R^{1a}$, and $C_{3-10}$ carbocyclic residue substituted with 0–2 $R^4$;

$R^1$ and $R^{1a}$ are independently selected from H, $C_{1-6}$ alkoxy, $C_{1-6}$ alkyl substituted with 0–2 $R^5$, and $C_{3-10}$ carbocyclic residue substituted with 0–2 $R^4$;

$R^1$ and $R^{1a}$ together can be $C_{3-5}$ alkylene substituted with 0–2 $R^3$;

$R^2$ is selected from H, $OR^1$, halo, $C_{1-6}$ alkyl, $NR^1R^{1a}$, $C(=O)R^6$, and $SO_2NR^1R^{1a}$;

$R^3$ is selected from CN, $NO_2$, $C_{1-6}$ alkoxy, OH, $C_{1-6}$ alkyl, phenyl and halo;

$R^4$ is selected from H, OH, $C_{1-6}$ alkoxy, halo, $C_{1-6}$ alkyl, $C_{1-2}$ haloalkyl, CN, $NO_2$, $NR^6R^{6a}$, $(CH_2)_nNR^6R^{6a}$, $SO_2-C_{1-6}$ alkyl, $C(=O)R^6$, $SO_2-C_{6-10}$ aryl, $N(R^6)SO_2-C_{1-6}$ alkyl, and $SO_2NR^6R^{6a}$;

$R^5$ is selected from H, OH, $C_{1-6}$ alkoxy, phenyl, halo, $C_{1-6}$ alkyl, $C_{1-2}$ haloalkyl, CN, $NO_2$, $NR^6R^{6a}$, $(CH_2)_nNR^6R^{6a}$, $C(=O)R^6$, and $SO_2NR^6R^{6a}$;

$R^6$ and $R^{6a}$ are independently selected from H, $C_{1-6}$ alkyl, OH, $C_{1-6}$ alkoxy, $C_{3-6}$ cycloalkoxy, $C_{6-10}$ aryloxy;

$R^6$ and $R^{6a}$ together can be $C_{3-5}$ alkylene substituted with 0–2 $R^3$;

$R^7$ is selected from H, OH, $C_{1-6}$ alkyl, $C_{1-6}$ alkylcarbonyl, $C_{1-6}$ alkoxy, $C_{1-4}$ alkoxycarbonyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^8$ is selected from H, $C_{1-6}$ alkyl and $(CH_2)_n$-phenyl;

$R^9$ is selected from H, $C_{1-6}$ alkyl and $(CH_2)_n$-phenyl;

X is selected from $CHCH(R^1)$, $CHN(R^1)$, $CH-O$, $CR^1$, N, and $NCH(R^1)$;

Z is selected from $(CH_2)_n$, $C(=O)$, $C(=O)(CH_2)_n$ and $C(=O)N(R^1)$;

X and Z together can be selected from $C(R^1)(CH_2)_qS(O)_m(CH_2)_q$, $C(R^1)N(CH_2)_qS(O)_m(CH_2)_q$, $C(R^1)(CH_2)_qS(O)_mN(R^6)(CH_2)_q$, $C(R^1)N(CH_2)_qS(O)_mN(R^6)(CH_2)_q$, $N(CH_2)_qS(O)_m(CH_2)_q$, and $N(CH_2)_qS(O)_mN(R^6)(CH_2)_q$, m is 0, 1, or 2;

n is 1, 2, 3 or 4;

p is 1, 2, 3, or 4;

q is 0, 1, or 2;

t is selected from 0 and 1;

A is selected from:

benzyl substituted with 0–2 $R^4$;

$C_{3-10}$ carbocyclic residue substituted with 0–2 $R^4$; and, a 5–10 membered heterocyclic system containing from 1–3 heteroatoms selected from the group consisting of N, O, and S substituted with 0–2 $R^4$; and, B is selected from H, $NR^1R^4$, $C(O)R^6$, $C(O)NR^6R^{6a}$, $C_{1-6}$ alkyl, $C(=NR^1)NR^1R^{1a}$, $NR^1C(=NR^1)NR^1R^{1a}$, $B^1-B^2$ benzyl substituted with 0–2 $R^4$, $C_{3-10}$ carbocyclic residue substituted with 0–2 $R^4$, and 5–10 membered heterocyclic system containing from 1–3 heteroatoms selected from the group consisting of N, O, and S substituted with 0–2 $R^4$;

$B^1$ is selected from $C_{1-4}$ alkylene, $-C(O)-$, $-C(O)CR^{10}R^{10a}-$, $-CR^{10}R^{10a}C(O)$, $-S(O)_q-$, $-S(O)_qCR^{10}R^{10a}-$, $-CR^{10}R^{10a}S(O)_q-$, $-S(O)_2NR^{10}-$, $-NR^{10}S(O)_2-$, $-NR^{10}S(O)_2CR^{10}R^{10a}-$, $-CR^{10}R^{10a}S(O)_2NR^{10}-$, $-NR^{10}S(O)_2NR^{10}-$, $-C(O)NR^{10}-$, $-NR^{10}C(O)-$, $-C(O)NR^{10}CR^{10}R^{10a}-$, $-NR^{10}C(O)CR^{10}R^{10a}-$, $-CR^{10}R^{10a}C(O)NR^{10}-$, $-CR^{10}R^{10a}NR^{10}C(O)-$, $-NR^{10}C(O)O-$, $-OC(O)NR^{10}-$, $-NR^{10}C(O)NR^{10}-$, $-NR^{10}-$, $-NR^{10}CR^{10}R^{10a}-$, $-CR^{10}R^{10a}NR^{10}-$, O, $-CR^{10}R^{10a}O-$, and $-OCR^{10}R^{10a}-$;

$B^2$ is selected from:

$C_{3-10}$ carbocyclic residue substituted with 0–2 $R^4$, and

5–10 membered heterocyclic system containing from 1–4 heteroatoms selected from the group consisting of N, O, and S substituted with 0–2 $R^4$;

$R^{10}$ is selected from H, $CF_3$, $C_{1-6}$ alkyl, $C_{3-6}$ carbocyclic residue substituted with 0–2 $R^4$, and 5–6 membered heterocyclic system containing from 1–4 heteroatoms selected from the group consisting of N, O, and S substituted with 0–2 $R^4$; and, $R^{10a}$ is selected from H, $CF_3$, $C_{1-6}$ alkyl, $C_{3-6}$ carbocyclic residue substituted with 0–2 $R^4$, and 5–6 membered heterocyclic system containing from 1–4 heteroatoms selected from the group consisting of N, O, and S substituted with 0–2 $R^4$;

provided that when:

(a) D is C(=NH)NH$_2$, $R^a$ is a bond, p=1, X and Z together are CH(CH$_2$)$_2$, A is phenyl, and B is para-C(=NH)NH$_2$, R is not OH;

(b) D is C(=NH)NH$_2$, p=1, $R^a$ is a bond, X is CH—O, Z is CH$_2$, A is phenyl, and B is H, R is not OH; and, (c) when one of A or B is a non-aromatic heterocycle containing a nitrogen as the only heteroatom, the group $R^b$—$R^a$— is other than H or aryl.

[2] In a preferred embodiment, the present invention novel compounds of formula I, wherein;

G is selected from H, OG$^1$, SG$^1$, NG$^1$G$^2$, OC(O)NG$^2$G$^3$, C$_{5-6}$ carbocyclic residue substituted with 0–2 $R^4$, and a 5–6 membered heterocyclic system containing from 1–3 heteroatoms selected from the group consisting of N, O, and S substituted with 0–2 $R^4$;

G$^1$ is selected from H, C$_{1-6}$ alkyl, C$_{5-6}$ carbocyclic residue substituted with 0–2 $R^4$, and a 5–6 membered heterocyclic system containing from 1–3 heteroatoms selected from the group consisting of N, O, and S substituted with 0–2 $R^4$ provided that if $Y^1$ is a heterocyclic system, then it is not attached to Y through one of the heteroatoms of the heterocyclic system;

G$^3$ is selected from C$_{5-6}$ carbocyclic residue substituted with 0–2 $R^4$ and a 5–6 membered heterocyclic system containing from 1–3 heteroatoms selected from the group consisting of N, O, and S substituted with 0–2 $R^4$;

B is selected from B$^2$, B$^1$-B$^2$, NR$^1$R$^4$, C(O)R$^6$, C(O)NR$^6$R$^{6a}$, C$_{1-6}$ alkyl, C(=NR$^1$)NR$^1$R$^{1a}$, and NR$^1$C(=NR$^1$)NR$^1$R$^{1a}$;

B$^1$ is selected from C$_{1-4}$ alkylene, —C(O)—, —C(O)CR$^{10}$R$^{10a}$—, —CR$^{10}$R$^{10a}$C(O), —S(O)$_q$—, —S(O)$_q$CR$^{10}$R$^{10a}$—, —CR$^{10}$R$^{10a}$S(O)$_q$—, —S(O)$_2$NR$^{10}$—, —NR$^{10}$S(O)$_2$—, —C(O)NR$^{10}$—, —NR$^{10}$C(O)—, —NR$^{10}$—, —NR$^{10}$CR$^{10}$R$^{10a}$—, —CR$^{10}$R$^{10a}$NR$^{10}$—, O, —CR$^{10}$R$^{10a}$O—, and —OCR$^{10}$R$^{10a}$—;

B$^2$ is selected from one of the following carbocyclic and heterocyclic systems which are substituted with 0–2 $R^{4a}$;

phenyl, piperidinyl, piperazinyl, pyridyl, pyrimidyl, furanyl, thiophenyl, pyrrolyl, oxazolyl, isoxazolyl, thiazolyl, isothiazolyl, pyrazolyl, imidazolyl, oxadiazole, thiadiazole, triazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2,3-triazole, 1,2,4-triazole, 1,2,5-triazole, 1,3,4-triazole, benzofuran, benzothiofuran, indole, benzoxazole, benzthiazole, indazole, benzisoxazole, benzisothiazole, and isoindazole;

B$^2$ may also be selected from the following bicyclic heteroaryl ring systems:

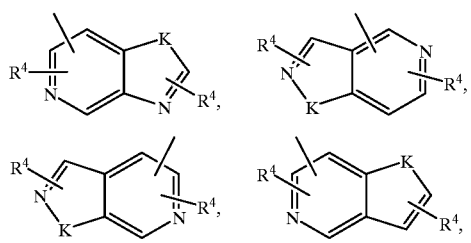

-continued

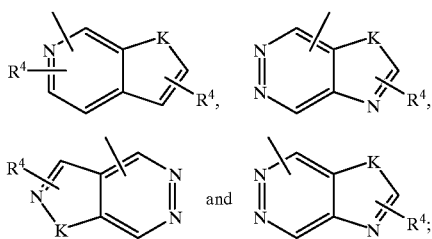

K is selected from O, S, NH, and N.

[3] In a more preferred embodiment, the present invention provides compounds of formula II:

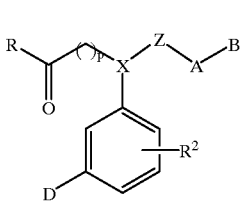

II wherein;

R is selected from OH, C$_{1-6}$ alkoxy, C$_{3-6}$ cycloalkoxy, C$_{6-10}$ aryloxy substituted with 0–2 $R^4$, C$_{1-6}$ alkyl substituted with 0–2 $R^5$, and NR$^1$R$^{1a}$;

R$^2$ is selected from H, OR$^1$, halo, and C$_{1-6}$ alkyl;

R$^3$ is selected from C$_{1-6}$ alkoxy, C$_{1-6}$ alkyl, and halo;

R$^5$ is selected from H, OH, C$_{1-6}$ alkoxy, phenyl, halo, CN, NO$_2$, NR$^6$R$^{6a}$, and C(=O)R$^6$;

X and Z together can be selected from C(R$^1$) (CH$_2$)$_q$S(O)$_m$ (CH$_2$)$_q$, C(R$^1$)N(R$^6$)S(O)$_m$, and N(CH$_2$)$_q$S(O)$_m$;

[4] In an even more preferred embodiment, the present invention provides compounds of formula II, wherein:

D is C(=NH)NH$_2$;

R is selected from OH, C$_{1-3}$ alkoxy, C$_{1-3}$ alkyl, NH$_2$, and NHR$^1$;

R$^1$ is C$_{1-3}$ alkyl substituted with 0–2 $R^5$;

R$^5$ is selected from OH, C$_{1-3}$ alkoxy, phenyl, CN, and NH$_2$;

X is selected from CHNH, CH, CH—O, and N;

Z is selected from (CH$_2$)$_n$ and C(=O);

X and Z together can be selected from C(H)(CH$_2$)S(O)$_2$, C(H)S(O)$_2$(CH$_2$)$_2$, C(H)N(H)S(O)$_2$, and N(CH$_2$)S(O)$_2$;

p is 1, 2, or 3;

A is selected from:
 piperidinyl,
 piperazinyl,
 C$_{5-6}$ carbocyclic residue substituted with 0–2 $R^4$, and
 5–6 membered heteroaryl containing from 1–4 heteroatoms selected from the group consisting of N, O, and S substituted with 0–2 $R^4$;

B is selected from B$^2$ and B$^1$-B$^2$;

B$^1$ is selected from C$_{1-4}$ alkylene, —C(O)—, —C(O)CR$^{10}$R$^{10a}$—, —CR$^{10}$R$^{10a}$C(O), —S(O)$_2$NR$^{10}$—, —C(O)NR$^{10}$—, —NR$^{10}$C(O)—, —NR$^{10}$—, and O; and, B$^2$ is selected from one of the following carbocyclic and heterocyclic systems which are substituted with 0–2 $R^{4a}$;

phenyl, piperidinyl, piperazinyl, pyridyl, pyrimidyl, furanyl, thiophenyl, pyrrolyl, oxazolyl, isoxazolyl, thiazolyl, isothiazolyl, pyrazolyl, imidazolyl, oxadiazole, thiadiazole, triazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3, 4-thiadiazole, 1,2,3-triazole, 1,2,4-triazole, 1,2,5-triazole, and 1,3,4-triazole.

[5] In an further preferred embodiment, the present invention provides novel compounds of formula II, wherein:

$R^6$ and $R^{6a}$ are independently selected from H, $C_{1-3}$ alkyl, $C_{1-3}$ alkoxy, $C_{3-6}$ cycloalkoxy, phenoxy;

X is selected from CH, CH—O, and N;

p is 1;

A is phenyl substituted with 0–1 $R^4$; and,

B is selected from $NH_2$, C(=NH)$NH_2$, NHC(=NH)$NH_2$, and phenyl substituted with 0–1 $R^4$.

[5] In a still further preferred embodiment, the compounds of formula II are selected from:

methyl 4-(aminoiminomethyl)-beta-[3-(aminoiminomethyl) phenyl]benzene pentanoate;

ethyl 4-(aminoiminomethyl)-beta-[3-(aminoiminomethyl) phenyl]benzene pentanoate;

methyl 4-[(aminoiminomethyl)amino]-beta-[3-(aminoiminomethyl)phenyl]benzenepentanoate;

methyl 4-[(aminoiminomethyl)amino]-beta-[3-(aminoiminomethyl)phenyl]benzeneheptanoate;

ethyl 3-(aminoiminomethyl)-beta-[[4-(aminoiminomethyl) phenyl]methoxy]benzenepropanoate;

N-[4-[4-[(aminoiminomethyl)amino]phenyl]butyl]-N-[3-(aminoiminomethyl)phenyl]glycine;

ethyl N-[3-(aminoiminomethyl)phenyl]-N-[4-(4-aminophenyl)butyl]glycine;

ethyl N-[4-[4-[(aminoiminomethyl)amino]phenyl]butyl]-N-[3-(aminoiminomethyl)phenyl]glycine;

methyl N-[3-(aminoiminomethyl)phenyl]-N-[3-[2'-(aminosulfonyl)[1,1'-biphenyl]-4-yl]propyl]glycine;

methyl N-[3-(aminoiminomethyl)phenyl]-N-[3-[2'-[[(1,1-dimethylethyl)amino]sulfonyl][1,1'-biphenyl]-4-yl] propyl]glycine;

methyl N-[3-(aminoiminomethyl)phenyl]-N-[2-[2'-(aminosulfonyl)[1,1'-biphenyl]-4-yl]ethyl]glycine; and, methyl N-[3-(aminoiminomethyl)phenyl]-N-[2-[2'-[[(1,1-dimethylethyl)amino]sulfonyl][1,1'-biphenyl]-4-yl]ethyl] glycine; or, stereoisomers or pharmaceutically acceptable salt forms thereof.

In a second embodiment, the present invention provides novel pharmaceutical compositions, comprising: a pharmaceutically acceptable carrier and a therapeutically effective amount of a compound of formula (I) or a pharmaceutically acceptable salt or prodrug form thereof.

In a third embodiment, the present invention provides a novel method for treating or preventing a thromboembolic disorder, comprising: administering to a patient in need thereof a therapeutically effective amount of a compound of formula (I) or a pharmaceutically acceptable salt or prodrug form thereof.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

When any variable (for example, $R^4$, $R^5$, $R^6$, etc.) occurs more than one time in any constituent or formula for a compound, its definition on each occurrence is independent of its definition at every other occurrence. Thus, for example, if a group is shown to be substituted with 0–3 $R^4$, then said group may optionally be substituted with up to three $R^4$ and $R^4$ at each occurrence is selected independently from the defined list of possible $R^4$. Also, combinations of substituents and/or variables are permissible only if such combinations result in stable compounds.

As used herein, "$C_{1-6}$ alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl; "$C_{1-2}$ haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)), examples of which include, but are not limited to, trifluoromethyl, perfluoroethyl, and trichloromethyl; "$C_{1-6}$ alkoxy" represents an alkyl group of indicated number of carbon atoms attached through an oxygen bridge, examples include, but are not limited to, methoxy, ethoxy, propoxy, isopropoxy, and butoxy; "cycloalkyl" is intended to include saturated ring groups, including mono-,bi- or poly-cyclic ring systems, such as cyclopropyl, cyclobutyl, cyclopentyl, cyclohexyl, cycloheptyl, adamantyl and cyclooctyl; and "biycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl, and the like; and "alkynyl" is intended to include hydrocarbon chains of either a straight or branched configuration and one or more triple carbon-carbon bonds which may occur in any stable point along the chain, such as ethynyl, propynyl and the like.

"Alkylcarbonyl" is intended to include an alkyl group of an indicated number of carbon atoms attached through a carbonyl group to the residue of the compound at the designated location. "Alkylcarbonylamino" is intended to include an alkyl group of an indicated number of carbon atoms attached through a carbonyl group to an amino bridge, where the bridge is attached to the residue of the compound at the designated location. "Alkylcarbonyloxy" is intended to include an alkyl group of an indicated number of carbon atoms attached to a carbonyl group, where the carbonyl group is attached through an oxygen atom to the residue of the compound at the designated location.

"Halo" or "halogen" as used herein refers to fluoro, chloro, bromo, and iodo; and "counterion" is used to represent a small, negatively charged species such as chloride, bromide, hydroxide, acetate, sulfate, and the like.

As used herein, "aryl" or "aromatic residue" is intended to mean phenyl or naphthyl; the term "arylalkyl" represents an aryl group attached through an alkyl bridge. By way of examples: the term "$C_{7-10}$ arylalkyl" is intended to refer to an aryl group attached through a $C_1$–$C_4$ alkyl bridge to the residue of the indicated compound; the term "($C_1$–$C_3$ alkyl)

aryl" is intended to refer to a $C_1$–$C_3$ alkyl group which is attached through an aryl ring to the residue of the indicated compound; the term "aryl($C_1$–$C_3$ alkyl)" is intended to refer to an aryl group attached through a $C_1$–$C_3$ alkyl group to the residue of the indicated compound.

As used herein, "carbocycle" or "carbocyclic residue" is intended to mean any stable 3- to 7-membered monocyclic or bicyclic or 7- to 10-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, naphthyl, indanyl, adamantyl, or tetrahydronaphthyl (tetralin).

As used herein, the term "heterocycle" is intended to mean a stable 5- to 7-membered monocyclic or bicyclic or 7- to 10-membered bicyclic heterocyclic ring which is either saturated or unsaturated, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiophenyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindolinyl, isoindolyl, isoquinolinyl (benzimidazolyl), isothiazolyl, isoxazolyl, morpholinyl, naphthyridinyl, octahydroisoquinolinyl, oxazolidinyl., oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, tetrazolyl, 6H-1,2,5-thiadiazinyl, thianthrenyl, thiazolyl, thienyl, thienothiazole, thienooxazole, thienoimidazole, thiophenyl, triazinyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and spiro compounds containing, for example, the above heterocycles.

When a bond to a substituent is shown to cross the bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

The term "substituted", as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula (I), and the like. Preferred prodrugs are amidine prodrugs wherein D is $C(=NR^7)NH_2$, and $R^7$ is selected from OH, $C_{1-4}$ alkoxy, $C_{6-10}$ aryloxy, $C_{1-4}$ alkoxycarbonyl, $C_{6-10}$ aryloxycarbonyl, $C_{6-10}$ arylmethylcarbonyl, $C_{1-4}$ alkylcarbonyloxy $C_{1-4}$ alkoxycarbonyl, and $C_{6-10}$ arylcarbonyloxy $C_{1-4}$ alkoxycarbonyl. More preferred prodrugs are where $R^7$ is OH, methoxy, ethoxy, benzyloxycarbonyl, methoxycarbonyl, and methylcarbonyloxymethoxycarbonyl.

"Stable compound" and "stable structure" are meant to indicate a compound that is sufficiently robust to survive isolation to a useful degree of purity from a reaction mixture, and formulation into an efficacious therapeutic agent.

SYNTHESIS

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include but are not limited to those methods described below. Each of the references cited below are hereby incorporated herein by reference. All the temperatures are reported herein in degrees Celsius.

Compounds of Formula (I) may be prepared using the reactions and techniques described in this section. The reactions are performed in solvents appropriate to the reagents and materials employed and suitable for the transformation being effected. It is understood by those skilled in the art of organic synthesis that the functionality present on the phenyl rings and other portions of the molecule must be compatible with the reagents and reaction conditions proposed. Not all compounds of Formula (I) falling into a given class may be compatible with some of the reaction conditions required in some of the methods described. Such restrictions to the substituents which are compatible with the reaction conditions will be readily apparent to one skilled in the art and alternative methods described must then be used. Even though the following schemes depict E as only being phenyl, one of ordinary skill in the art would recognize that this phenyl ring could readily be replaced with other E groups such as pyridyl or pyrimidyl. One of ordinary skill in the art would also recognize that some of the conditions used may need to be slightly modified when an E group other than phenyl is present.

Compounds of Formula (I) wherein X is $CR^1$ or $CHCH$ ($R^1$) can be prepared by routes shown in Scheme 1, wherein R' and Y are defined below.

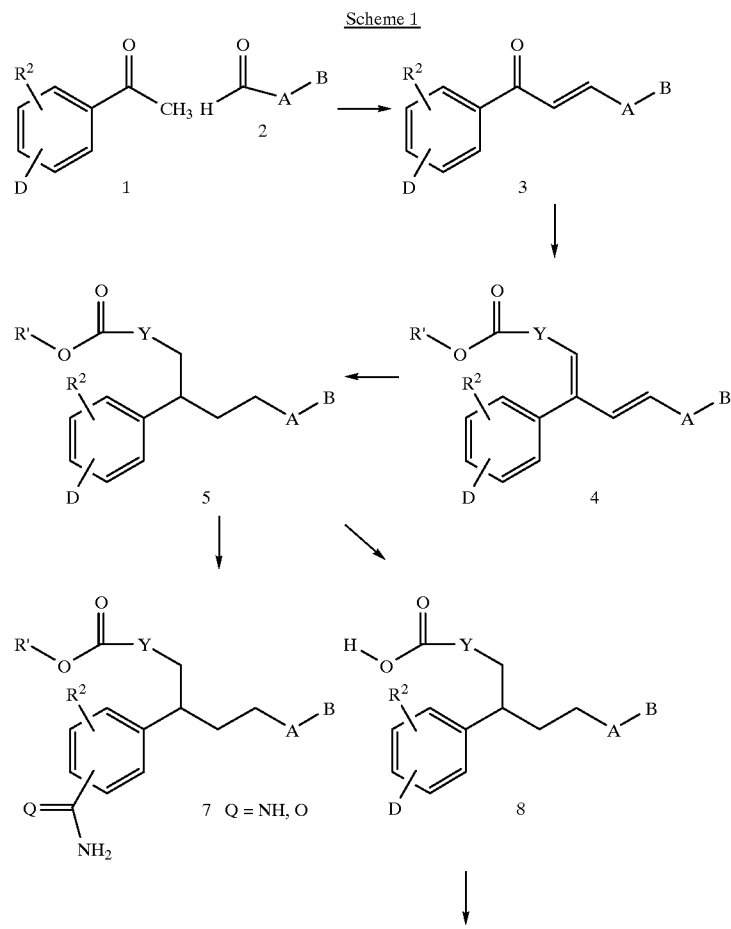

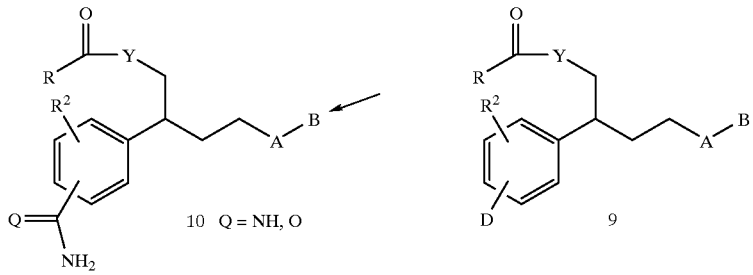

The enone of Formula (3) can be prepared by aldol like condensations using an appropriately substituted acetophenone compound of Formula (1) and an appropriately substituted aldehyde of Formula (2) with a variety of bases like sodium methoxide, potassium hydroxide, or lithium diisopropyl amine in solvents such as methanol, tetrahydrofuran, ethyl ether or N,N-dimethylformamide. The diene of Formula (4), wherein Y corresponds to $R^a(CH_2)_{p-1}$ and R' corresponds to $C_{3-6}$ cycloalkyl, $C_{1-6}$ alkyl, or $C_{6-10}$ aryl, can be prepared by reaction of the enone of compound of Formula (3) with a variety of phosphonium ylids which can be readily purchased from vendors like Aldrich Chemical Company or prepared by methods well known in the art. The saturated compound of Formula (5) can be prepared by hydrogenation methods well documented in the literature by those skilled in the art of organic synthesis. For example, reduction of the diene of Formula (4) can be carried out under Parr conditions using 20–50 psi hydrogen or atmospheric hydrogen pressure with a catalyst like 10% palladium on charcoal in a solvent like methanol, ethyl acetate or tetrahydrofuran, or hydrogenation conditions using cyclohexene as the hydrogen source in a solvent such as ethanol with 10% palladium on charcoal.

The bisamidine compound of Formula (7) wherein Q is NH and B is amidine can be prepared from a compound of Formula (5) by well known methods. For example, conversion of the bisnitrile compound of Formula (5), wherein D and B are nitrile, using Pinner synthesis methods like a hydrochloric acid saturated methanol or ethanol solution to prepare the intermediate imidates and conversion of the imidate to the amidines with ammonia gas saturated methanol or ethanol; or, use of other ammonia sources like ammonium carbonate or ammonium acetate. The bisamidines are usually isolated after HPLC purification on a reverse phase C-18 column using a gradient elution of acetonitrile, water and trifluoroacetic acid.

Alternatively the guanidine amidine compound of Formula (7) wherein Q is NH and B is guanidine can be prepared by a two step process starting with the amino nitrile compound of Formula (5) wherein D is nitrile and B is NH2. The amine is converted to the guanidine by methods well known in the literature, like 3,5 dimethylpyrazole-1-carboxamidine nitrate in a solvent like pyridine at elevated temperatures. The guanidine compound of Formula (5) wherein B is guanidine can be purified or carried on to the amidine guanidine compound of Formula (7) wherein Q is NH and B is guanidine by amidine forming methods previously described.

The acid compound of Formula (8) can be prepared from the ester compound of Formula (5) wherein R is a simple alkyl group by methods which are well known in the chemical literature. For example, the hydrolysis can be accomplished by reaction with an alkali metal hydroxide such as lithium hydroxide in aqueous or organic solvents such as water, alcohols, ethers or mixtures thereof, followed by acidification with a mineral acid.

The amide compounds of Formula (9) wherein R is connected by N can be prepared by amide bond forming reactions which are well known in the chemical literature. One method for amide bond formation is to use a coupling reagent which generates a reactive intermediate such as a mixed anhydride or active ester. Examples of such coupling agents are disubstituted carbodiimides, N,N'-carbonyldiimidazole, diphenylphosphoryl azide, and the like. For example, the coupling can be carried out with a disubstituted carbodiimide such as dicyclohexylcarbodiimide in an appropriate solvent such as methylene chloride, acetonitrile, toluene, or N,N-dimethylformamide. Nucleophilic hydroxyl compounds such as 1-hydroxy-1H-benzotriazole, which forms a highly active ester, may be added to catalyze the reaction. Alternatively, the acid compounds of Formula (8) can be converted to the corresponding acid chloride using thionyl chloride, oxalyl chloride or the like and then to react the acid chloride with a primary or secondary amine which is readily available, in the presence of a base such as triethylamine to afford the amide compounds of Formula (9) wherein R3 is connected through an N.

The amide compounds containing amidine and or guanidines of Formula (10) wherein Q is NH and B is amidine or guanidine can be prepared by methods similar to those previously described for the conversion of compound Formula (5) to compound of Formula (7) wherein Q is NH and B is amidine or quanidine.

The amide compound of Formula (7) and Formula (10) wherein Q is O can be prepared by conversion of the nitrile compound of Formula (5) and Formula (9) wherein D is nitrile to the intermediate imidate by methods previously described, then addition of water to give the amides.

Compounds of Formula (I) wherein X is CH—O can be prepared by the route shown in Scheme 2.

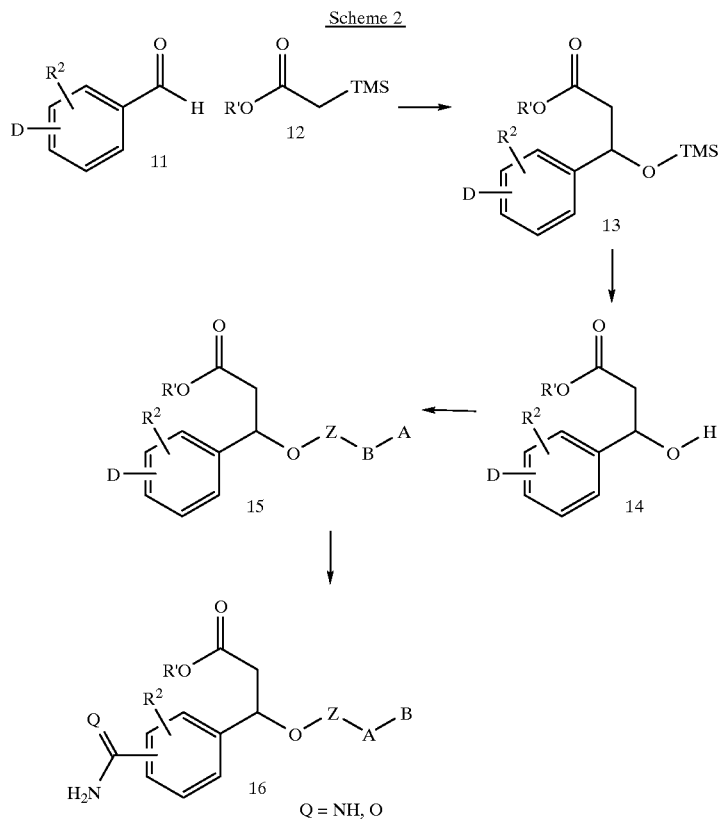

The trimethylsilyl ether compound of Formula (13) can be prepared by condensation of a trimethyl silylacetate compound of Formula (12) with an appropriately substituted benzaldehyde compound of Formula (11) using catalytic tetrabutyl ammonium floride, in a solvent such as tetrahydrofuran at reduced temperatures (E. Nakamura, M. Shimizu, I. Kuwajima, Tet. Lett, 1699, 1979). The free hydroxyl compound of Formula (14) can be prepared by treating the trimethylsilyl ether compound of Formula (13) by methods well known in the chemical literature. For example, the silyl ethers can be removed with tetrabutyl ammonium floride in a solvent such as tetrahydrofuran.

The ether compound of Formula (15) can be prepared by methods well known in the chemical literature for the formation of ether linkages. For example reaction of the alcohol compound of Formula (14) with a base such as sodium hydride, silver oxide, or cesium carbonate and reacting the alkali metal salt with an appropriately substituted reagent containing a leaving group such as a bromide, tosylate or similar functionality in an appropriate aprotic solvent such as tetrahydrofuran, methylene chloride, acetone or toluene. Alternatively, the alcohol compound of Formula (14) can be reacted with appropriately substituted compounds containing an alcohol under Mitsunobo like ether bond forming reaction conditions, like triphenylphosphorane and diethyl azodicarboxylate in a solvent like tetrahydrofuran. The amidine compounds of Formula (16) wherein Q is NH, and B is amidine can prepared from the bisnitrile compound of Formula (15) by Pinner synthesis methods previously described.

Compounds of Formula (I) wherein X is CHN($R^1$) can be prepared by the route shown in Scheme 3.

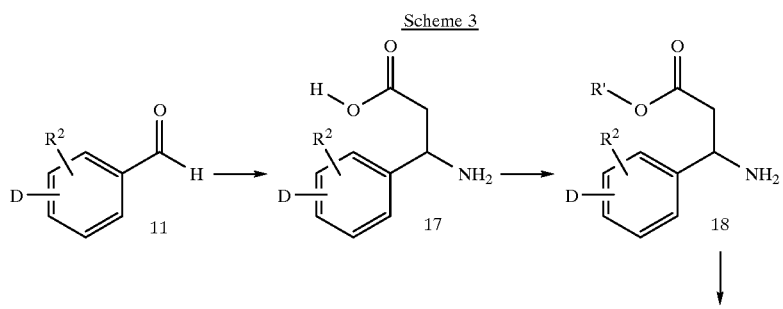

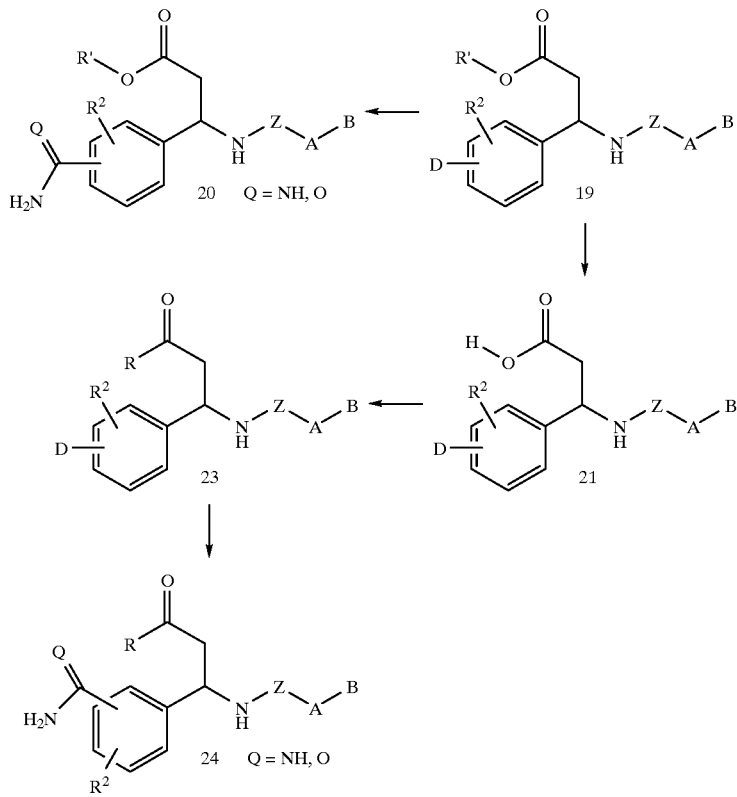

The amino compound of Formula (17) can be prepared by methods described in the chemical literature (Treat Johnson, John Livak, J. Am. Chem. Soc. 299, 1939). The ester compound of Formula (18) wherein R' is a lower alkyl group may be prepared by ester bond forming reaction well described in the chemical literature. For example reacting the free acid compound of Formula (17) in an alcohol solvent like methanol or ethanol with a catalytic amount of acid like hydrogen chloride or toluenesulphonic acid. The amide compound of Formula (19) wherein R is connected by a carbonyl group can be prepared from the amino compound of Formula (18) by amide bond forming methods previously described. Alternatively sulphonamide compounds of Formula (19) wherein A is connected by an $SO_2$ group can be prepared by reaction of the amino compound of Formula (18) with an appropriately substituted sulfonyl chloride with an acid scavenger like sodium hyroxide or triethyl amine in a solvent such as methanol, tetrahydrofuran, methylene chloride and water or mixtures thereof. Alternatively, amine compounds of Formula (19) where Z is connected by a carbon atom can be prepared by methods for forming secondary amines well known in the chemical literature. For example amine compounds of Formula (19) wherein Z is connected by a carbon atom can be prepared by condensation of the amino compound of Formula (18) with an appropriately substituted aldehyde containing compound to give the imine. The imine can be reduced by hydrogenation conditions like hydrogen gas and palladium on charcoal or by reducing reagents like sodium borohydride in solvents like methanol. Alternatively, the amine compounds of Formula (19) wherein Z is connected by a carbon atom can be prepared by reaction of the the amino compound of Formula (18) with an appropriately substituted reagent containing a leaving group such as a bromide, tosylate or similar functionality in an appropriate aprotic solvent such as tetrahydrofuran, methylene chloride, acetone or toluene containing an acid scavenger like triethylamine.

The acid compound of Formula (21) can be prepared from the ester compound of Formula (19) by methods well known in the chemical literature for hydrolysis of an ester, and previously described. The amide compound of Formula (23) wherein R is connected by N or the ester compound of Formula (23) wherein R is connected by O can be prepared from the acid compound of Formula(21) by methods well known in the chemical literature for amide bond forming reactions and ester bond forming reactions, previously described. The amidine or amide compounds of Formula (20) and (24) wherein Q is NH or O can be prepared by methods previously described.

Compounds of Formula (I) wherein X is CH—O, p=2 and Q is NH can be prepared by the route shown in Scheme 4.

Scheme 4

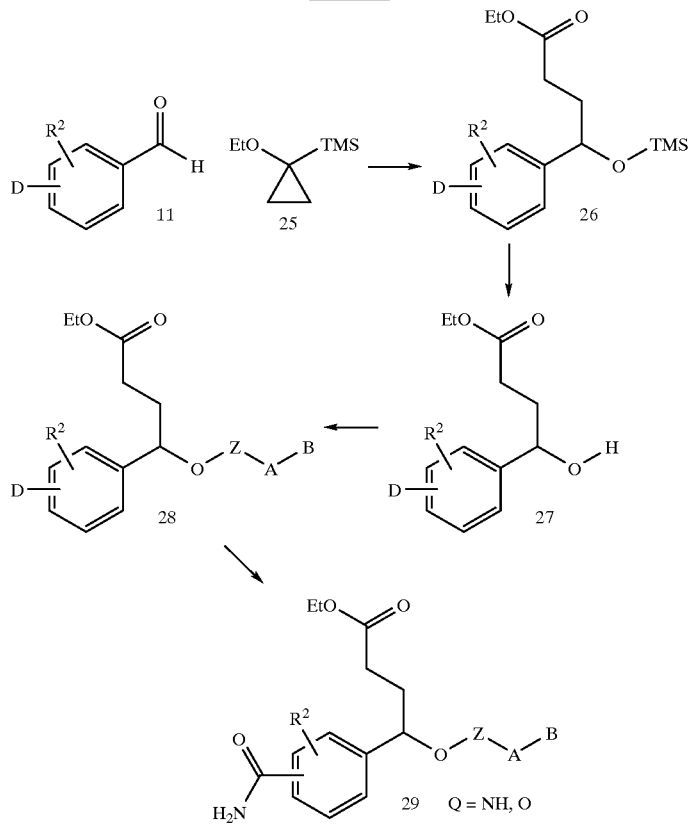

The compounds of Formula (26) can be prepared by methods described in the literature, (*J. Org. Chem.* 1985, 50(15), 2802), by reacting the appropriately substituted benzaldehyde with 1-ethoxy-1-trimethylsilyloxycyclopropane and a catalytic amount of tetrabutylammonium fluoride in trahydrofuran. The alcohol compound of Formula (27) can be prepared from the silylether compound of Formula (26) by methods well described in the literature. For example the silyl group may be removed by reaction with tetrabutylammonium floride in tetrahydrofuran. The ether compound of Formula (28) can be prepared from the alcohol compound of Formula (27) as previously described for compound of Formula (15), Scheme 2. The amidine or amide compound of Formula (29) wherein Q is NH or O can be prepared from the nitrile compound of Formula (28) wherein D is nitrile by methods previously described.

Amidine compounds of Formula (I) wherein X is N or NCH($R^1$) can be prepared by the routes shown in Scheme 5.

Scheme 5

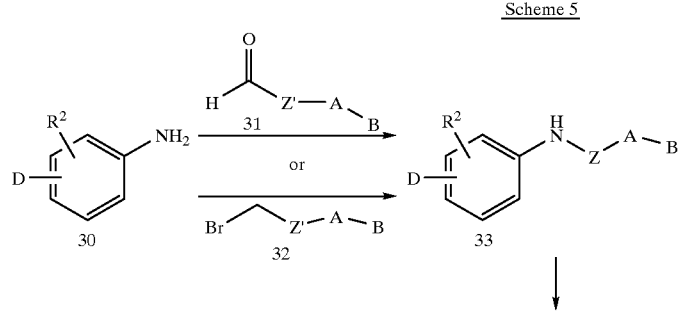

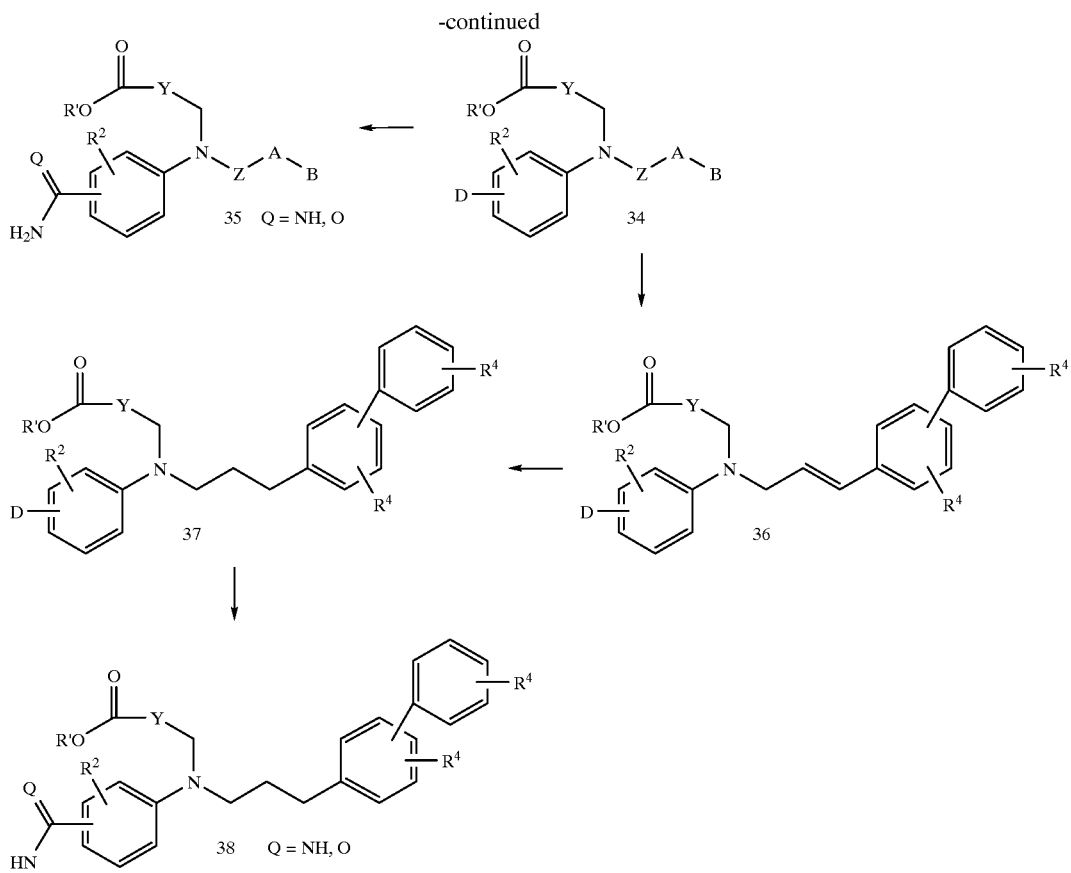

The secondary amine of Formula (33) can be prepared by a variety of carbon nitrogen bond forming reaction well described in the literature and previously detailed in this application. For example the appropriately substituted amine compound of Formula (30) can be alkylated by reductive amination methods using an appropriately substituted aldehyde under dehydrating conditions to give the imine. Then the resulting imine can be reduced with reducing agents like sodium borohydride or sodium cyanoborohydride in a solvent like methanol. Alternatively, the secondary amine of Formula (33) can be prepared by alkylation of the amine compound of Formula (30) with a compound like Formula (32) containing a leaving group such as a bromide, tosylate or similar functionality, with a base like pyridine in solvent like hexamethylphosphoramide at elevated temperatures. Alternatively the alkylation can be carried out under phase transfer conditions using tris[2-(2-methoxy)ethoxyethyl] amine with sodium bicarbonate at elevated temperatures. It is noted that when E is other than phenyl, more forcing conditions may be necessary. For example, if E is pyridyl, then the compound of Formula (31) may need to be an acid chloride.

The tertiary amine of Formula (34) can be prepared by reaction with an appropriately substituted ester group under methods previously described for compounds of Formula (33), but usually at higher temperatures. The amidine and amide compounds of Formula (35) can be prepared from the nitrile compound of Formula (34) wherein D is nitrile by methods previously detailed.

The compounds of Formula (I) wherein X is N and Z is C=O or C=ONH can be prepared by routes similar to Scheme 5. The aniline compound of Formula (30) can be reacted with an appropriately substituted acid chloride, activated acid or isocyanate in solvents like methylene chloride, tetrahydrofuran or toluene by methods well known in the literature by those skilled in the art of organic synthesis.

The biphenyl compound of Formula (36) can be prepared from the phenyl compound of Formula (34) wherein A is phenyl or cinnamyl or the like and B is bromide by Suzuki like coupling methodology which is well know in the chemical literature, for example, using an appropriately substituted phenyl boronic acid and a palladium catalyst like tetrakis(triphenylphosphine)palladium(0) in a solvent like toluene and water at elevated temperatures.

The biphenyl compound of Formula (37) can be prepared from the olefin compound of Formula (36) by reduction methods well known in the literature and some of which were previously described above. The amidine and amide compounds of Formula (38) wherein A is NH or O can be prepared from the nitrile compound of Formula (34) wherein D is nitrile by methods previously detailed.

SCHEME 6

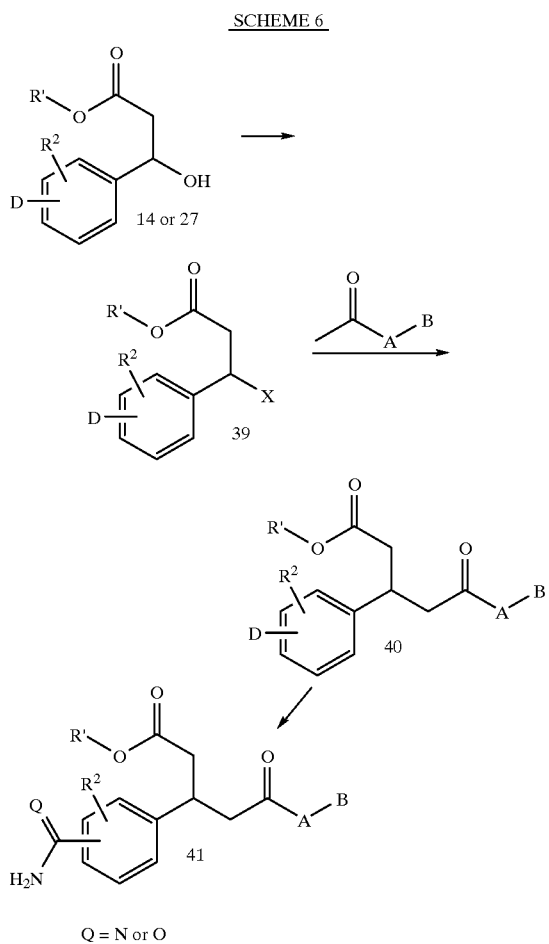

SCHEME 7

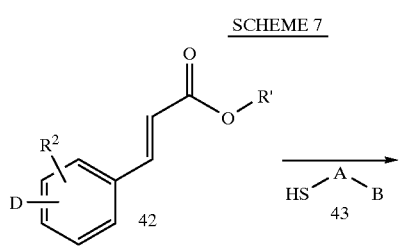

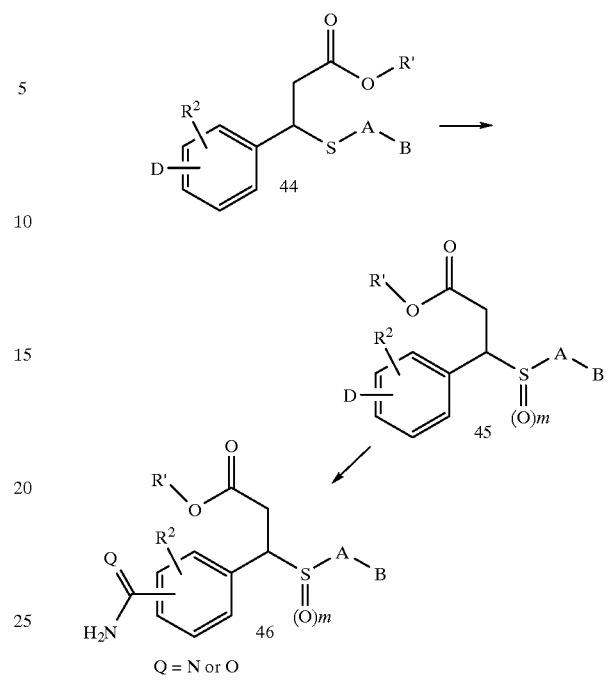

The compounds of Formula (I) wherein X is CHCH2 and Z is C=O can be prepared by methods as outline in Scheme 6. The bromide compound of Formula (39) can be prepared from the hydroxy compound of Formula (14) or (27) by methods previously described and well known in the literature, like triphenyl phosphine and carbon tetrabromide in toluene. The carbonyl compound of Formula (40) can be prepared by reaction of alkali metal enolate of an appropriately substituted methyl ketone with the leaving group of compound of Formula (39). The enolate may be generated with lithium diisopropyl amine in tetrahyrofuran at reduced temperatures and an appropriately substituted methyl ketone. The amidine and amide compound of Formula (41) may be prepared from the nitrile compound of Formula (40) wherein D is nitrile by methods previously detailed.

The sulfur compound of Formula (I) wherein X is CH and Z is S(O)m can be prepared by methods outlined in Scheme 7. The compound of Formula (44) can be prepared by the reaction of the alkali metal salt of an appropriately substituted thio compound of Formula (43) with an appropriate α,β-unsaturated ester compound of Formula (42) in a Michael like manner, or with the compound of Formula (39) wherein X is bromide, mesylate, or other leaving group by methods well known in the literature. The compound of Formula (45) wherein m is 1 or 2 may be prepared from the sulfur containing compound of Formula (44) by reaction with an oxidizing agent such as m-chloroperbenzoic acid in methylene chloride or tetrahydrofuran or other agents well known in the literature for this transformation. When E is other than phenyl, particular care in selection of the oxidizing agent would be necessary so as to not oxidize the nitrogen ring atoms. The amidine and amide compound of Formula (46) may be prepared from the nitrile compound of Formula (45) wherein D is nitrile by methods previously detailed.

SCHEME 8

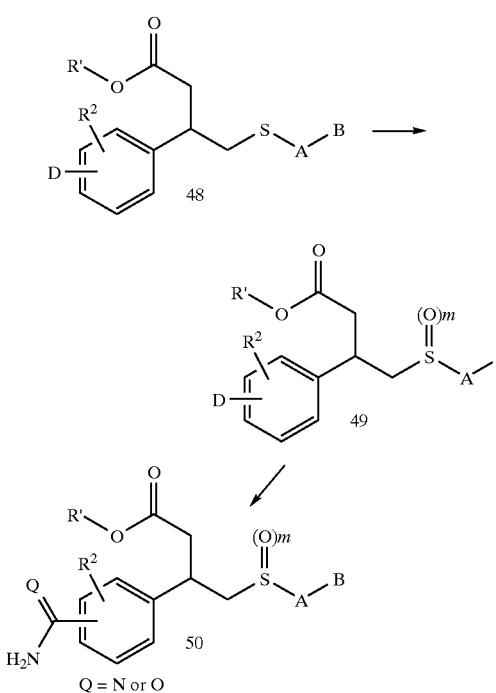

The sulfur compound of Formula (I) wherein X is CHCH2 and Z is S(O)m can be prepared by methods outline in Scheme 8. The appropriately substituted compound of Formula (47) wherein X is a leaving group like bromide or tosylate can be prepared from the appropriate hydroxy compound of Formula (47) where in X is OH by methods well know in the literature. The compound of Formula (47) wherein X is OH can be prepared directly, by methods similar to P. G Ciattini et al, Synthesis (1) p. 70, 1986, or alternatively stepwise by reacting an appropriately substituted acetophenone with a Wittig like phosphonium reagent similar to Eguchi, et al, Tetrahedron Let. 33 (1992) 38, 5545–5546, and then oxidation to the alcohol or bromination to give the compound of Formula (47) wherein X is OH or Br respectively. The thio compound of Formula (48) can be prepared from compound of Formula (47) wherein X is a leaving group like bromide, tosylate or the like, by reaction with the alkali metal salt of an appropriately substituted thio compound of Formula (43) previously described. The compound of Formula (49) wherein m is 1 or 2 can be prepared from the sulfur containing compound of Formula (48) by the action of an oxidizing agent such as m-chloroperbenzoic acid as previously described. As with Scheme 7, when E is other than phenyl, particular care in selection of the oxidizing agent would be necessary so as to not oxidize the nitrogen ring atoms. The amidine and amide compound of Formula (50) may be prepared from the nitrile compound of Formula (49) wherein D is nitrile by methods previously detailed.

SCHEME 9

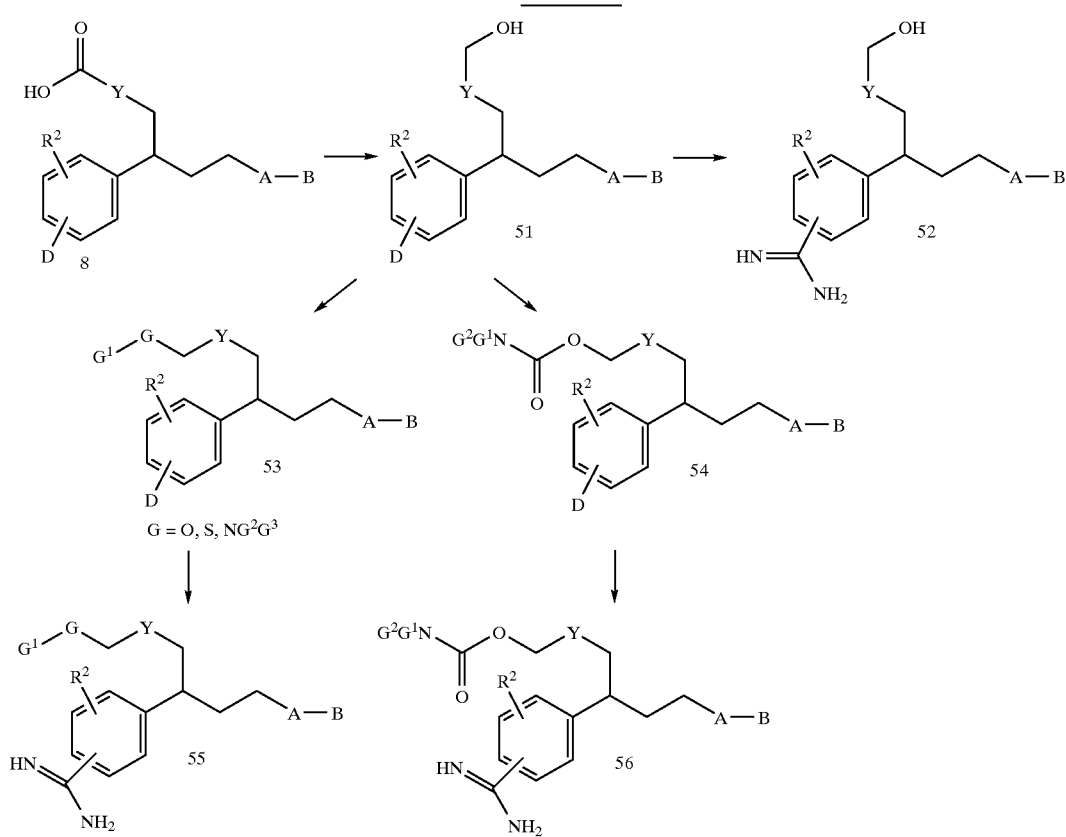

Scheme 9 describes how to make compounds of Formula I wherein X is CH, $R^a$ is a bond, and $R^b$ is G. The alcohol of Formula (51) can be prepared by combining isobutylchloroformate, with a base like triethylamine or N-methyl morpholine and compound of Formula (8) in solvents such as tetrahydrofuran or dimethoxyethane. The resultant mixed anhydride can then be reduced to Formula (51) with sodium borohydride. The amidine of Formula (52) can be prepared from the compounds of Formula (51) wherein D is a nitrile by methods previously detailed.

The carbamate of Formula (54) can be prepared from the alcohol compound of Formula (51) by the reaction of an appropriately substituted isocyanate in the presence of a base, e.g., diisopropyl ethyl amine, in a solvent such as toluene at an elevated temperature. The amidine of Formula (56) can be prepared from compounds of Formula (54) wherein D is a nitrile by methods previously detailed.

Compounds of Formula (53) can be prepared by reaction of an appropriately substituted amine, alkoxide or thiolate anion with a compound of Formula (51) containing a leaving group such as a bromide, tosylate or similar functionality with a base similar to pyridine in a solvent not unlike hexamethylphosphoramide at elevated temperatures. Also, compounds of Formula (53), wherein $G^1$ is aryl and G is oxygen or sulfur, can be prepared by utilizing Mitsunobu methodology well documented in the literature. For example, compounds of Formula (51) can be combined with an appropriately substituted phenol or thiophenol in the presences of triphenylphosphine and diethylazodicarboxylate in a solvent similar to methylene chloride at room temperature. Alternatively, alkyl, aryl, heterocyclic and carbocyclic substitution on compounds of Formula (51) can be carried out under phase transfer conditions using an appropriately substituted alkyl, aryl, heterocyclic or carbocyclic halide with tris-[2-(2-methoxy)ethoxyethyl]amine and sodium bicarbonate at elevated temperatures. The amidine of Formula (55) can be prepared from compounds of Formula (53) wherein D is a nitrile by methods previously detailed.

SCHEME 10

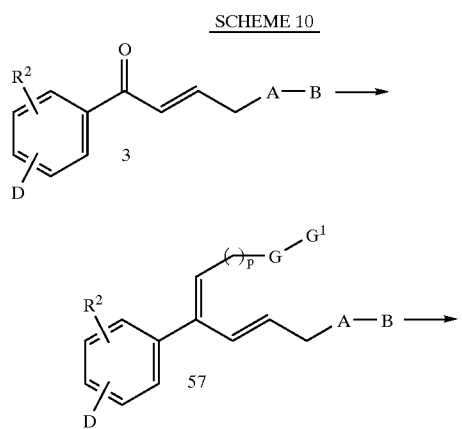

As shown in Scheme 10, the diene of Formula (57) can be prepared by the reaction of the eneone of compound of Formula (3) with a variety of phosphonium ylides which can be readily purchased from vendors like Aldrich Chemical Company or prepared by methods well known in the art. The saturated compound of Formula (58) can be prepared by hydrogenation methods well documented in the literature of organic synthesis and previously described. The amidine of Formula (59) can be prepared from compounds of Formula (58) wherein D is a nitrile by methods previously detailed.

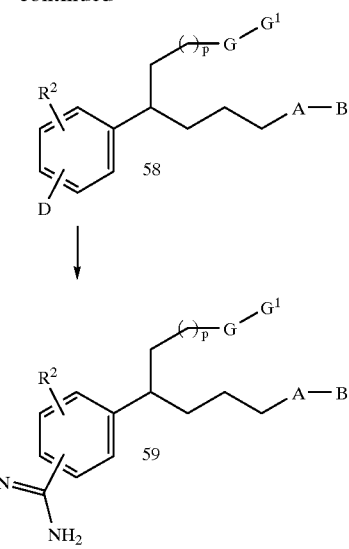

SCHEME 11

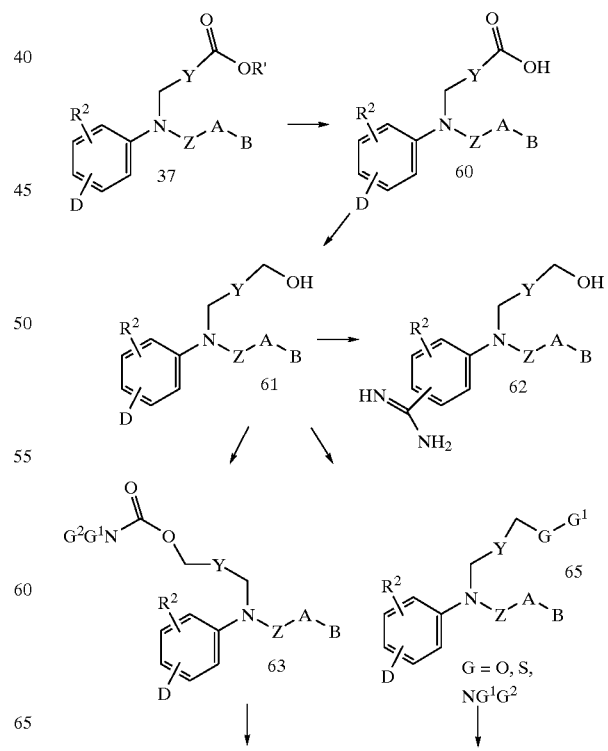

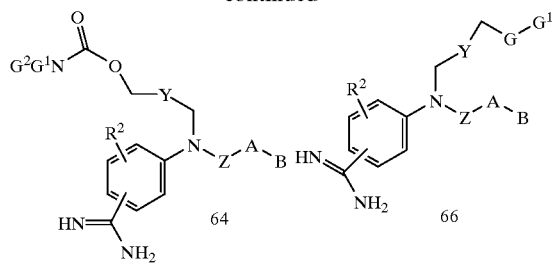

Scheme 11 describes the synthesis of a variety of substituted anilines. The acid compound of Formula (60) can be prepared from the ester compound of Formula (34) by methods well known in the chemical literature for the hydrolysis of an ester, and previously described. The hydroxyl compound of Formula (61) can be prepared from acid the compound of Formula (60) by sodium borohydride reduction of its corresponding mixed anhydride as previously described. The amidine of Formula (62) can be prepared from compounds of Formula (61) wherein D is a nitrile by methods previously detailed.

The carbamate of Formula (63) can be prepared by the alcohol compound of Formula (61) by the reaction of an appropriately substituted isocyanate in the presence of a base like diisopropyl ethyl amine in a solvent like toluene at an elevated temperature. The amidine of Formula (64) can be prepared from compounds of Formula (63) wherein D is a nitrile by methods previously detailed.

Compounds of Formula (65) can be prepared by the action of an appropriately substituted amine, alkoxide or thiolate anion with a compound of Formula (61) containing a leaving group such as a bromide, tosylate or similar functionality with a base like pyridine in a solvent like hexamethylphophoramide at elevated temperatures. Also, compounds of Formula (65) wherein R is aryl and X is oxygen or sulfur, can be prepared by utilizing Mitsunobu methodology. For example, compounds of Formula (61) can be combined with an appropriately substituted phenol or thiophenol, triphenylphosphine and diethylazodicarboxylate in a solvent such as methylene chloride at room temperature. Alternatively, alkyl, aryl, heterocyclic or carbocyclic substitution on compounds of Formula (64) can be carried out under phase transfer conditions using an appropriately substituted alkyl or aryl heterocyclic or carbocyclic halide with tris [2-(2-methoxy)ethoxyethyl]amine and sodium bicarbonate at elevated temperatures. The amidine of Formula (66) can be prepared from compounds of Formula (65) wherein D is a nitrile by methods previously detailed.

When B is defined as $B^1$–$B^2$, the following description applies. Groups A and B are available either through commercial sources, known in the literature or readily synthesized by the adaptation of standard procedures known to practioners skilled in the art of organic synthesis. The required reactive functional groups appended to analogs of A and B are also available either through commercial sources, known in the literature or readily synthesized by the adaptation of standard procedures known to practioners skilled in the art of organic synthesis. In the tables that follow the chemistry required to effect the coupling of A to B is outlined.

TABLE A

Preparation of Amide, Ester, Urea, Sulfonamide and Sulfamide linkages between A and B

| Rxn. No. | if A contains: | then the reactive substituent of $B^2$ is: | to give the following product A-$B^1$-$B^2$: |
|---|---|---|---|
| 1 | A-NHR$^{10}$ as a substituent | ClC(O)-$B^2$ | A-NR$^{10}$-C(O)-$B^2$ |
| 2 | a secondary NH as part of a ring or chain | ClC(O)-$B^2$ | A-C(O)-$B^2$ |
| 3 | A-OH as a substituent | ClC(O)-$B^2$ | A-O-C(O)-$B^2$ |
| 4 | A-NHR$^{10}$ as a substituent | ClC(O)-CR$^{10}$R$^{10a}$-$B^2$ | A-NR$^2$-C(O)-CR$^{10}$R$^{10a}$-$B^2$ |
| 5 | a secondary NH as part of a ring or chain | ClC(O)-CR$^{10}$R$^{10a}$-$B^2$ | A-C(O)-CR$^{10}$R$^{10a}$-$B^2$ |
| 6 | A-OH as a substituent | ClC(O)-CR$^{10}$R$^{10a}$-$B^2$ | A-O-C(O)-CR$^{10}$R$^{10a}$-$B^2$ |
| 7 | A-NHR$^{10}$ as a substituent | ClC(O)NR$^{10}$-$B^2$ | A-NR$^{10}$-C(O)NR$^{10}$-$B^2$ |
| 8 | a secondary NH as part of a ring or chain | ClC(O)NR$^{10}$-$B^2$ | A-C(O)NR$^{10}$-$B^2$ |
| 9 | A-OH as a substituent | ClC(O)NR$^{10}$-$B^2$ | A-O-C(O)NR$^{10}$-$B^2$ |
| 10 | A-NHR$^{10}$ as a substituent | ClSO$_2$-$B^2$ | A-NR$^{10}$SO$_2$-$B^2$ |
| 11 | a secondary NH as part of a ring or chain | ClSO$_2$-$B^2$ | A-SO$_2$-$B^2$ |
| 12 | A-NHR$^{10}$ as a substituent | ClSO$_2$-CR$^{10}$R$^{10a}$-$B^2$ | A-NR$^2$-SO$_2$-CR$^{10}$R$^{10a}$-$B^2$ |
| 13 | a secondary NH as part of a ring or chain | ClSO$_2$-CR$^{10}$R$^{10a}$-$B^2$ | A-SO$_2$-CR$^{10}$R$^{10a}$-$B^2$ |
| 14 | A-NHR$^{10}$ as a substituent | ClSO$_2$-NR$^{10}$-$B^2$ | A-NR$^{10}$-SO$_2$-NR$^{10}$-$B^2$ |
| 15 | a secondary NH as part of a ring or chain | ClSO$_2$-NR$^2$-$B^2$ | A-SO$_2$-NR$^2$-$B^2$ |
| 16 | A-C(O)Cl | HO-$B^2$ as a substituent | A-C(O)-O-$B^2$ |
| 17 | A-C(O)Cl | NHR$^{10}$-$B^2$ as a substituent | A-C(O)-NR$^{10}$-$B^2$ |
| 18 | A-C(O)Cl | a secondary NH as part of a ring or chain | A-C(O)-$B^2$ |
| 19 | A-CR$^{10}$R$^{10a}$C(O)Cl | HO-$B^2$ as a substituent | A-CR$^{10}$R$^{10a}$C(O)-O-$B^2$ |
| 20 | A-CR$^{10}$R$^{10a}$C(O)Cl | NHR$^{10}$-$B^2$ as a substituent | A-CR$^{10}$R$^{10a}$C(O)-NR$^{10}$-$B^2$ |
| 21 | A-CR$^{10}$R$^{10a}$C(O)Cl | a secondary NH as part of a ring or chain | A-CR$^{10}$R$^{10a}$C(O)-$B^2$ |
| 22 | A-SO$_2$Cl | NHR$^{10}$-$B^2$ as a substituent | A-SO$_2$-NR$^{10}$-$B^2$ |
| 23 | A-SO$_2$Cl | a secondary NH as part of a ring or chain | A-SO$_2$-$B^2$ |
| 24 | A-CR$^{10}$R$^{10a}$SO$_2$Cl | NHR$^{10}$-$B^2$ as a substituent | A-CR$^{10}$R$^{10a}$SO$_2$-NR$^{10}$-$B^2$ |
| 25 | A-CR$^{10}$R$^{10a}$SO$_2$Cl | a secondary NH as part of a ring or chain | A-CR$^{10}$R$^{10a}$SO$_2$-$B^2$ |

The chemistry of Table A can be carried out in aprotic solvents such as a chlorocarbon, pyridine, benzene or toluene, at temperatures ranging from –20° C. to the reflux point of the solvent and with or without a trialkylamine base.

TABLE B

Preparation of ketone linkages between A and B

| Rxn. No. | if A contains: | then the reactive substituent of $B^2$ is: | to give the following product $A-B^1-B^2$: |
|---|---|---|---|
| 1 | A-C(O)Cl | BrMg-$B^2$ | A-C(O)-$B^2$ |
| 2 | A-$CR^2R^{2a}$C(O)Cl | BrMg-$B^2$ | A-$CR^{10}R^{10a}$C(O)-$B^2$ |
| 3 | A-C(O)Cl | BrMgCr$^{10}$R$^{10a}$-$B^2$ | A-C(O)CR$^{10}$R$^{10a}$-$B^2$ |
| 4 | A-$CR^{10}R^{10a}$C(O)Cl | BrMgCr$^{10}$R$^{10a}$-$B^2$ | A-$CR^{10}R^{10a}$-C(O)$CR^2R^{2a}$-$B^2$ |

The coupling chemistry of Table B can be carried out by a variety of methods. The Grignard reagent required for $B^2$ is prepared from a halogen analog of $B^2$ in dry ether, dimethoxyethane or tetrahydrofuran at 0° C. to the reflux point of the solvent. This Grignard reagent can be reacted directly under very controlled conditions, that is low temeprature (-20° C. or lower) and with a large excess of acid chloride or with catalytic or stoichiometric copper bromide•dimethyl sulfide complex in dimethyl sulfide as a solvent or with a variant thereof. Other methods available include transforming the Grignard reagent to the cadmium reagent and coupling according to the procedure of Carson and Prout (Org. Syn. Col. Vol. 3 (1955) 601) or a coupling mediated by Fe(acac)$_3$ according to Fiandanese et al. (Tetrahedron Lett., (1984) 4805), or a coupling mediated by manganese (II) catalysis (Cahiez and Laboue, Tetrahedron Lett., 33(31), (1992) 4437).

TABLE C

Preparation of ether and thioether linkages between A and B

| Rxn. No. | if A contains: | then the reactive substituent of $B^2$ is: | to give the following product $A-B^1-B^2$: |
|---|---|---|---|
| 1 | A-OH | Br-$B^2$ | A-O-$B^2$ |
| 2 | A-$CR^2R^{2a}$-OH | Br-$B^2$ | A-$CR^{10}R^{10a}$O-$B^2$ |
| 3 | A-OH | Br-$CR^{10}R^{10a}$-$B^2$ | A-O$CR^{10}R^{10a}$-$B^2$ |
| 4 | A-SH | Br-$B^2$ | A-S-$B^2$ |
| 5 | A-$CR^2R^{2a}$-SH | Br-$B^2$ | A-$CR^{10}R^{10a}$S-$B^2$ |
| 6 | A-SH | Br-$CR^{10}R^{10a}$-$B^2$ | A-S$CR^{10}R^{10a}$-$B^2$ |

The ether and thioether linkages of Table C can be prepared by reacting the two components in a polar aprotic solvent such as acetone, dimethylformamide or dimethylsulfoxide in the presence of a base such as potassium carbonate, sodium hydride or potassium t-butoxide at temperature ranging from ambient temperature to the reflux point of the solvent used.

TABLE D

Preparation of —SO— and —SO2— linkages from thioethers of Table 3

| Rxn. No. | if the starting material is: | and it is oxidized with Alumina (wet)/ Oxone (Greenhalgh, Synlett, (1992) 235) the product is: | and it is oxidized with m-chloroperbenzoic acid (Satoh et al., Chem. Lett. (1992) 381), the product is: |
|---|---|---|---|
| 1 | A-S-$B^2$ | A-S(O)-$B^2$ | A-$SO_2$-$B^2$ |
| 2 | A-$CR^{10}R^{10a}$S-$B^2$ | A-$CR^{10}R^{10a}$S(O)-$B^2$ | A-$CR^{10}R^{10a}SO_2$-$B^2$ |
| 3 | A-$SCR^{10}R^{10a}$-$B^2$ | A-S(O)$CR^{10}R^{10a}$-$B^2$ | A-$SO_2CR^{10}R^{10a}$-$B^2$ |

The thioethers of Table C serve as a convenient starting material for the preparation of the sulfoxide and sulfone analogs of Table D. A combination of wet alumina and oxone can provide a reliable reagent for the oxidation of the thioether to the sulfoxide while m-chloroperbenzoic acid oxidation will give the sulfone.

Other features of the invention will become apparent in the course of the following descriptions of exemplary embodiments which are given for illustration fo the invention and are not intended to be limiting thereof.

EXAMPLES

The synthesis of representative compounds according to the invention is described in further detail below with reference to the following specific, but non-limiting examples.

Abbreviations used in the Examples are defined as follows: "°C." for degrees Celsius, "d" for doublet, "dd" for doublet of doublets, "DAST" for diethylaminosulfur trifluoride, "eq" for equivalent or equivalents, "gm" for gram or grams, "mg" for milligram or milligrams, "mL" for milliliter or milliliters, "H" for hydrogen or hydrogens, "hr" for hour or hours, "m" for multiplet, "M" for molar, "min" for minute or minutes, "MHz" for megahertz, "MS" for mass spectroscopy, "nmr" or "NMR" for nuclear magnetic resonance spectroscopy, "t" for triplet, "TLC" for thin layer chromatography.

Example 1

Preparation of (±) methyl 4-(aminoiminomethyl)-beta-[3-(aminoiminomethyl) phenyl]benzene pentanoate bis(trifluoroacetate)

Part A. Sodium methoxide (25% in MeOH, 1.5 mL, 6.8 mmol) was added dropwise to a solution of 3-acetylbenzonitrile (0.987 gm, 6.8 mmol) and 4-cyanobenzaldehyde (0.891 gm, 6.8 mmol) in dry methanol. Within 5 minutes, a precipitate began to form. The mixture was stirred at room temperature for 4 hrs and diluted with methanol. The solids were filtered off, washed with cold methanol and dried to give 3-[3-(4-cyanophenyl)-1-oxo-2-propenyl]benzonitrile as a white solid 1.7 gm (97%). MS: (M+H)$^+$ 259; $^1$H NMR (CDCl$_3$): 7.55 (d, 1H), 7.65 (t, 1H), 7.75 (s, 4H), 7.85 (m, 2H), 8.25 (d, 1H), 8.30 (s, 1H).

Part B. 3-[3-(4-cyanophenyl)-1-oxo-2-propenyl] benzonitrile (2 gm, 7.75 mmol) was suspended in dry toluene and methyl (triphenylphosphoranylidene)acetate (2.59 gm, 7.75 mmol) added. The mixture was then heated at 100° C. for 24 hours, cooled and the solvent removed under vacuum. The residue was chromatographed on silica gel eluting ethyl acetate:hexanes (25:75, v:v) to give methyl 3-(3-cyanophenyl)-5-(4-cyanophenyl)-2,4-pentadienoate as an oil 2.1 gm (87%). MS: (M+H)$^+$ 315; $^1$H NMR (CDCl$_3$): 3.60 (s, 3H), 3.80 (s, 3H), 5.90 (s, 1H), 6.23 (m, 2H), 6.45 (d, 1H), 7.15 (d, 1H), 7.55 (m, 16H), 8.60 (d, 1H).

Part C. The methyl 3-(3-cyanophenyl)-5-(4-cyanophenyl)-2,4-pentadienoate (5) (0.328 gm, 1.04 mmol) was dissolved in ethyl acetate/THF (1:1) and was degassed with N$_2$. A catalytic amount of 10% Pd on carbon was added and the flask was placed on a Parr shaker for 1 hour at 45 p.s.i. The contents of the flask are filtered through Celite and the filtrate was concentrated under vacuum. The residue was chromatographed on silica gel eluting ethyl acetate:hexanes (25:75, v:v) to give methyl 4-(cyano)-beta-[3-(cyano) phenyl]benzene pentanoate as an oil 0.190 gm (57%). MS: (M+NH$_4$)$^+$ 336; $^1$H NMR (CDCl$_3$): 1.95 (m, 1H), 2.05 (m, 1H), 2.55 (m, 2H), 2.65 (ddd, 2H), 3.15 (m, 1H), 3.60 (s, 3H), 7.20 (d, 2H), 7.45 (d, 2H), 7.50 (s, 1H), 7.55 (m, 3H).

Part D. Hydrogen chloride gas was bubbled through a solution of methyl 4-(cyano)-beta-[3-(cyano)phenyl] benzene pentanoate (0.058 gm, 0.185 mmol) dissolved in 10 mL ethanol under a nitrogen atmosphere and cooled to 0° C.

in an ice bath for 15 minutes. The reaction flask was stoppered and allowed to warm to ambient temperature. The reaction mixture was stirred for 24 hrs and was concentrated in vacuo to give a semisolid residue. The crude imidate was taken up in 10 mLs ethanol and the ammonium carbonate (0.142 gm, 1.48 mmol) was added. The reaction flask was stoppered and stirred at ambient temperature for 28 hrs, then was concetrated in vacuo to give the crude product as a solid residue. The title compound was isolated after HPLC purification on a Vydec C-18 column solvent A (acetonitrile:water:TFA 80:20:0.2) solvent B (water:TFA 99.8:0.2) using a gradient, ($R_f$=21 min), as a white solid 0.051 gm (78%), mp >200° C., MS: (M+H)$^+$ 353; $^1$H NMR (DMSO-d$_6$): 2.0 (m, 2H), 2.5 (m, 2H), 2.7 (dd, 1H), 2.85 (dd, 1H), 3.15 (m, 1H), 3.50 (s, 3H), 7.40 (d, 2H), 7.55 (m, 2H), 7.75 (m, 4H), 9.1 (d, 4H), 9.25(d, 4H).

Example 2

Preparation of methyl 4-(aminoiminomethyl)-beta-[3-(aminoiminomethyl)phenyl]benzene pentanoate bis(trifluoroacetate)

Part A. The enantiomers of methyl 4-(cyano)-beta-[3-(cyano)phenyl]benzene pentanoate of Example 1 Part C, were separated via chiral HPLC (COLUMN: Chiralcel OK; Eluent: 5% H$_2$O, 95% methanol; Flowrate: 1 mL/min) to afford 0.059 gm of Isomer #1 ($R_f$=12 min.) and 0.058 gm of Isomer #2 ($R_f$=14 min.).

Isomer #1

MS: (M+NH$_4$)$^+$ 336; $^1$H NMR (CDCl$_3$): 1.95 (m, 1H), 2.05 (m, 1H), 2.55 (m, 2H), 2.65 (ddd, 2H), 3.15 (m, 1H), 3.60 (s, 3H), 7.20 (d, 2H), 7.45 (d, 2H), 7.50 (s, 1H), 7.55 (m, 3H).

Isomer #2

MS: (M+NH$_4$)$^+$ 336; $^1$H NMR (CDCl$_3$): 1.95 (m, 1H), 2.05 (m, 1H), 2.55 (m, 2H), 2.65 (ddd, 2H), 3.15 (m, 1H), 3.60 (s, 3H), 7.20 (d, 2H), 7.45 (d, 2H), 7.50 (s, 1H), 7.55 (m, 3H).

Part B. Employing the method of Example 1 Part D, 4-(cyano)-beta-[3-(cyano)phenyl]benzene pentanoate Isomer #1 (0.059 gm, 0.185 mmol) was converted to the title compound 0.048 gm (73%). mp >200° C., MS: (M+H)$^+$ 353; $^1$H NMR (DMSO-d$_6$): 2.0 (m, 2H), 2.5 (m, 2H), 2.7 (dd, 1H), 2.85 (dd, 1H), 3.15 (m, 1H), 3.50 (s, 3H), 7.40 (d, 2H), 7.55 (m, 2H), 7.75 (m, 4H), 9.1 (d, 4H), 9.25(d, 4H); Optical rotation: 0°.

Example 3

Preparation of methyl 4-(aminoiminomethyl)-beta-[3-(aminoiminomethyl)phenyl]benzene pentanoate bis(trifluoroacetate)

Employing the method of Example 1 Part D, 4-(cyano)-beta-[3-(cyano)phenyl]benzene pentanoate Isomer #2 (0.059 gm, 0.185 mmol) was converted to the title compound 0.051 gm (78%). mp >200° C. (dec), MS (M+H)$^+$ 353, $^1$H NMR (DMSO-d$_6$): 2.0 (m, 2H), 2.5 (m, 2H), 2.71 (dd, 1H), 2.85 (dd, 1H), 3.15 (m, 1H), 3.50 (s, 3H), 7.40 (d, 2H), 7.55 (m, 2H), 7.75 (m, 4H), 9.1 (d, 4H), 9.25 (d, 4H); Optical rotation: 0°. C,H,N: Calc.: C 49.66, H 4.51, N 9.65 Found: C 49.32, H 4.39, N 9.48.

Example 4

Preparation of (±)-methyl 4-(aminocarbonyl)-beta-[3-(aminoiminomethyl)phenyl]benzene pentanoate mono(trifluoroacetate)

Part A. 2,4-dimethoxybenzylamine hydrochloride (6.78 gm, 33.3 mmol) was dissolved in dry DMF under N$_2$. 4-carboxybenzaldehyde (5 gm, 33.3 mmol) was added, followed by 1-(3-dimethylaminopropyl)-3-ethylcarbodiimide hydrochloride (7 gm, 36.6 mmol) and 4-dimethylaminopyridine (4 gm, 33.3 mmol). The resulting solution was stirred at room temperature for 24 hrs. and quenched in 1 N HCl. After extracting with ethyl acetate, the organic layer was washed with water (3×'s) and brine, dried over MgSO$_4$ and concentrated. The residue was chromatographed on silica gel eluting ethyl acetate:toluene (20:80, v:v) to give 4-(N-2,4-dimethoxybenzyl)carboxamide) benzaldehyde as an oil 4.3 gm (43%). MS (M+H)$^+$ 300, $^1$H NMR (CDCl$_3$): 3.80 (s, 3H), 3.85 (s, 3H), 4.6 (d, 2H), 6.45 (m, 2H), 7.2 (m, 1H), 7.90 (s, 4H), 10.0 (s, 1H).

Part B. Basic alumina (11 gm) was added to a solution of 3-acetylbenzonitrile (0.200 gm, 1.52 mmol) and 4-(N-2,4-dimethoxybenzyl)carboxamide)benzaldehyde (0.908 gm, 3.04 mmol) in a small amount of methylene chloride. The viscous solution was vigorously stirred under N$_2$ for 48 hours. The reaction was diluted with 200 mL of methylene chloride and the solids collected by filtration to give 3-[3-(4-(N-2,4-dimethoxybenzyl)benzamide)-1-oxo-2-propenyl] benzonitrile as a white solid, 0.338 gm (52%) MS: (M+H)$^+$ 427; $^1$H NMR (CDCl$_3$): 3.80 (s, 3H), 3.85 (s, 3H), 4.60 (d, 2H), 6.45 (m, 2H), 6.65 (t, 1H), 7.25 (d, 1H), 7.7 (m, 6H), 8.25 (d, 1H), 8.30 (s, 1H).

Part C. 3-[3-(4-(N-2,4-dimethoxybenzyl)benzamide)-1-oxo-2-propenyl]benzonitrile (0.318 gm, 0.746 mmol) was suspended in dry toluene and methyl (triphenylphosphoranylidene)acetate (0.373 gm, 1.1 mmol) added. The resulting mixture was heated at 110° C. for 24 hours, cooled to room temperature and the solvent removed under vacuum. The residue was chromatographed on silica gel eluting ethyl acetate:toluene (v:v, 20:80) to afford a mixture of E and Z isomers of methyl 3-(3-cyanophenyl)-5-(4-(N-2,4-dimethoxybenzyl)benzamide)-2,4-pentadienoate as an oil 0.210 gm (58%). MS: (M+H)$^+$ 483; 1H NMR (CDCl3): 375–3.9 (m, 9H), 4.58 (m,2H), 6.2–6.6 (m, 3H), 7.05–7.8 (m, 12H).

Part D. Methyl 3-(3-cyanophenyl)-5-(4-(N-2,4-dimethoxybenzyl)benzamide)-2,4-pentadienoate (0.165 gm, 0.342 mmol) was dissolved in methanol and degassed with N$_2$. A catalytic amount of 10% Pd on carbon was added and the solution placed on a Parr shaker for 45 minutes at 45 p.s.i. The solution was then filtered through Celite and the solvent removed under vacuum to afford methyl 3-(3-cyanophenyl)-5-(4-(N-2,4-dimethoxybenzyl)benzamide) pentanoate as an oil 0.140 gm (84%). MS: (M+H)$^+$ 487; $^1$H NMR (CDCl$_3$): 1.95 (m, 2H), 2.45 (t, 2H), 2.6(m, 2H), 3.15 (m, 1H), 3.59 (s, 3H), 3.80 (s, 3H), 3.85 (s, 3H), 4.55 (d, 2H), 6.45 (d, 2H), 6.55 (t, 1H), 7.10 (d, 2H), 7.25 (d, 1H), 7.55 (m, 6H).

Part E. A solution of methyl 3-(3-cyanophenyl)-5-(4-(N-2,4-dimethoxybenzyl)benzamide)pentanoate (0.140 gm, 0.288 mmol) in acetonitrile was added to a solution of ceric ammonium sulfate (0.686 gm, 1.152 mmol) in water. The resulting solution was heated at 60° C. for 4 hours, cooled to room temperature and poured into water. The water was extracted with ethyl acetate (2×'s) and the organic layer washed with water and brine and dried over magnesium sulfate. After removing the solvent, the residue was chromatographed on silica gel (90% ethyl acetate/toluene) to give methyl 3-(3-cyanophenyl)-5-(4-benzamide)pentanoate as an oil 0.053 gm (55%). MS: (M+NH$_4$)$^+$ 354; $^1$H NMR (DMSO-d$_6$): 1.95 (m, 2H), 2.4 (m, 2H), 2.65 (dd, 1H), 2.8 (dd, 1H), 3.05 (m, 1H), 3.45 (s, 3H), 7.19 (d, 2H), 7.25 (s (broad), 1H), 7.56 (m, 6H), 7.90 (s (broad), 1H).

Part F. Employing the method of Example 1 Part D but using methyl 3-(3-cyanophenyl)-5-(4-benzamide)

pentanoate (0.050 gm, 0.148 mmol) the title compound was isolated after HPLC purification on a Vydec C-18 column solvent A (acetonitrile:water:TFA 80:20:0.2) solvent B (water:TFA 99.8:0.2) using a gradient, ($R_f$=16 minutes) as a solid 0.030 gm (57%). Mp >200° C. MS: (M+H)$^+$ 354; $^1$H NMR (DMSO-d$_6$): 1.95 (m, 2H), 2.45 (m, 2H), 2.7 (dd, 1H), 2.85(dd,1H), 3.15 (m, 1H), 3.50 (s, 3H), 7.20 (d, 2H), 7.25 (s, 1H), 7.6 (m, 8H), 7.85 (s, 1H), 8.95 (s (broad), 2H), 9.30 (s (broad), 2H).

Example 5

Preparation of (±)-methyl beta-[3-(aminoiminomethyl)phenyl][1,1'-biphenyl]-4-pentanoate mono (trifluoroacetate)

Part A. Employing methods similar to Example 1 Part A, but using 3-nitrile acetophenone (0.798 gm, 5.5 mmol) and 4-biphenylcarboxaldehyde (1.0 gm, 5.5 mmol) 3-[3-(1,1'-biphenyl)-1-oxo-2-propenyl]benzonitrile was prepared as a white powder 0.85 gm (50%). MS 310(M+H)$^+$ $^1$H NMR (CDCl$_3$): 7.4–7.9 (m, 13H), 8.2–8.3(m, 2H).

Part B. Employing methods similar to Example 1 Part B, but using 3-[3-(1,1'-biphenyl)-1-oxo-2-propenyl] benzonitrile (0.36 gm, 1.17 mmol) and carbomethoxymethylene triphenylphosphorane (0.391 gm, 1.17 mmol) methyl 3-(3-cyanophenyl)-5-(1,1'-biphenyl)-2,4-pentadienoate was isolated after flash chromatography on silica gel eluting with methylene chloride:hexane (v:v, 80:20) as an oily solid 0.178 gm (42%) MS 366(M+H)$^+$ $^1$H NMR (CDCl$_3$): 8.6(d, 1H), 7.4–7.8(m, 13H), 6.5(d, 1H), 5.8(s, 1H), 3.8(s, 3H).

Part C. Employing methods similar to Example 1 Part C, but using methyl 3-(3-cyanophenyl)-5-(1,1'-biphenyl)-2,4-pentadienoate (0.17 gm, 0.46 mmol), methyl 3-(3-cyanophenyl)-5-(1,1'-biphenyl)pentanoate was prepared as an oil 0.11 gm (100%). MS 387(M+NH4)$^+$. $^1$H NMR (CDCl$_3$): 7.4–7.6(m, 11H), 7.2(d, 2H), 3.6(s, 3H), 3.2(m, 1H), 2.5–2.7(m, 4H), 2.0(m, 2H).

Part D. Employing methods similar to Example 1 Part D, but using methyl 3-(3-cyanophenyl)-5-(1,1'-biphenyl) pentanoate (0.118 gm,0.32 mmol) the title compound was isolated after HPLC purification on Vydac C-18 column eluting with Solvent A (acetonitrile:water:TFA 80:20:0.2) and solvent B (water:TFA 99.8:2) using a gradient, as a white crystalline powder 0.087 gm (70%) Mp 182° C. MS 387(M+H)$^+$ HRMS calc 387.2073, found 387.2079 $^1$H NMR (DMSO-d6): 9.3(s, 2H), 9.0(s,2H), 7.6–7.8(m, 8H), 7.5(t, 2H), 7.4(t, 1H), 7.2(d, 2H), 3.5(s, 3H), 3.2(m, 1H), 2.7–2.8(m, 2H), 2.2(m, 2H), 2.0(m, 2H).

Example 6

Preparation of 4-(aminoiminomethyl)-beta-[3-(aminoiminomethyl)phenyl]benzenepentanoic acid dihydrochloride Methyl 4-(aminoiminomethyl)-beta-[3-(aminoiminomethyl) phenyl]benzene pentanoate bis (trifluoroacetate) (0.030 gm, 0.08 mmol) was dissolved in 0.5 mL of 6 N HCl under N$_2$ and stirred at room temperature for 48 hrs. The solution was concentrated to give the title compound as a white solid 0.018 gm (66%). Mp >200° C. (dec); MS: (M+H)$^+$ 339; $^1$H NMR (DMSO-d$_6$): 2.0 (m, 2H), 2.5 (m, 2H), 2.7 (dd, 1H), 2.85 (dd, 1H), 3.15(m, 1H), 7.40 (d, 2H), 7.55 (m, 2H), 7.75 (m, 4H), 9.1 (d, 4H), 9.25 (d, 4H).

Example 7

Preparation of (±) 1-methylethyl 4-(aminoiminomethyl)-beta-[3aminoiminomethyl) phenyl]benzene pentanoate bis(trifluoroacetate)

Part A. Methyl 4-(cyano)-beta-[3-(cyano)phenyl]benzene pentanoate (0.250 gm, 0.786 mmol) was dissolved in methanol and LiOH (0.056 gm, 2.3 mmol) in 1 mL of water was added. The solution was stirred at room temperature for 2 hrs. and extracted with ethyl acetate. The resultant aqueous layer was made acidic with 1 N HCl and extracted with ethyl acetate. The organic phase was dried over MgSO$_4$ and concentrated to give 4-(cyano)-beta-[3-(cyano)phenyl] benzene pentanoic acid as an oil 0.138 gm (58%). $^1$H NMR (DMSO-d$_6$): 1.95 (m, 2H), 2.3 (m, 3H), 2.70 (dd, 1H), 3.05 (m, 1H), 7.3 (d, 2H), 7.5 (t, 1H), 7.60 (d, 1H), 7.7 (m, 3H), 12.10 (s, 1H).

Part B. 4-(cyano)-beta-[3-(cyano)phenyl]benzene pentanoic acid (0.111 gm, 0.37 mmol) was dissolved in 2-propanol and treated with anhydrous HCl for 2 minutes. The resulting solution was stirred at room temperature overnight and then concentrated. The residue was dissolved in fresh 2-propanol and ammonium carbonate (0.284 gm, 2.9 mmol) was added. The solution was stirred at room temperature for 24 hrs., concentrated and the title compound was isolated after HPLC purification on a Vydec C-18 column solvent A (acetonitrile:water:TFA 80:20:0.2) solvent B (water:TFA 99.8:0.2) using a gradient, ($R_f$=18 min), as a white powder 0.015 gm. Mp >200° C. (dec); MS: (M+H)$^+$ 381; $^1$H NMR (DMSO-d$_6$): 1.15 (dd, 6H), 2.0 (m, 2H), 2.5 (m, 2H), 2.7 (dd, 1H), 2.85 (dd, 1H), 3.15 (m, 1H), 4.80 (septet, 1H), 7.40 (d, 2H), 7.55(m, 2H), 7.75 (m, 4H), 9.1 (d, 4H), 9.25 (d, 4H).

Example 8

Preparation of (±)-ethyl 4-(aminoiminomethyl)-beta-[3-(aminoiminomethyl)phenyl]benzene pentanoate bis(trifluoroacetate)

Employing a method similar to Example 7 Part B, using ethanol instead of 2-propanol, the title compound was prepared as a white solid 0.015 gm (7%) after HPLC purification on a Vydec C-18 column, solvent A (acetonitrile:water:TFA 80:20:0.2) solvent B (water:TFA 99.8:0.2) using a gradient ($R_f$=17 min.). Mp >200° C.; MS: (M+H)$^+$ 367; $^1$H NMR (DMSO-d$_6$): 1.05 (t, 3H), 2.0 (m, 2H), 2.5 (m, 2H), 2.7 (dd, 1H), 2.85 (dd, 1H), 3.15 (m, 1H), 3.50 (s, 3H), 3.95 (m, 2H), 7.40 (d, 2H), 7.55 (m, 2H), 7.75 (m, 4H), 9.1 (d, 4H), 9.25(d, 4H).

Example 9

Preparation of (±)-4-(aminoiminomethyl)-beta-[3-(aminoiminomethyl)phenyl]-N-(2-phenylethyl) benzenepentanamide bis(trifluoroacetate)

Part A. 4-(cyano)-beta-[3-(cyano)phenyl]benzene pentanoic acid (0.150 gm, 0.49 mmol) was dissolved in dry DMF and phenethyl amine (0.065 gm, 0.54 mmol), 1-(3-dimethylaminopropyl)-3-ethylcarbodiimide hydrochloride (0.140 gm, 0.74 mmol) and 4-dimethylaminopyridine (0.150 gm, 1.2 mmol) were added. The resulting solution was stirred at room temperature for 48 hrs., quenched in 1 N HCl and extracted with ethyl acetate. The organic phase was washed with 1 N HCl, water and brine and dried over MgSO$_4$. After removal of the solvent, the residue was chromatographed on silica gel eluting ethyl acetate:toluene (30:70, v:v) to give 4-(cyano)-beta-[3-(cyano)phenyl]-N-(2-phenylethyl)benzenepentanamide as an oil 0.100 gm (50%). MS: (M+H)$^+$ 408; $^1$H NMR (CDCl$_3$): 1.9 (m,1H), 2.35 (dd, 1H), 2.45 (m, 2H), 2.7(m, 3H), 3.25(m, 1H), 3.45 (m, 3H), 7.0 (d, 2H), 7.2 (m, 6H), 7.45 (m, 3H), 7.55 (m, 3H).

Part B. 4-(cyano)-beta-[3-(cyano)phenyl]-N-(2-phenylethyl)benzenepentanamide (0.100 gm, 0.245 mmol)

was dissolved in methanol and brought to 0° C. Anhydrous HCl was added for 15 minutes and the resulting solution was stirred overnight at room temperature. The solvent was removed under vacuum and the residue dissolved in fresh methanol. Ammonium carbonate (0.188 gm, 1.9 mmol) was added and the solution stirred at room temperature for 24 hrs. and concentrated. the title compound was isolated after HPLC purification on a Vydec C-18 column solvent A (acetonitrile:water:TFA 80:20:0.2) solvent B (water:TFA 99.8:0.2) using a gradient ($R_t$=18 min), as a white solid 0.060 gm. Mp >200° C.; MS: 221(M+2H)$^{2+}$; $^1$H NMR (DMSO-d$_6$): 1.95 (m, 2H), 2.5(m, 5H), 3.2 (m, 4H), 7.05 (d, 2H), 7.2 (m, 4H), 7.40 (d, 2H), 7.55 (d, 2H), 7.7 (m, 4H), 9.1 (d, 4H), 9.25 (d, 4H).

Example 10

Preparation of (±)-methyl 4-amino-beta-[3-(aminoiminomethyl)phenyl]benzenepentanoate mono(trifluoroacetate)

Part A. Sodium methoxide (25% in MeOH, 1.5 mL, 6.8 mmol) was added dropwise to a solution of 3-acetylbenzonitrile (987 gm, 6.8 mmol) and 4-nitrobenzaldehyde (1 gm, 6.8 mmol) in dry methanol. Within 5 minutes, a precipitate begins to appear. The mixture was stirred at room temperature for 4 hours and diluted with methanol. The solids were filtered off, washed with cold methanol and dried to give 3-[3-(4-nitrophenyl)-1-oxo-2-propenyl]benzonitrile as a white solid 1.7 gm (97%) MS: 279(M+H)$^+$; $^1$H NMR (CDCl$_3$): 7.60 (d, 1H), 7.70 (t, 1H), 7.85 (m, 4H), 8.25 (m, 4H)

Part B. 3-[3-(4-nitrophenyl)-1-oxo-2-propenyl] benzonitrile (0.500 gm, 1.79 mmol) was suspended in toluene and methyl (triphenylphosphoranylidene)acetate (0.600 gm, 1.79 mmol) was added. The suspension was heated to reflux (at which point the solution becomes homogeneous) for 5 hrs. The reaction was cooled to room temperature and the solvent removed under vacuum. The residue was chromatographed on silica gel (20% ethyl acetate/toluene) to afford methyl 3-(3-cyanophenyl)-5-(4-nitrophenyl)-2,4-pentadienoate 0.441 gm (74%) as a mixture of the E/Z isomers. MS: 335(M+H)$^+$; $^1$H NMR (CDCl$_3$): 3.6 (s, 3H), 3.8 (s, 3H), 5.9 (s, 1H), 6.25 (m, 2H), 6.6 (d, 1H), 7.15 (m, 2H), 7.6 (m, 11H), 8.2 (d, 4H), 8.65 (d, 1H).

Part C. Methyl 3-(3-cyanophenyl)-5-(4-nitrophenyl)-2,4-pentadienoate (0.441 gm, 1.32 mmol) was dissolved in THF and degassed with N$_2$. A catalytic amount of 10% Pd/C was added and the solution placed on a Parr shaker at 45 p.s.i. for 1 hour. After filtering through Celite, the solvent was removed under vacuum and the residue chromatographed on silica gel (10% ethyl acetate/methylene chloride) to yield methyl 3-(3-cyanophenyl)-5-(4-aminophenyl)pentanoate 0.220 gm (54%) of the product. MS: 309(M+H)$^+$; $^1$H NMR (CDCl$_3$): 1.9 (m, 2H), 2.35 (t, 2H), 2.6 (m, 2H), 3.15 (m, 1H), 3.55 (3H), 6. 60 (d, 2H), 6.85 (d, 2H), 7.5 (m, 4H).

Part D. Employing methods similiar to Example 1 Part D, but using methyl 3-(3-cyanophenyl)-5-(4-aminophenyl) pentanoate (0.220 gm, 0.71 mmol) the title compound was isolated after HPLC purification on a Vydec C-18 column solvent A (acetonitrile:water:TFA 80:20:0.2) solvent B (water:TFA 99.8:0.2) using a gradient; ($R_t$=13 min.) as a white solid 0.105 gm (45%). Mp >200° C.; MS: 326(M+H)$^+$; $^1$H NMR (DMSO-d$_6$): 2.0 (m, 2H), 2.5(m, 2H), 2.7(dd, 1H), 2.85 (dd, 1H), 3.15 (m, 1H), 3.50 (s, 3H), 7.1 (q, 4H), 7.55 (m, 2H), 7.7 (m, 2H), 9.3 (d (broad), 4H).

Example 11

Preparation of (±)-methyl beta-[3-(aminoiminomethyl)phenyl]-4-[(phenylsulfonyl) amino]benzenepentanoate mono(trifluoroacetate)

Part A. methyl 3-(3-cyanophenyl)-5-(4-aminophenyl) pentanoate (0.100 gm, 0.325 mmol) was dissolved in diox-ane and 0.5 mL of 1 N NaOH was added, followed by benzenesulfonyl chloride. The solution was stirred for 1 hour, quenched in 1 N HCl and extracted with ethyl acetate. The organic layer was washed with water and brine and dried over MgSO$_4$. The solvent was removed under vacuum and the residue was chromatographed on silica gel eluting ethyl acetate:toluene (20:80, v:v) to give methyl beta-[3-(cyano)phenyl]-4-[(phenylsulfonyl)amino] benzenepentanoate as an oil 0.060 gm (41%). MS: (M+NH$_4$)$^+$ 466; $^1$H NMR (CDCl$_3$): 1.9 (m, 2H), 2.35 (m, 2H), 2.6 (m, 2H), 3.15 (m, 1H), 3.55 (s, 3H), 6.95 (s, 4H), 7.45 (m, 5H), 7.55 (m, 2H), 7.75 (d, 2H).

Part B. Employing methods similar to Example 1 Part D, but using methyl beta-[3-(cyano)phenyl]-4-[(phenylsulfonyl)amino]benzenepentanoate (0.060 gm, 0.135 mmol) the title compound was isolated after HPLC purification on a Vydec C-18 column solvent A (acetonitrile:water:TFA 80:20:0.2) solvent B (water:TFA 99.8:0.2) using a gradient ($R_t$=25 min), as a white powder 0.015 gm (24%). Mp >200° C.; MS: (M+H)$^+$ 366; $^1$H NMR (DMSO-d$_6$): 1.85 (m, 2H), 2.3 (m, 2H), 2.65 (dd, 1H), 2.9 (dd, 1H), 3.05 (m, 1H), 3.5 (s, 3H), 6.95 (s, 4H), 7.6 (m, 9H), 8.9 (s (broad), 2H), 9.25 (s (broad), 2H), 10.1 (s, 1H).

Example 12

Preparation of (±)-methyl beta-[3-(aminoiminomethyl)phenyl]-4-[(methylsulfonyl) amino]benzene pentanoate mono(trifluoroacetate)

Part A. Methyl 3-(3-cyanophenyl)-5-(4-aminophenyl) pentanoate (0.100 gm, 0.325 mmol) was dissolved in 3 mL benzene and treated with methane sulfuric anhydride (0.062 gm, 0.357 mmol). The solution was stirred for 0.5 hr. and the solvent was removed under vacuum. The residue was chromatographed on silca gel eluting(ethyl acetate:methylene chloride:toluene (v:v:v,20:40:40) to give methyl beta-[3-(cyano)phenyl]-4-[(methylsulfonyl)amino] benzenepentanoate as an oil 0.038 gm (30%) MS; $^1$H NMR (CDCl$_3$): 1.9 (m, 2H), 2.4 (t, 2H), 2.6 (m, 2H), 3.0 (s, 3H), 3.15 (m, 1H), 3.6 (s, 3H), 6.25 (s (broad), 1H), 7.1 (q, 4H), 7.5 (m, 4H).

Part B. Employing methods similar to Example 1 Part D, but using methyl beta-[3-(cyano)phenyl]-4-[(methylsulfonyl)amino]benzenepentanoate (0.038 gm, 0.098 mmol) the title compound was isolated after HPLC purification on a Vydec C-18 column solvent A (acetonitrile:water:TFA 80:20:0.2) solvent B (water:TFA 99.8:0.2) using a gradient (R$_t$=21 min),as a white solid 0.030 gm (76%). Mp >200° C.; MS: (M+H)$^+$ 404; $^1$H NMR (DMSO-d$_6$): 1.95 (m, 2H), 2.4 (m, 2H), 2.7 (dd, 1H), 2.85 (dd, 1H), 2.95 (s, 3H), 3.55 (s, 3H), 7.05 (q, 4H), 7.65 (m, 4H), 8.9 (s (broad), 2H), 9.25 (s (broad), 2H), 9.55 (s, 1H).

Example 13

Preparation of (±)-methyl 4-[(aminoiminomethyl) amino]-beta-[3-(aminoiminomethyl)phenyl] benzenepentanoate bis(trifluoroacetate)

Methyl 3-(3-cyanophenyl)-5-(4-aminophenyl)pentanoate (0.10 gm, 0.325 mmol) was dissolved in 5 mL of pyridine and 3,5-dimethylpyrazole-1-carboxamidine nitrate (0.098 gm, 0.048 mmol) was added. The solution was heated at 80° C. overnight, cooled and partitioned between ethylacetate and water. The organic layer was washed with a small amount of water and dried over MgSO$_4$. After removing the solvent, the residue (0.150 gm, 0.428 mmol) was converted to the amidine employing methods similar to Example 1 Part D. The title compound was isolated after HPLC purification on a Vydec C-18 column solvent A (acetonitrile:water:TFA 80:20:0.2) solvent B (water:TFA 99.8:0.2) using a gradient ($R_f$=16 min), as a solid 0.080 gm (51%). MS: (M+H)$^+$ 368; $^1$H NMR (DMSO-d$_6$): 2.0 (m, 2H), 2.5 (m, 2H), 2.7 (dd, 1H), 2.85 (dd, 1H), 3.15 (m, 1H), 3.50 (s, 3H), 7.15 (q, 4H), 7.35 (s (broad), 4H), 7.65 (m, 4H), 9.05 (s (broad), 2H), 9.25 (s (broad), 2H), 9.65 (s, 1H).

Example 14

Preparation of (±)-methyl 4-(aminoiminomethyl)-beta-[3-[(aminoiminomethyl)amino]phenyl] benzenepentanoate bis(trifluoroacetate)

Part A. Employing methods silimar to Example 1 Part A, but using 3-acetylnitrobenzene (1.25 gm, 7.67 mmol) and 4-cyanobenzaldehyde (1 gm, 7.6 mmol), 3-[3-(4-cyanophenyl)-1-oxo-2-propenyl]nitrobenzene was prepared as a solid 1.7 gm (80%). Mp >210° C.; MS: (M+H)$^+$ 279; $^1$H NMR (CDCl$_3$): 7.6 (d, 1H), 7.75 (m, 5H), 7.9 (d, 1H), 8.4 (d, 1H), 8.5 (d, 1H), 8.85 (s, 1H).

Part B. Employing methods silimar to Example 1 Part B, but using 3-[3-(4-cyanophenyl)-1-oxo-2-propenyl] nitrobenzene (1 gm, 3.59 mmol), methyl 3-(3-nitrophenyl)-5-(4-cyanophenyl)-2,4-pentadienoate was prepared as a mixture of the E/Z isomers. The product was purifed by chromatography on silica gel eluting ethyl acetate:toluene (20:80, v:v) to give an oil 0.900 gm (75%). $^1$H NMR (CDCl$_3$): 3.6 (s, 3H), 3.8 (s, 3H), 5.95 (s, 1H), 6.23 (t, 2H), 6.5 (d, 1H), 7.15 (d, 1H), 7.45 (d, 2H), 7.65 (m, 10H), 8.05 (s, 1H), 8.2 (s, 1H), 8.3 (d, 2H), 8.6 (d, 1H).

Part C. Methyl 3-(3-nitrophenyl)-5-(4-cyanophenyl)-2,4-pentadienoate (0.869 gm, 2.6 mmol) was dissolved in THF and degassed with N$_2$. A catalytic amount of 10% Pd/C was added and the solution was placed on a Parr shaker for 45 min. at 45 p.s.i. The solution was filtered through Celite and the solvent was removed under vacuum. The residue was chromatographed on silica gel eluting ethyl acetate:methylene chloride (20:80, v:v) to give methyl 3-(3-aminophenyl)-5-(4-cyanophenyl)pentanoate as an oil 0.512 gm (64%). $^1$H NMR (CDCl$_3$): 1.9 (m, 2H), 2.55 (t, 2H), 3.0 (m, 1H), 3.25 (m, 2H), 3.6 (s, 3H), 6.5 (s, 1H), 6.55 (m, 2H), 7.1 (t, 1H), 7.3 (m, 2H), 7.55 (m, 3H).

Part D. Employing methods similar to Example 13, but using methyl 3-(3-aminophenyl)-5-(4-cyanophenyl) pentanoate (0.170 gm, 0.55 mmol) the title compound was isolated after HPLC purification on a Vydec C-18 column solvent A (acetonitrile:water:TFA 80:20:0.2) solvent B (water:TFA 99.8:0.2) using a gradient ($R_f$=19 min), as an amorphous solid 0.010 gm (5%). MS: (M+2H)$^{2+}$ 184; $^1$H NMR (DMSO-d$_6$): 1.95 (m, 2H), 2.55 (m, 2H), 2.7 (m, 2H), 3.05 (m, 1H), 3.5 (s, 3H), 7.2 (M, 2H), 7.4 (m, 5H), 7.75 (d, 1H), 8.95 (s (broad), 2H), 9.2 (s broad), 2H), 9.7 (s, 1H).

Example 15

Preparation of (±)-methyl 4-[(aminoiminomethyl) amino]-beta-[3-(aminoiminomethyl)phenyl] benzeneheptanoate bis(trifluoroacetate)

Part A. Employing a method similar to Example 1 Part A but using, 3-acetylbenzonitrile (3.7 gm, 28.2 mmol) and 4-nitrocinnamaldehyde (5 gm, 28.2 mmol) 3-[5-(4-nitrophenyl)-1-oxo-2,4-pentadiene]benzonitrile was prepared as a solid 6.5 gm (73%). MS: (M+H)$^+$ 319; $^1$H NMR (CDCl$_3$): 7.15 (m, 3H), 7.65 (m, 4H), 7.85 (d, 1H), 8.25 (m, 4H).

Part B. Employing methods similar to Example 1 Part B, but using 3-[5-(4-nitrophenyl)-1-oxo-2,4-pentadiene] benzonitrile (2 gm, 6.28 mmol), the methyl 3-(3-cyanophenyl)-7-(4-nitrophenyl)-2,4,6-heptatrienoate was prepared as an oil 0.550 gm (25%). MS: (M+NH$_4$)$^+$ 378; $^1$H NMR (CDCl$_3$): 3.8 (s, 3H), 5.8 (s, 1H), 6.3 (dd, 1H), 6.65 (d, 1H), 7.15 (dd, 1H), 7.6 (m, 6H), 8.1 (d, 1H), 8.2 (d, 2H).

Part C. Employing methods similar to Example 1 Part C, but using methyl 3-(3-cyanophenyl)-7-(4-nitrophenyl)-2,4,6-heptatrienoate (0.363 gm, 1 mmol), methyl 3-(3-cyanophenyl)-7-(4-aminophenyl)-heptanoate was prepared as an oil 0.296 gm (87%). MS: (M+H)$^+$ 337; $^1$H NMR (CDCl$_3$): 1.15 (m, 1H), 1.65 (m, 4H), 2.55 (m, 4H), 3.1 (m, 1H), 3.6 (s, 3H), 6.6 (d, 2H), 6.9 (d, 2H), 7.45 (m, 4H).

Part D. Employing methods similar to Example 13, but using methyl 3-(3-cyanophenyl)-7-(4-aminophenyl)-heptanoate (0.200 gm, 0.595 mmol) the title compound was isolated after HPLC purification on a Vydec C-18 column solvent A (acetonitrile:water:TFA 80:20:0.2) solvent B (water:TFA 99.8:0.2) using a gradient, ($R_f$=20 min), as a white solid 0.110 gm (46%). MS:(M+H)$^+$ 396; $^1$H NMR (DMSO-d$_6$): 1.2 (m, 1H), 2.55 (m, 2H), 2.65 (m, 2H), 2.5 (m, 2H), 2.65 (dd, 1H), 2.75 (dd, 1H), 3.1 (m, 1H), 3.5 (s, 3H), 7.1 (d, 2H), 7.2 (d, 2H), 7.4 (s (broad), 4H), 7.55 (t, 1H), 7.6 (d, 1H), 7.65 (m, 2H), 9.05 (s (broad), 2H), 9.25 (s (broad), 2H), 9.65 (s, 1H).

Example 16

Preparation of (±)-methyl 4-amino-beta-[3-(aminoiminomethyl)phenyl]benzeneheptanoate bis (trifluoroacetate)

Employing methods similar to Example 1 Part A, but using methyl 3-(3-cyanophenyl)-7-(4-aminophenyl)-heptanoate (0.160 gm, 0.476 mmol) the title compound was isolated after HPLC purification on a Vydec C-18 column solvent A (acetonitrile:water:TFA 80:20:0.2) solvent B (water:TFA 99.8:0.2) using a gradient; ($R_f$=18 min), as a white solid 0.070 gm (42%). MS:(M+H)$^+$ 354; $^1$H NMR (DMSO-d$_6$): 1.1 (m, 2H), 1.45 (m, 2H), 1.65 (m, 2H), 2.45 (m, 2H), 2.65 (dd, 1H), 2.75 (dd, 1H), 3.1 (m, 1H), 3.5 (s, 3H), 6.9 (d, 2H), 7.05 (d, 2H), 7.6 (m, 4H), 9.0 (s (broad), 4H), 9.25 (s (broad), 4H).

Example 17

Preparation of (±)-methyl 3-(aminoiminomethyl)-beta-[3-(aminoiminomethyl)phenyl] benzenepentanoate bis(trifluoroacetate)

Part A. 3-acetylbenzonitrile (1 gm, 6.8 mmol) and 3-cyanobenzaldehyde (2.76 gm, 17 mmol) are dissolved in a minimal amount of methyl chloride and 20 g of basic alumina was added. The resulting slurry was vigorously stirred at room temperature for 72 hrs. The slurry was filtered and the filter cake thoroughly washed with methylene chloride. The solvent was removed under vacuum and the residue chromatographed on silica gel eluting methylene chloride to give 3-[3-(3-cyanophenyl)-1-oxo-2-propenyl] benzonitrile as a solid 0.285 gm (15%). MS: (M+H)$^+$ 259; $^1$H NMR (CDCl$_3$): 7.6 (t, 2H), 7.7 (m, 2H), 7.85 (m, 3H), 7.95 (s, 1H), 8.25 (d, 1H), 8.35 (s, 1H).

Part B. Employing methods similar to Example 1 Part B, but using 3-[3-(3-cyanophenyl)-1-oxo-2-propenyl] benzonitrile (0.280 gm, 1.08 mmol), methyl 3-(3-cyanophenyl)-5-(3-cyanophenyl)-2,4-pentadienoate as a mixture of the E/Z isomers was prepared as an oil 0.297 gm (87%). MS: (M+NH$_4$)$^+$ 332; $^1$H NMR (CDCl$_3$): 3.60 (s, 3H), 3.80 (s, 3H), 5.85 (s, 1H), 6.23 (t, 2H), 6.45 (d, 1H), 7.15 (d, 1H), 7.55 (m, 16H), 8.60 (d, 1H).

Part C. Employing methods similar to Example 1, Part C, but using methyl 3-(3-cyanophenyl)-5-(3-cyanophenyl)-2,4-pentadienoate (0.297 gm, 0.945 mmol) methyl 3-(3-cyanophenyl)-5-(3-cyanophenyl)pentanoate was prepared as an oil 0.250 gm (83%). MS:(M+NH$_4$)$^+$ 336; $^1$H NMR (CDCl$_3$): 1.9 (m, 2H), 2.45 (m, 2H), 2.65 (m, 2H), 3.15 (m, 1H), 3.6 (s, 3H), 7.5 (m, 8H).

Part D. Employing methods similar to Example 1 Part D, but using methyl 3-(3-cyanophenyl)-5-(3-cyanophenyl) pentanoate (0.250 gm, 0.786 mmol), the title compound was isolated after HPLC purification on a Vydec C-18 column solvent A (acetonitrile:water:TFA 80:20:0.2) solvent B (water:TFA 99.8:0.2) using a gradient, (R$_f$=22 min), as a solid 0.030 gm (11%). MS:(M+H)$^+$ 353; $^1$H NMR (DMSO-d$_6$): 2.0 (m, 2H), 2.5(m, 2H), 2.7 (dd, 1H), 2.85 (dd, 1H), 3.15 (m, 1H), 3.50 (s, 3H), 7.5 (s, 2H), 7.55 (m, 2H), 7.6 (t, 2H), 7.7 (d, 1H), 7.75 (s, 1H), 9.2 (s (v.broad), 6H).

Example 18

Preparation of (±)-methyl beta-[3-(aminoiminomethyl)phenyl]-4-(methoxycarbonyl) benzene pentanoate mono(trifluoroacetate)

Part A. 3-acetylbenzonitrile (1 gm, 6.8 mmol) and methyl 4-formylbenzoate (3.12 gm, 17 mmol) are dissolved in a minimal amount of methyl chloride and 20 g of basic alumina was added. The resulting slurry was vigorously stirred at room temperature for 72 hrs. The slurry was filtered and the filter cake thoroughly washed with methylene chloride. The solvent was removed under vacuum and the residue chromatographed on silica gel eluting methylene chloride to give 3-[3-(methyl 4-benzoate)-1-oxo-2-propenyl]benzonitrile 0.340 gm (20%). $^1$H NMR (CDCl$_3$): 3.95 (s, 3H), 7.55 (d, 1H), 7.7 (m, 3H), 7.85 (t, 2H), 8.1 (d, 2H), 8.25 (d, 1H), 8.3 (s, 1H).

Part B. Employing methods similar to Example 1 Part B, but using 3-[3-(methyl 4-benzoate)-1-oxo-2-propenyl] benzonitrile (0.192 gm, 0.655 mmol) methyl 3-(3-cyanophenyl)-5-(methyl 4-benzoate)-2,4-pentadienoate was prepared as a mixture of E and Z isomers as an oil 0.215 gm (95%). MS:(M+H)$^+$ 348; $^1$H NMR (CDCl$_3$): 3.6–3.9 (m,6H), 7.1–8.0 (m,11H).

Part C. Employing methods similar to Example 1 Part C, but using methyl 3-(3-cyanophenyl)-5-(methyl 4-benzoate)-2,4-pentadienoate (0.200 gm, 0.574 mmol) methyl 3-(3-cyanophenyl)-5-(methyl 4-benzoate)pentanoate was prepared as an oil 0.150 gm (75%). MS:(M+NH$_4$)$^+$ 369; $^1$H NMR (CDCl$_3$): 2.0 (m, 2H), 2.5 (t, 2H), 2.7 (m, 2H), 3.15 (m, 1H), 3.6 (s, 3H), 3.9 (s, 3H), 7.15 (d, 2H), 7.5 (m, 4H), 7.95 (d, 2H).

Part D. Employing methods similar to Example 1 Part D, but using methyl 3-(3-cyanophenyl)-5-(methyl 4-benzoate) pentanoate (0.151 gm, 0.43 mmol), the title compound was isolated after HPLC purification on a Vydec C-18 column solvent A (acetonitrile:water:TFA 80:20:0.2) solvent B (water:TFA 99.8:0.2) using a gradient, (R$_f$=24 min.), as a solid 0.017 gm (10%). Mp >200° C.; MS: (M+H)$^+$ 369; $^1$H NMR (DMSO-d$_6$): 1.95 (m, 2H), 2.5 (m, 2H), 2.65 (dd, 1H), 2.85 (dd, 1H), 3.15 (m, 1H), 3.55 (s, 3H), 3.8 (s, 3H).

Example 19

Preparation of (±)-methyl 4-[(aminoiminomethyl) amino]-beta-[3-[(aminoiminomethyl)amino]phenyl] benzenepentanoate bis(trifluoroacetate)

Part A. Employing methods similar to Example 1 Part A, but using 3-acetylnitrobenzene (1.1 gm, 6.61 mmol) and 4-nitrobenzaldehyde (1 gm, 6.6.1 mmol), 3-nitro[3-(4-nitrophenyl)-1-oxo-2-propenyl]benzene was prepared as a solid 1.2 gm (63%). Mp 200–203° C.; $^1$H NMR (CDCl$_3$): 7.65 (d, 1H), 7.78 (t, 1H), 7.85 (d, 2H), 7.95 (d, 1H), 8.35 (d, 2H), 8.4 (d, 1H), 8.5 (d, 2H), 8.85 (s, 1H).

Part B. Employing methods similar to Example 1 Part B, but using 3-nitro[3-(4-nitrophenyl)-1-oxo-2-propenyl] benzene (1 gm, 3.35 mmol) methyl 3-(3-nitrophenyl)-5-(4-nitrophenyl)-2,4-pentadienoate as a mixture of isomers was prepared as an oil 0.708 gm (64%). MS: (M+NH$_4$)$^+$ 372; $^1$H NMR (CDCl$_3$): 3.8 (s, 3H), 5.95 (s, 1H), 6.55 (d, 1H), 7.65 (m, 4H), 8.2 (m, 3H), 8.3 (d, 1H), 8.7 (d, 1H).

Part C. Employing methods similar to Example 1 Part C, but using methyl 3-(3-nitrophenyl)-5-(4-nitrophenyl)-2,4-pentadienoate (0.700 gm, 1.97 mmol) methyl 3-(3-aminophenyl)-5-(4-aminophenyl)pentanoate was prepared as an oil 0.450 gm (76%). MS:(M+H)$^+$ 299; $^1$H NMR (CDCl$_3$): 1.9 (m, 2H), 2.35 (m, 2H), 2.55 (ddd, 2H), 3.05(m, 1H), 3.6 (s, 3H), 6.6 (m, 5H), 6.9 (d, 2H), 7.05 (t, 1H).

Part D. Employing methods similar to Example 13, but using methyl 3-(3-aminophenyl)-5-(4-aminophenyl) pentanoate (0.369 gm, 1.24 mmol), the title compound was isolated after HPLC purification on a Vydec C-18 column solvent A (acetonitrile:water:TFA 80:20:0.2) solvent B (water:TFA 99.8:0.2) using a gradient, (R$_f$=14 min), as a solid 0.050 gm (10%). MS:(M+H)$^+$ 383; $^1$H NMR (DMSO-d$_6$): 2.0 (m, 2H), 2.5 (m, 2H), 2.7 (dd, 1H), 2.85 (dd, 1H), 3.15 (m, 1H), 3.50 (s, 3H), 7.1 (m, 3H), 7.2 (m, 2H), 7.35 (s (broad), 2H), 7.4 (m, 3H), 9.6 (s, 1H), 9.7 (s, 1H).

Example 20

Preparation of (±)-ethyl 3-(aminoiminomethyl)-beta-[[4-(aminoiminomethyl)phenyl]methoxy] benzenepropanoate bis(trifluoroacetate)

Part A. A solution of the m-cyanobenzaldehyde (1.0 gm, 7.62 mmol) and ethyl trimethylsilyl acetate (1.22 gm, 7.62 mmol) in 7 mL THF was slowly added to a solution of tetrabutyl ammonium floride (0.048 mmol) (1M/THF) in 1 mL THF cooled to −78° C. under a nitrogen atmosphere. The reaction mixture was stirred for 10 minutes at −78° C. and was allowed to warm to ambient temperature. The reaction was monitored by NMR of small aliquots. After stirring for 3 hrs additional ethyl trimethylsilyl acetate was added in small portions (total of 3 mLs ethyl trimethylsilyl acetate). The reaction was stirred over night and then 8 mL tetrabutyl ammonium floride (1M/THF) was added to an ice cooled reaction mixture. This stirred for 20 minutes and was partitioned between ethyl acetate and water. The combined organic layer was washed with water 3×, brine, dried over magnesium sulfate and concentrated to give a viscous oil. This was purified by flash chromatography on silica gel eluting hexane:ethyl acetate (v:v 80:20) to give ethyl 3-(cyano)-beta-(hydroxy)benzenepropanoate as viscous oil 0.91 gm. (55%). MS 237(M+NH4). $^1$H NMR (CDCl$_3$): 7.7(s, 1H), 7.6(m,2H), 7.45(t, 1H), 5.15(t, 1H), 4.2(q, 2H), 3.65(bs, 1H), 2.70(d, 2H), 1.25(t, 3H).

Part B. The 3-(cyano)-beta-(hydroxy)benzenepropanoate (0.33 gm, 1.51 mmol), a-bromo p-tolunitrile (0.59 gm, 3.0 mmol), cesium carbonate (0.74 gm, 2.26 mmol) and catalytic amount of potassium iodide were combined in 10 mLs acetone under a nitrogen atmosphere. The reaction was heated to reflux for 2½ days, allowed to cool, was diluted with ethyl acetate and the solids were filtered off. The filtrate was concentrated to give a crude yellow oil. The product was purified by flash chromatography on silica gel (200 mLs)

eluting toluene:ethyl acetate (v:v, 90:10) to give the ethyl 3-(cyano)-beta-[(4cyanophenyl)methoxy] benzenepropanoate as a viscous oil 0.25 gm (50%). MS 352(M+NH4). $^1$H NMR (CDCl$_3$); 7.7–7.35(m, 8H), 4.92 (dd, 1H), 4.45(dd, 2H), 4.15(m, 2H), 2.85(dd, 1H), 2.60(dd, 1H), 1.20(t,3H).

Part C. The ethyl 3-(cyano)-beta-[(4-cyanophenyl) methoxy]benzenepropanoate (0.20 gm, 0.599 mmol) was dissolved in 10 mLs ethanol under a nitrogen atmosphere and cooled in an ice bath. Hydrogen chloride gas was bubbled through the solution for 20 minutes, then the reaction was allowed to warm to ambient temperature. The reaction mixture was stirred for 18 hrs then was concentrated in vacuo to give a viscous yellow residue. The residue was taken up in 10 mLs ethanol and cooled in an ice bath under a nitrogen atmosphere. Ammonia gas was bubbled through the solution for ½ hr, the reaction mixture was stirred at 0° C. for 2 hrs then was allowed to warm to ambient temperature and stirred for 48 hrs. The reaction was concentrated in vaccuo to give a viscous amber oil. A 0.050 gm sample was purified by HPLC on a Vydec C18 semiprep column eluting Solvent A (acetonitrile:water:TFA 80:20:0.2) and solvent B (water:TFA 99.8:0.2) using a gradient, (Rf=10 minutes) to give the title compound as a white powder 0.028 gm. MS 369(M+H, 185.1(M+2H)$^{+2}$ $^1$H NMR (DMSO-d6): 8.3(d, 4H), 9.1(M, 1H), 7.85(s, 1H), 7.75(m, 4H), 7.65(t, 1H), 7.5(d, 2H), 4.95(m, 1H), 4.45(q, 2H), 4.05(m,2H), 2.85(m, 1H), 2.78(m, 1H), 1.15(t, 3H).

Example 21

Preparation of (±)-ethyl 3-(aminoiminomethyl)-beta-[[[3-[(aminoiminomethyl)amino]phenyl]acetyl] amino]benzene propanoate bis(trifluoroacetate)

Part A. The 3-cyano benzaldehyde (2.0 gm, 15.3 mmol), malonic acid (1.6 gm, 15.3 mmol) and ammonium acetate (2.37 gm, 30.75 mmol) were combined in 35 mLs ethanol under a nitrogen atmosphere. The reaction mixture was heated over night to become a thick slurry. The slurry was filtered and the solids were washed with additional ethanol. The 3-(cyano)-beta-(amino)benzene propanoic acid was isolated as a white powder 1.58 gm (55%) MS 191(M+H)$^+$ $^1$H NMR (DMSO-d6): 8.11(s, 1H), 7.96(d, 1H), 7.90(d, 1H), 7.46(t,1H), 5.7(s,4H), 4.66(m, 1H), 3.61(dd, 1H), 3.06(dd, 1H).

Part B. The 3-(cyano)-beta-(amino)benzene propanoic acid was dissolved in 10 mLs ethanol under a nitrogen atmosphere and cooled to 0° C. in an ice bath. Hydrogen chloride gas was bubbled through the solution for 2–3 minutes, the reaction flask was stoppered and allowed to warm to ambient temperature. The reaction mixture was stirred for 48 hrs and was concentrated in vacuuo to give ethyl 3-(cyano)-beta-(amino)benzene propanoate hydrochloride as a colorless glass 0.63 gms (95%). MS 219(M+H)$^+$ $^1$H NMR (DMSO-d6): 8.87(bs, 3H), 8.1(s, 1H), 7.95(d, 1H), 7.88(d, 1H), 7.65(t, 1H), 4.7(bs,1H), 4.0(q, 2H0, 3.22 (dd, 1H), 3.07(dd, 1H), 1.07(t, 3H).

Part C. The ethyl 3-(cyano)-beta-(amino)benzene propanoate hydrochloride (0.15 gm,0.59 mmol), 3-amino phenyl acetic acid (0.11 gm, 0.59 mmol), 1-(3-dimethylaminopropyl)-3-ethhylcarbodiimide hydrochloride (0.17 gm, 0.89 mmol) and 4-dimethyl amino pyridine (0.16 gm, 1.3 mmol) were combined in 10 mLs methylene chloride under a nitrogen atmosphere at ambient temperature. The reaction mixture was stirred for 48 hrs, was poured into water, and extracted with methylene chloride. The combined organic layer was washed with brine, dried over magnesium sulfate and concentrated to give a viscous amber oil. The crude product was purified by flash chromatography on silica gel (75 mLs) eluting hexane:ethyl acetate (v:v ,75:25) to give ethyl 3-(cyano)-beta-[[(3-amino)phenyl]acetyl] amino]benzene propanoate as an oil 0.11 gm (53%). MS 352(M+H)$^{+1}$ $^1$H NMR (CDCl$_3$): 7.52(m, 1H), 7.4(m, 3H), 7.17(t, 1H), 6.78(d, 1H), 6.65(dd, 2H), 6.57(s, 1H), 5.37(m, 1H), 4.0(q, 2H), 3.75(bs, 2H), 3.52(s, 2H), 2.77(d, 2H), 1.12(t, 3H).

Part D. Employing methods similar to Example 13 but using ethyl 3-(cyano)-beta-[[(3-amino)phenyl]acetyl] amino]benzene propanoate (0.1 gm, 0.28 mmol) the title compound was isolated after HPLC purification on a Vydac C-18 column eluting Solvent A (acetonitrile:water:TFA 80:20:0.2) and solvent B (water:TFA 99.8:0.2) using a gradient, (Rf 13.1 min) as a white powder MS 206(M+2H)$^{+2}$ HRMS calc. 411.2144 found 411.2145 $^1$H NMR (DMSO-d6): 9.73(s, 1H), 9.3(s, 2H), 9.05(s, 2H), 8.73(d, 1H), 7.77(s, 1H), 7.67(m, 2H), 7.56(t, 1H), 7.42–7.32(m, 4H), 7.18–7.08 (m, 3H), 5.28(m, 1H), 4.0(q, 2H), 3.55–3.45(m, 2H), 2.87–2.75(m, 2H), 1.09(t, 3H).

Example 22

Preparation of (±)-ethyl 3-(aminoiminomethyl)-gamma-[[4-(aminoiminomethyl)phenyl]methoxy] benzenebutanoate bis(trifluoroacetate)

Part A. A mixture of 3-cyanobenzaldehyde (2.0 gm, 15.2 mmol), 1-ethoxy-1-trimethylsilyloxycyclopropane (3.44 gm, 19.73 mmol) and zinc iodide (0.12 gm, 0.38 mmol) in 30 mLs methylene chloride under a nitrogen atmosphere was stirred at ambient temperature for 18 hrs. The reaction mixture was poured into water and extracted with methylene chloride. The combined organic layers was washed with water, brine, dried over magnesium sulfate and concentrated to give the crude product as a yellow oil. The oil was purified by flash chromatography on silica gel (100 mLs) eluting hexane:ethyl acetate (v:v, 90:10) to give ethyl 3-(cyano)-gamma-(trimethylsilyloxy)benzenebutanoate as a viscous oil 1.75 gm (38% yield) MS 323(M+H)$^+$, $^1$H NMR (CDCl$_3$) 7.8(s, 1H), 7.5(d, 2H), 7.39(t, 1H), 4.73(m, 1H), 4.07(q, 2H), 2.41–2.2 (m, 2H), 2.0–1.8(m, 2H), 1.20(t, 3H), 0.03 (s, 9H).

Part B. Tetrabutyl ammonium floride 1 M in THF (17 mLs) was added slowly to a solution of ethyl 3-(cyano)-gamma-(trimethylsilyloxy)benzenebutanoate (1.75 gm, 5.72 mmol) in 50 mLs THF cooled in an ice bath under a nitrogen atmosphere. The red brown solution stirred at 0° C. for 2 hrs. The reaction solution was partitioned between ethyl acetate and water. The combined organic layer was washed with water, brine, dried over magnesium sulfate and concentrated to give the product as a dark amber oil. This was purified by flash chromatography on silica gel (100 mLs) eluting hexane:ethyl acetate (v:v,75:25) to give ethyl 3-(cyano)-gamma-(hydroxy)benzenebutanoate as a light amber oil 1.2 gms (90%) MS 216(M–OH), 188(M–OEt) $^1$H NMR (CDCl$_3$): 7.66(s, 1H), 7.62–7.55(m, 2H), 7.43(t, 1H), 4.82 (m, 1H), 4.15(q, 2H), 2.82(bs, 1H), 2.46(m, 2H), 2.07–1.97 (m, 2H), 1.27(t, 3H).

Part C. Sodium hydride (0.76 mmol) (washed free of the mineral oil with hexane) was added to a solution of ethyl 3-(cyano)-gamma-(hydroxy)benzenebutanoate (0.15 gm, 0.64 mmol), a-bromo-p-tolunitrile (0.125 gm, 0.64 mmol) and potassium iodide in 5 mL DMF at 0° C. under a nitrogen atmosphere. The reaction was stirred for 2 hrs at 0° C. and was allowed to stir at ambient temperature overnight. The reaction solution was poured into 1N HCl and extracted with ethyl acetate. The combined organic layer was washed with water, brine, dried over magnesium sulfate and concentrated to give the crude product as a viscous oil. The product was purified by flash chromatography on silica gel (75 mL) eluting toluene:ethyl acetate (v:v, 90:10) to give ethyl 3-(cyano)-gamma-[[4-(cyano)phenyl]methoxy]benzenebutanoate as a semisolid residue 0.10 gm (45% yield) MS 366(M+NH4)$^+$ $^1$H NMR (CDCl$_3$): 7.72–7.47(m, 6H), 7.42(d, 2H), 4.5–4.3(m, 3H), 4.1(q, 2H), 2.42(m, 2H), 2.17–1.97(m, 2H), 1.23(t, 3H).

Part D. Employing methods similar to Example 1 Part D, but using ethyl 3-(cyano)-gamma-[[4-(cyano)phenyl]methoxy]benzenebutanoate (0.09 gm, 0.26 mmol) the title compound was isolated after HPLC purification on a Vydac C-18 column eluting Solvent A (acetonitrile:water:TFA 80:20:0.2) and solvent B (water:TFA 99.8:0.2) using a gradient, (Rf=15 min) as a white solid residue 0.055 gm MS 383(M+H)$^+$, 192(M+2H)$^{+2}$ HRMS calc 383.2083, found 383.2056 $^1$H NMR (DMSO-d6): 9.31(d, 4H), 9.05(d, 4H), 7.78(m, 4H), 7.71(d, 1H), 7.65(t, 1H), 7.55(d, 2H), 4.57(m, 1H), 4.42(dd, 2H), 4.0(q, 2H), 2.35(m, 2H), 2.1–1.95(m, 2H), 1.12(t, 3H).

Example 23

Preparation of (±)-4-(aminoiminomethyl)-beta-[3-(aminoiminomethyl)phenyl]-N-methoxybenzenepentanamide bis(trifluoroacetate)

Part A. A solution of 3-(3-cyanophenyl)-5-(4-cyanophenyl)pentanoic acid (0.15 gm, 0.49 mmol), methoxylamine hydrochloride (0.041 gm, 0.54 mmol), 1-(3-dimethylaminopropyl)-3-ethhylcarbodiimide hydrochloride (0.14 gm, 0.73 mmol) and 4-dimethylaminopyridine (0.15 gm, 1.22 mmol) in 5 mLs DMF under a nitrogen atmosphere was stirred for 18 hrs. The reaction solution was poured into water and extracted with ethyl acetate. The combined organic layer was washed with 1 N HCl (2×), water, brine, dried over magnesium sulfate and concentrated to give the crude product as a colorless viscous oil. The product was purified by flash chromatography on silica gel (50 mLs) eluting methylene chloride:ethyl acetate (v:v, 60:40) to give 4-(cyano)-beta-(3-cyanophenyl)-N-methoxybenzene pentanamide as a colorless vicous oil 0.15 gm (91%) $^1$H NMR (CDCl$_3$): 8.03(bs, 1H), 7.56–7.42(m, 6H), 7.15(d, 2H), 3.58(s, 3H), 3.28(m, 1H), 2.8–1.85(m, 6H).

Part B. Employing methods similar to Example 1 Part D, but using 4-(cyano)-beta-(3-cyanophenyl)-N-methoxybenzene pentanamide (0.12 gm, 0.36 mmol) the title compound was isolated after HPLC purification on a Vydac C-18 column eluting Solvent A (acetonitrile:water:TFA 80:20:0.2) and solvent B (water:TFA 99.8:0.2) using a gradient,(Rf=14 min) as a white powder. MS 184.7(M+2H)$^{+2}$ HRMS calc 368.2086 found 368.2083 $^1$H NMR (DMSO-d6): 10.9(s, 1H), 9.28(s, 2H), 9.21(s, 2H), 9.08(s, 2H), 8.98(s, 2H), 7.73(d, 2H), 7.67(m, 2H), 7.56(m, 2H), 7.38(d, 2H), 3.35(s, 3H), 3.12(m, 1H), 2.55–1.95(m, 6H).

Example 24

Preparation of (±)-methyl N-[3-[3-(aminoiminomethyl)phenyl]-5-[4-(aminoiminomethyl)phenyl]-1-oxopentyl]glycine bis(trifluoroacetate)

Part A. Employing methods similar to Example 24 Part A, but using 3-(3-cyanophenyl)-5-(4-cyanophenyl)pentanoic acid (0.15 gm, 0.49 mmol) and methyl glycine ester (0.068 gm, 0.54 mmol), methyl N-[3-(3-cyanophenyl)-5-(4-cyanophenyl)-1-oxopentyl]glycine was isolated after flash chromatography purification on silica gel (75 mLs) eluting methylene chloride:ethyl acetate (v:v, 75:25) as a colorless viscous oil 0.13 gm (71%) MS 393(M+NH4) $^1$H NMR (CDCl$_3$): 7.57–7.42(m, 6H), 7.17(d, 2H), 5.85(m, 1H), 4.0(dd, 1H), 3.92(dd, 1H), 3.25(m, 1H), 2.65–2.45(m, 4H), 2.1(m, 1H), 1.93(m, 1H).

Part B. Employing methods similar to Example 1 Part D, but using methyl N-[3-(3-cyanophenyl)-5-(4-cyanophenyl)-1-oxopentyl]glycine (0.11 gm, 0.29 mmol) the title compound was isolated after HPLC purification on a Vydac C-18 column eluting Solvent A (acetonitrile:water:TFA 80:20:0.2) and Solvent B (water:TFA 99.8:0.2) using a gradient (Rf=13 min) as a semisolid residue 0.012 gm MS 205.8(M+2H)$^{+2}$ 1H NMR (DMSO-d6): 9.25(s, 2H), 9.20(s, 2H), 9.0(s, 2H), 8.9(s, 2H), 8.27(t, 1H), 7.73–7.52(m,6H), 7.37(d, 2H), 3.8 (dd, 1H), 3.72(dd, 1H), 3.17(m, 3H),2.57–2.42(m, 2H), 2.0(m, 2H).

Example 25

Preparation of (±)-4-(aminoiminomethyl)-beta-[3-(aminoiminomethyl)phenyl]-N-methylbenzenepentanamide bis(trifluoroacetate)

Part A. Oxalyl chloride was added to a solution of 3-(3-cyanophenyl)-5-(4-cyanophenyl)pentanoic acid (0.25 gm, 0.82 mmol) in 10 mLs methylene chloride under a nitrogen atmosphere at ambient temperature. The reaction was stirred for 2 hrs and was concentrated in vacuo to give a semi solid residue. The residue was taken up in 5 mLs methylene chloride and 40% methyl amine in water (5 mLs) was added. The reaction was stirred vigorously for 2 hrs and then was partioned between 1N HCl and ethyl acetate. The organic layer was washed with water, brine dried over magnesium sulfate and concentrated to give the crude product as a semisolid. The residue was purified by flash chromatography on silica gel (100 mLs) eluting methylene chloride:ethyl acetate (v:v, 80:20) to give 4-(cyano)-beta-(3-cyanophenyl)-N-methylbenzenepentanamide as a semi-solid 0.120 gm (46%) MS 335(M+NH4) $^1$H NMR (CDCl$_3$): 7.6–7.4(m, 6H), 7.17(d, 2H), 5.3(m, 1H), 3.27(m, 1H), 2.67(d, 2H), 2.55–2.35(m, 4H), 2.07(m, 1H), 1.95(m, 1H).

Part B. Employing methods similar to Example 1 Part D, but using 4-(cyano)-beta-(3-cyanophenyl)-N-methylbenzenepentanamide (0.1 gm, 0.32 mmol) the title compound was isolated after HPLC purification on a Vydac column eluting Solvent A (acetonitrile:water:TFA 80:20:0.2), Solvent B (water:TFA 99.8:0.2) using a gradient (Rf=15.3 min) as a white solid. MS 176.7(M+2H)$^{+2}$ HRMS calc 352.2137 found 352.2138 $^1$H NMR (DMSO-d6): 9.31(s, 2H), 9.23(s, 2H), 9.21(s, 2H), 9.11(s, 2H), 7.75–7.65(m, 5H), 7.55(d, 2H), 7.37(d, 2H), 3.15(m, 1H), 2.55–2.35(m, 4H), 1.95(m, 2H).

Example 26

Preparation of (±)-1-[3-[3-(aminoiminomethyl)phenyl]-5-[4-(aminoiminomethyl)phenyl]-1-oxopentyl]pyrrolidine bis(trifluoroacetate)

Employing methods similar to Example 24 Part A but using 3-(3-cyanophenyl)-5-(4-cyanophenyl)pentanoic acid (0.2 gm, 0.66 mmol), and pyyrolidine (0.047 gm, 0.66 mmol), 1-[3-[3-cyanophenyl]-5-[4-cyanophenyl]-1-oxopentyl]pyrrolidine was isolated after flash chromatography on slica gel eluting methylene chloride; ethyl acetate (v:v, 60:40) as a viscous oil 0.14 gm (45% yield) MS 358(M+H)+, 375(M+NH4)+ $^1$H NMR (CDCl$_3$): 7.55–7.39 (m, 6H), 7.2(d, 2H), 3.45–3.3(m, 4H), 3.2(m, 1H), 2.6–2.4 (m, 4H), 2.17(m, 1H), 1.95–1.75(m, 5H).

Part B. Employing methods similar to Example 1 Part D, but using 1-[3-[3-cyanophenyl]-5-[4-cyanophenyl]-1-oxopentyl]pyrrolidine (0.13 gm, 0.36 mmol) the title compound was isolated after HPLC purification using a Vydac C-18 column eluting Solvent A (acetontrile:water:TFA 80:20:0.2), Solvent B (water:TFA 99.8:0.2) using a gradient (Rf=14.2 min) as a white powder 0.085 gm MS 392(M+H)+, 196.7(M+2H)$^{+2}$ $^1$H NMR (DMSO-d6): 9.31(s, 2H), 9.23(s, 2H), 9.20(s, 2H), 9.12(s, 2H), 7.75–7-5(m, 6H), 7.37(d, 2H), 3.4–3.1(m, 7H), 2.75–2.45(m, 2H), 2.0(m, 2H), 1.85–1.65 (m, 4H).

Example 27

Preparation of (±)-ethyl 3-(aminoiminomethyl)-beta-[4-(aminoiminomethyl)phenyl]benzene pentanoate bis(trifluoroacetate)

Part A. Employing methods similar to Example 1 Part A but using m-cyano benzaldehyde (0.91 gm, 6.89 mmol) and 4-acetyl benzonitrile (1.0 gm, 6.89 mmol), 4-[3-(3-cyanophenyl)-1-oxo-2-propenyl]benzonitrile was isolated as a pale yellow powder, 1.4 gm (79%), 1H NMR (CDCl3) 8.53(s,1H), 8.35(d,2H), 8.15–8.20(m,3H), 7.92(d, 1H), 7.82 (d, 1H), 7.67(t, 1H).

Part B. Employing methods similar to Example 1 Part B, but using 4-[3-(3-cyanophenyl)-1-oxo-2-propenyl] benzonitrile (0.5 gm, 1.95 mmol), methyl 3-(4-cyanophenyl)-5-(3-cyanophenyl)-2,4-pentadienoate was prepared as mixture of isomers as a semisolid 0.52 gm, (85%). MS 332(M+NH4)+ 1H NMR (CDCl3) 8.55–7.0(m, 10H) 6.45–6.15(m, 1H), 3.8 (s, 3H).

Part C. Employing methods similar to Example 1 Part C, but using methyl 3-(4-cyanophenyl)-5-(3-cyanophenyl)-2,4-pentadienoate (0.5 gm, 1.59 mmol), methyl 3-(3-cyanophenyl)-5-(4-cyanophenyl)pentanoate was isolated after flash chromatography on silica gel (100 mLs) eluting toluene:ethyl acetate 95:5 to give a viscous oil 0.43 gm (85%) MS 319(M+H)+ $^1$H NMR (CDCl$_3$): 7.65(d, 2H), 7.48(d, 1H), 7.4–7.15(m, 5H), 3.7(s, 3H), 3.2(m, 1H), 2.67 (m, 2H), 2.42(t, 2H), 2.1–1.9(m, 2H).

Part D. Employing methods similar to Example 1 Part D, but using methyl 3-(3-cyanophenyl)-5-(4-cyanophenyl) pentanoate (0.31 gm, 0.97 mmol)and ethanol, the title compound was isolated after HPLC purification on a Vydec C-18 column eltuing solvent A (acetonitrile:water:TFA 80:20:0.2) and slovent B (water:TFA 99.8:0.2) using a gradient (Rf=15 min) as a white powder 0.146 gm Mp 180–85° C. MS367 (M+H)+ HRMS calc 367.2134 found 367.2136 $^1$H NMR (DMSO-d6): 9.27(s, 4H), 9.22(s, 2H), 9.21(s, 2H), 7.8(d, 2H), 7.65–7.47(m, 6H), 3.92(m,2H), 3.18(m, 1H), 2.8(dd, 1H), 2.67(dd, 1H), 2.6–2.33(m, 2H), 2.0(m, 2H).

Example 28

Preparation of (±)-3-(aminoiminomethyl)-beta-[4-(aminoiminomethyl)phenyl]benzene pentanoic acid bis(trifluoroacetate)

Employing methods similar to Example 6, but using (±)-ethyl 3-(aminoiminomethyl)-beta-[4-(aminoiminomethyl)phenyl]benzene pentanoate bis (trifluoroacetate) (0.05 gm, 0.84 mmol) the title compound was isolated after trituration in ethyl ether as a white powder 0.04 gm MP 130–5° C. MS 339(M+H)+, 170(M+2H)$^{+2}$ $^1$H NMR (DMSO-d6): 9.36(s, 4H), 9.17(s, 2H), 9.15(s, 2H), 7.8(d, 2H), 7.62(m, 2H), 7.52(d, 2H), 7.48(m, 2H), 3.17(m, 1H), 2.73(dd,1H), 2.57(dd,1H), 2.5–2.4(m, 2H), 1.95(m, 2H).

Example 29

Preparation of (±)-ethyl 4-(aminoiminomethyl)-beta-[4-(aminoiminomethyl)phenyl] benzenepentanoate bis(trifluoroacetate)

Part A. Employing methods similar to Example 1 Part A but using 4-cyano benzaldehyde (1.80 gm, 13.8 mmol) and 4-acetyl benzonitrile (1.0 gm, 6.89 mmol), 4-[3-(4-cyanophenyl)-1-oxo-2-propenyl]benzonitrile was isolated as a pale yellow powder, 0.4 gm (20%) MS 259(M+H)+ $^1$H NMR (CDCl$_3$): 7.78(d, 2H), 7.6(t, 1H), 7.5–7.0(m, 7H).

Part B. Employing methods similar to Example 1 Part B, but using 4-[3-(4-cyanophenyl)-1-oxo-2-propenyl] benzonitrile (0.3 gm, 1.16 mmol), methyl 3-(4-cyanophenyl)-5-(4-cyanophenyl)-2,4-pentadienoate as a mixture of E and Z isomers. This was purified by flash chromatography on silica gel eluting methylene chloride to give mixture of isomers 0.31 gm (85%) MS 332(M+NH4)+ $_1$H NMR (CDCl$_3$): 8.5(d, 1H), 7.75(d, 2H), 7.65(d, 2H), 7.56(d, 2H), 7.45(d, 2H), 6.47(d, 2H), 3.82(s, 3H).

Part C. Employing methods similar to Example 1 Part C, but using methyl 3-(4-cyanophenyl)-5-(4-cyanophenyl)-2,4-pentadienoate (0.5 gm, 1.59 mmol), methyl 3-(4-cyanophenyl)-5-(4-cyanophenyl)pentanoate was isolated as an oil 0.3 gms (99%) MS 319(M+H)+ $^1$H NMR (CDCl$_3$): 7.65(d, 2H), 7.55(d, 2H), 7.45(d, 2H), 7.17(d, 2H), 3.7(s, 3H), 3.2(m, 1H), 2.65(m, 2H), 2.50(t, 2H), 2.1–1.90(m, 2H).

Part D. Employing methods similar to Example 1 Part D, but using methyl 3-(4-cyanophenyl)-5-(4-cyanophenyl) pentanoate (0.30 gm, 0.94 mmol) the title compound was isolated after HPLC purification on a Vydec C-18 column using a gradient solvent A (acetonitrile:water:TFA 80:20:0.2) solvent B (water:TFA 99.8:0.2) using a gradient (Rf=14.3 min) as a white powder 0.12 gms Mp 248–9° C. MS 367(M+H)+ $^1$H NMR (DMSO-d6): 9.27(s, 2H), 9.25(s, 2H), 9.17(s, 2H), 9.15(s, 2H), 7.78(d, 2H), 7.75(d, 2H), 7.55(d, 2H), 7.37(d, 2H),3.90(m,2H), 3.15(m,1H), 2.85(dd, 1H), 2.7(dd, 1H), 2.6–2.4 (m, 2H), 1.95 (m, 2H), 1.1 (t, 3H).

Example 30

Preparation of (±)-ethyl 3-(aminoiminomethyl)-beta-[[[4-aminoiminomethyl)phenyl]sulfonyl]amino] benzenepropanoate bis(trifluoroacetate)

Part A. p-Cyano phenyl sulfonyl chloride (0.41 gm, 2.02 mmol) in 2 mL dioxane was added to a rapidly stirring mixture of 3-(cyano)-beta-(amino)benzene propanoate hydrochloride (0.35 gm, 1.84 mmol), 10 mLs dioxane and 1 N sodium hydroxide (3.86 mL) cooled in an ice bath under a nitrogen atmosphere. The reaction was stirred for 30 minutes at 0° and allowed to warm to ambient temperature and stir overnight. The reaction was partitioned between ethyl acetate and 1 N HCl. The organic layer was washed with brine, dried over magnesium sulfate and concentrated to give the crude product as a colorless viscous oil 0.62 gm. The product was purified by flash chromatography on silica gel (100 mLs) eluting toluene:ethyl acetate:acetic acid (v:v:v, 70:30:2) to give ethyl 3-(cyano)-beta-[[(4-cyanophenyl)sulfonyl]amino]benzenepropanoate as a white semisolid 0.32 gm (50%) MS 373(M+NH4)+ $^1$H NMR (CDCl$_3$) 12.4(bs, 1H), 8.79(d, 1H), 7.82(d, 2H), 7.65(d, 2H), 7.6(d, 1H), 7,45(m, 2H), 7.35(t, 1H), 4.72(m, 1H), 2.65(m, 2H).

Part B. Employing methods similar to Example 1 Part D, but using ethyl 3-(cyano)-beta-[[(4-cyanophenyl)sulfonyl]amino]benzenepropanoate (0.21 gm, 0.59 mmol) the title compound was isolated after HPLC purification on a Vydec C-18 column eluting with Solvent A (acetonitrile:water:TFA, 80:20:0.2), Solvent B (water:TFA, 99.8:0.02) using a gradient (Rf=13.2 min) as a white crystalline solid 0.26 gms, Mp 248–9° C. MS 418,2(M+H)+, 209.8(M+2H)+2 HRMS calc 418.1549 found 418.1547 $^1$H NMR (DMSO-d6): 9.4(s, 2H), 9.38(s, 2H), 9.27(s, 2H), 9.17(s, 2H), 8.85(d, 1H), 7.8(s, 4H), 7.7(s, 1H), 7.6(d, 1H), 7.45(d, 1H), 7.35(t, 1H), 4.79(m, 1H), 3.92(m, 2H), 2.75(d, 2H), 1.1(t, 3H).

Example 31

Preparation of (±)-ethyl 3-(aminoiminomethyl)-beta-[[(4-methylphenyl)sulfonyl]amino] benzenepropanoate mono(trifluoroacetate)

Part A. Employing methods similar to Example 32 Part A but using p-toluene sulfonyl chloride (0.22 gm, 1.15 mmol) ethyl 3-(cyano)-beta-[[(4-methylphenyl)sulfonyl]amino] benzene propanoate was isolated after flash chromatography on silica gel (100 mLs) eluting with toluene:ethyl acetate:acetic acid (v:v:v, 70:30:2) as a semisolid 0.29 gm (80% yield) MS 362(M+NH4)+ $^1$H NMR (DMSO-d6): 12.33(bs, 1H), 8.35(d, 1H), 7.5–7.25(m, 6H), 7.09(d, 2H), 4.67(m, 1H), 2.7–2.55(m, 2H), 2.32(s, 3H).

Part B. Employing methods similar to Example 1 Part D, but using ethyl 3-(cyano)-beta-[[(4-methylphenyl)sulfonyl]amino]benzenepropanoate (0.27 gm, 0.78 mmol) the title compound was isolated after HPLC purification on Vydac C-18 column eluting with Solvent A (acetonitrile:water:TFA 80:20:0.2) and solvent B (water:TFA 99.8:2) using a gradient (Rf=14.1 min) as a white crystalline powder 0.24 gms mp 208–9° C. MS 390(M+H)+ HRMS calc 390.1487 found 390.1489 1H NMR (DMSO-d6): 9.2(bs, 4H), 9.12(bs, 4H), 8.42(d, 1H), 7.6(m, 2H), 7.5–7.35(m, 4H), 7.15(d, 2H), 4.7(m, 1H), 3.90(m, 2H), 2.7(d, 2H), 2.3(s, 3H), 1.1(t, 3H).

Example 32

Preparation of (±)-methyl 3-(aminoiminomethyl)-beta-(phenylmethoxy)benzenepropanoate mono (trifluoroacetate)

Part A. Employing methods similar to Example 21 Part B, but using benzyl bromide, methyl 3-(cyano)-beta-(phenylmethoxy)benzenepropanoate was isolated as an oil, MS 237(M+NH4)+, $^1$H NMR (CDCl$_3$) 7.7(s,1H), 7.6(m, 2H), 7.5(d, ,1H), 7.3(m, 5H), 4.9(m,1H), 4.4(d, 1H), 4.3(d, 1H), 4.1(m, 2H), 2.9(q, 1H), 2.6(q, 1H), 1.2(t, 3H).

Part B. Employing methods similar to Example 1 Part D, but using methyl 3-(cyano)-beta-(phenylmethoxy) benzenepropanoate (0.21 gm, 0.66 mmol) the title compound was isolated after HPLC purification as a semisolid 0.078 gm (37%), Mp 138–140° C. MS 313(M+H)+, HRMS calc 313.1552, found 313.1551 $^1$H NMR (DMSO-d6) 9.3(s, 2H), 9.0(s, 2H), 7.85(s, 1H), 7.8(m, 2H), 7.4(t, 1H), 7.2–7.4 (m,5H), 4.9(q, 1H, 4.4(q, 2H), 3.6(s, 3H), 2.8(m,2H).

Example 101

Preparation of ethyl N-[4-[4-[(aminoiminomethyl) amino]phenyl]butyl]-N-[3-(aminoiminomethyl) phenyl]glycine bis(trifluoroacetate)

Part A. Pyridine (0.66 mL, 8.21 mmol) was added slowly to an ice cooled solution of 4-nitrophenyl butanol (1.0 gm,5.13 mmol) and dibromotriphenylphosphorane (2.8 gm, 6.66 mmol) in 20 mL acetonitrile under a nitrogen atmosphere. The reaction solution was stirred for ½ hr and allowed to warm to ambient temperature and stir overnight. The reaction was concentrated invacuo to give a residue. The residue was filtered through a short plug of silica gel and then the product was purifed by flash chromatography on silica gel eluting methylene chloride:hexane (v:v, 50:50), to give 1-bromo-4-(4-nitrophenyl)butane as an oil 1.3 gm (98%) MS 275(M+NH4)+ $^1$H NMR (CDCl$_3$): 8.2(d, 2H), 7.4(d, 2H), 3.4(t, 2H), 2.8(t, 2H), 1.8–2.0(m, 4H).

Part B. A mixture of 3-amino-benzonitrile (0.44 gm, 3.4 mmol), 1-bromo-4-(4-nitrophenyl)butane (1.05 gm, 4.08 mmol), sodium bicarbonate (0.571 gm, 6.8 mmol) and 10 mL hexamethylphosphoramide was heated to 80° C. under a nitrogen atmosphere for 4 hrs. The reaction was allowed to cool and was partitioned between ethyl acetate and water. The combined organic layer was washed with water, brine dried over magnesium sulfate and concentrated to give the crude product. The product was purified by flash chromatography on silica gel eluting methylene chloride:hexane (v:v, 60:40) to give 1-(N-3-cyanophenyl)-4-(4-nitrophenyl)aminobutane as an oil 0.80 gm (80%). MS 313(M+NH4)+ 1H NMR (CDCl$_3$): 8.2(d, 2H), 7.35(d, 2H), 7.2(t, 1H), 7.0(d, 1H), 6.8(m, 2H), 3.8(bs,1H), 3.2(m, 2H), 2.8(m, 2H), 1.6–1.8(m, 4H).

Part C. A mixture of 1-(N-3-cyanophenyl)-4-(4-nitrophenyl)aminobutane (0.80 gm, 2.7 mmol), ethyl bromoacetate (0.9 gm, 5.4 mmol), sodium bicarbonate (0.455 gm, 5.4 mmol) and 10 mL hexamethylphosphoramide was heated to 120° C. under a nitrogen atmosphere for 18 hrs. The reaction was allowed to cool and was partitioned between ethyl acetate and water. The combined organic layer was washed with water, brine dried over magnesium sulfate and concentrated to give the crude product. The product was purified by flash chromatography on silica gel eluting methylene chloride:hexane (v:v, 60:40) to give ethyl N-[4-[4-nitrophenyl]butyl]-N-[3-cyanophenyl]glycine as an oil 0.80 gm (78%). MS 382(M+H)+ $^1$H NMR (CDCl$_3$): 8.1(d, 2H), 7.4(d, 2H), 7.2(m, 1H), 7.0(d, 1H), 6.8(m, 2H), 4.2(q, 2H), 4.0(s, 2H), 3.4(m, 2H), 2.8(m, 2H), 1.7(m, 4H), 1.2(t, 3H).

Part D. A solution of ethyl N-[4-[4-nitrophenyl]butyl]-N-[3-cyanophenyl]glycine (0.31 gm, 0.81 mmol) and 20 mL methanol:ethyl acetate (v:v, 50:50) was degassed with nitrogen in a Parr shaker bottle, then 10% palladium on carbon was added. The reaction was charged to 50 PSI hydrogen and shaken for ½ hr. The catalyst was filtered off over celite, the filtrate concentrated and the product purifed by flash chropmatography on silica gel eluting ethyl acetate:methylene chloride (v:v, 10:90) to give ethyl N-[4-[4-aminophenyl]butyl]-N-[3-cyanophenyl]glycine as a semisolid 0.27 gm (94%). MS 352(M+H)+ $^1$H NMR (CDCl$_3$): 7.2(m, 1H), 7.0(m, 3H), 6.8(m, 2H), 6.6(d, 2H), 4.2(q, 2H), 4.0(s, 2H), 3.6(bs, 2H), 3.4(m, 2H), 2.6(m, 2H), 1.6(m, 4H), 1.2(t, 3H).

Part E. A solution of ethyl N-[4-[4-aminophenyl]butyl]-N-[3-cyanophenyl]glycine (0.12 gm, 0.34 mmol) and 3,5-dimethylpyrazole-1-carboxamidine nitrate (0.103 gm, 0.51 mmol) in 10 mL pyridine was heated to 100° C. under a nitrogen atmosphere for 3 hrs. The reaction mixture was allowed to cool and was partitioned between ethyl acetate and water. The combined organic layer was washed with water, brine, dried over magnesium sulfate and concentrated to give the crude product. The product was purified by flash chromatography on silica gel eluting chloroform:methanol (v:v, 80:20) to give ethyl N-[4-[4-[(aminoiminomethyl) amino]phenyl]butyl]-N-[3 -cyanophenyl]glycine 0.078 gm (58%) MS 394(M+H)+ 1H NMR (CDCl3): 7.0(m, 10H), 6.8(m, 2H), 4.2(q, 2H), 4.0(s, 2H), 3.4(m, 2H), 2.7(m, 2H), 1.2(t, 3H).

Part F. Hydrogen chloride gas was bubbled through an ice cooled solution of ethyl N-[4-[4-[(aminoiminomethyl) amino]phenyl]butyl]-N-[3-cyanophenyl]glycine (0.078 gm, 0.2 mmol) in 10 mLs ethanol under a nitrogen atmosphere for 20 minutes. The reaction flask was stoppered allowed to warm to ambient temperature and stir overnight. The reaction mixture was concentrated in vacuo to give the crude imidate as a colorless viscous oil. The oil was redissolved in 5 mLs ethanol and the ammoniun carbonate (0.062 gm, 0.8 mmol) was added. The reaction mixture was stirred at ambient temperature overnight and was concentrated to give the crude product as a white semisolid residue. The title compound was isolated after HPLC purification on Vydac C-18 column eluting with Solvent A (acetonitrile:water:TFA 80:20:0.2) and solvent B (water:TFA 99.8:2) using a gradient, as a semisolid 0.058 gms (71%). MS 206(M+2, 100%) HRMS calc 411.2509, found 411.2521 1H NMR (DMSO-d6): 9.5(s, 1H), 9.0(s<2H), 8.8(s, 2H), 7.35(t, 1H), 7.25(d, 2H), 7.2(s, 4H), 7.15(d, 2H), 7.0(d, 1H), 6.95(m, 2H), 4.2(s, 2H), 4.1(q, 2H), 3.4(m,2H), 2.6(m, 2H), 1.6(m, 4H), 1.2(t, 3H).

Example 102

Preparation of ethyl N-[3-(aminoiminomethyl) phenyl]-N-[4-(4-aminophenyl)butyl]glycine mono (trifluoroacetate)

Employing methods similar to Example 101 Part F, but using N-[4-[4-aminophenyl]butyl]-N-[3-cyanophenyl] glycine (0.12 gm, 0.34 mmol) the title compound was isolated after HPLC purification on Vydac C-18 column eluting with Solvent A (acetonitrile:water:TFA 80:20:0.2) and solvent B (water:TFA 99.8:2) using a gradient, as a semisolid 0.089 gms (70%) MS 369(M+H)+, 185(M+2H)+2 HRMS calc 369.2290, found 369.2298 1H NMR (DMSO-d6): 9.2(s, 2H), 9.1(s, 2H), 7.4(t, 1H), 7.3(d, 2H), 7.2(d, 2H), 7.0(d, 1H), 6.9(m, 2H), 4.2(s, 2H), 4.1(q, 2H), 3.4(m, 2H), 2.6(m, 2H), 1.6(m, 4H), 1.2(t, 3H).

Example 103

Preparation of N-[4-[4-[(aminoiminomethyl)amino] phenyl]butyl]-N-[3-(aminoiminomethyl)phenyl] glycine dihydrochloride Employing methods similar to Example 6 but using ethyl N-[4-[4-[(aminoiminomethyl)amino]phenyl]butyl]-N-[3-(aminoiminomethyl)phenyl]glycine bis(trifluoroacetate) (0.03 gm, 0.07 mmol) the title compound was isolated as a glassy solid 0.015 mg (56%) Mp>220° C. MS 383(m+H)+ HRMS calc 383.2194, found 383.2200 1H NMR (DMSO-d6): 9.8(s, 1H), 9.3(s, 2H), 9.0(s, 2H), 7.5(s, 4H), 7.4(t, 1H), 7.3(d, 2H), 7.2(d, 2H), 6.9–7.0(m,3H), 4.2(s, 2H), 3.4(m, 2H), 2.6(m, 2H), 1,6(m, 4H).

Example 104

Preparation of methyl N-[2-[4-[(aminoiminomethyl) amino]phenyl]ethyl]-N-[3-(aminoiminomethyl) phenyl]glycine bis(trifluoroacetate)

Part A. Employing methods similar to Example 101 Part B, but using 3-amino-benzonitrile (0.55 gm, 4.66 mmol) and 4-nitrophenethyl bromide (0.98 gm, 4.66 mmol) 1-(N-3-cyanophenyl)-2-(4-nitrophenyl)aminoethane was prepared as an oil 0.68 gm (55%). MS 268(M+H)+ 1H NMR (CDCl3): 8.2(d, 2H), 7.4(d, 2H), 7.1(m, 1H), 7.0(d, 1H), 6.8(m, 2H), 3.9(bs, 1H), 3.4(q, 2H), 3.0(d, 2H).

Part B. Employing methods similar to Example 101 Part C, but using 1-(N-3-cyanophenyl)-2-(4-nitrophenyl) aminoethane (0.30 gm, 1.12 mmol), ethyl N-[2-[4-nitrophenyl]ethyl]-N-[3-cyanophenyl]glycine was prepared as an oil 0.32 gm, (81%) MS 354(M+H)+ 1H NMR (CDCl3): 8.2(d, 2H), 7.4(d, 2H), 7.3(m, 1H), 7.0(d, 1H), 6.8(m, 2H), 4.2(q, 2H), 3.9(s, 2H), 3.7(t, 2H), 3.1(t, 2H), 1.3(t, 3H).

Part C. Employing methods similar to Example 101 Part D, but using ethyl N-[2-[4-nitrophenyl]ethyl]-N-[3-cyanophenyl]glycine (0.31 gm, 0.88 mmol), ethyl N-[2-[4-aminophenyl]ethyl]-N-[3-cyanophenyl]glycine was prepared as an oil 0.16 gm, (56%) MS 324(M+H)+ 1H NMR (CDCl3): 7.15(m, 1H), 7.0(d, 3H), 6.8(m, 2H), 6.6(d, 2H), 4.2(q, 2H), 3,9(s, 2H), 3.6(t, 2H), 2.8(t 2H), 1.2(t, 3H).

Part D. Employing methods similar to Example 13 but using ethyl N-[2-[4-aminophenyl]ethyl]-N-[3-cyanophenyl] glycine (0.15 gm, 0.46 mmol) the title compound was isolated after HPLC purification on Vydac C-18 column eluting with Solvent A (acetonitrile:water:TFA 80:20:0.2) and solvent B (water:TFA 99.8:2) using a gradient, as a semisolid 0.05 gm, (35%) Mp >220° C. MS 369(M+H)+, 185(M+2H)+2 HRMS calc 369.2039, found 369.2052 1H NMR (DMSO-d6): 9.8(s, 1H), 9.2(s, 2H), 7.5(s, 4H), 7.4(m, 3H), 7.2(d, 2H), 7.15(d, 1H), 6.9(m, 2H), 4.3(s, 2H), 3.7(s, 3H), 3.6(m, 2H), 2.9(m, 2H).

Example 105

Preparation of methyl N-[3-(aminoiminomethyl) phenyl]-N-[2-(4-aminophenyl)ethyl]glycine mono (trifluoroacetate)

Employing methods similar to Example 101 Part E but using ethyl N-[2-[4-aminophenyl]ethyl]-N-[3-cyanophenyl] glycine (0.12 gm, 0.37 mmol) the title compound was isolated after HPLC purification on Vydac C-18 column eluting with Solvent A (acetonitrile:water:TFA 80:20:0.2) and solvent B (water:TFA 99.8:2) using a gradient, as a semisolid 0.062 gm, (50%) Mp dec. 120° C. MS 327(M+H)+ HRMS calc 327.1821, found 327.1811 1H NMR (DMSO-d6): 9.2(s, 2H), 9.1(s, 2H), 7.4(m, 3H), 7.15(d, 2H), 7.0(d, 1H), 6.9(m, 2H), 4.2(s, 2H), 3.6(m, 5H), 2.9(t, 2H).

Example 106

Preparation of methyl N-[3-(aminoiminomethyl) phenyl]-N-[2-[4-(aminoiminomethyl)phenyl]ethyl] glycine bis(trifluoroacetate)

Part A. Employing methods similar to Example 101 part B, but using 4-cyano phenethyl bromide (0.443 gm, 2.11 mmol), 1-(N-3-cyanophenyl)-2-(4-cyanophenyl) aminoethane was prepared as an oil 0.355 gm, (68%) MS 265(M+H)+1 1H NMR (CDCl3): 7.6(d, 2H), 7.3(d, 2H), 7.2(m, 1H), 7.0(d, 1H), 6.8(m, 2H), 4.0(bs, 1H), 3.4(m, 2H), 3.0(t, 2H).

Part B. Employing methods similar to Example 101 Part C, but using 1-(N-3-cyanophenyl)-2-(4-cyanophenyl) aminoethane (0.15 gm, 0.61 mmol) and ethyl bromacetate (0.14 gm, 1.21 mmol), ethyl N-[2-[4-cyanophenyl]ethyl]-N-[3-cyanophenyl]glycine was prepared as an oil 0.085 gm, (41%) MS 334(M+H)+ 1H NMR (CDCl3): 7.6(d, 2H), 7.3 (m, 3H), 7.0(d, 1H), 6.8(m, 2H), 4.2(q, 2H), 3.9(s, 2H), 3.7(t, 2H), 3.0(t, 2H), 1.3(t, 3H).

Part C. Employing methods similar to Example 1 Part D, but using ethyl N-[2-[4-cyanophenyl]ethyl]-N-[3- cyanophenyl]glycine (0.083 gm, 0.25 mmol) the title compound was isolated after HPLC purification on Vydac C-18 column eluting with Solvent A (acetonitrile:water:TFA 80:20:0.2) and solvent B (water:TFA 99.8:2) using a gradient, as a semisolid 0.042 gm, (50%) Mp 245° C. MS 354(M+H)+ HRMS calc 354.1930 found 354.1922 $^1$H NMR (DMSO-d6): 9.2(d, 4H0, 9.0(d, 4H), 7.8(d, 2H), 7.6(d, 2H), 7.4(t, 1H), 7.1(d, 1H), 7.0(m, 2H), 4.3(s, 2H), 3.6(m,5H0, 3.0(t, 2H).

Example 107

Preparation of N-[3-(aminoiminomethyl)phenyl]-N-[2-[4-(aminoiminomethyl)phenyl]ethyl]glycine bis (hydrochloride)

Employing methods similar to Example 6 but using methyl N-[3-(aminoiminomethyl)phenyl]-N-[2-[4-(aminoiminomethyl)phenyl]ethyl]glycine bis (trifluoroacetate) (0.035 gm, 0.1 mmol) the title compound was isolated as a semisolid 0.017 gm, (51%) Mp>220° C. MS 340(M+H)+ HRMS calc 340.1774, found 340.1786 $^1$H NMR (DMSO-d6): 9.2(d, 4H), 9.1(d, 4H), 7.8(d, 2H), 7.6(d, 2H), 7.4(t, 1H), 7.0(m, 3H), 4.2(s, 2H), 3.6(m, 2H), 3.0(m, 2H).

Example 108

Preparation of methyl N-[3-(aminoiminomethyl) phenyl]-N-[2-phenylethyl]glycine mono (trifluoroacetate)

Part A. Employing methods similar to Example 101 part B, but using phenethyl bromide (0.29 gm, 2.11 mmol), 1-(N-3-cyanophenyl)-2-(phenyl)aminoethane was prepared as an oil 0.30 gm, (64%) MS 223(M+H)+ $^1$H NMR (CDCl$_3$): 7.3–7.5(m, 6H), 7.0(d, 1H), 6.8(m, 2H), 4.0(bs, 1H), 3.5(m, 2H), 3.0(t, 2H).

Part B. Employing methods similar to Example 101 Part C, but using 1-(N-3-cyanophenyl)-2-(phenyl)aminoethane (0.15 gm, 0.56 mmol) and ethyl bromoacetate (0.13 gm, 1.12 mmol), ethyl N-[2-phenethyl]-N-[3-cyanophenyl] glycine was prepared as an oil 0.175 gm, (100%) MS 309(M+H)+ $^1$H NMR (CDCl$_3$): 7.2–7.4(m, 6H), 7.0(d, 1H), 6.8(m, 2H), 4.2(q, 2H), 3.9(s, 2H), 3.6(t, 2H), 2.9(t, 2H).

Part C. Employing methods similar to Example 1 Part D, but using ethyl N-[2-phenethyl]-N-[3-cyanophenyl]glycine (0.175 gm, 0.57 mmol) the title compound was isolated after HPLC purification on Vydac C-18 column eluting with Solvent A (acetonitrile:water:TFA 80:20:0.2) and solvent B (water:TFA 99.8:2) using a gradient starting 20% A to 80% A over 20 minutes, as a semisolid 0.088 gm, (50%) Mp 145–7° C. MS 312(M+H)+ HRMS calc 312,1712, found 312.1703 $^1$H NMR (DMSO-d6): 9.2(s, 2H), 8.9(s, 2H), 7.4(t, 1H), 7.3(m, 4H), 7.2(m, 1H), 7.0(d, 1H), 6.9(m, 2H), 4.2(s, 2H), 3.6(m, 5H).

Example 109

Preparation of methyl 4-[[2-[4-[(aminoiminomethyl) amino]phenyl]ethyl][3 -(aminoiminomethyl)phenyl] amino]butanoate bis(trifluoroacetate)

Part A. Employing methods similar to Example 101 Part C, but using 1-(N-3-cyanophenyl)-2-(4-nitrophenyl) aminoethane (0.30 gm, 1.12 mmol) and 4-bromocrotonate (0.27 gm, 2.24 mmol) methyl 4-[[2-[4-nitrophenyl]ethyl][3-cyanophenyl]amino]-2-butenoate was prepared as an oil gm, MS 366(M+H)+, 383 (M+NH$_4$)+ $^1$H NMR (CDCl$_3$): 8.2(d, 2H), 7.4(d, 2H), 7.3(m, 1H), 7.0(d, 1H), 6.8(m, 2H), 5.8(m, 1H), 4.0(m, 2H), 3.75(s, 3H), 3.6(t, 2H), 3.0(t, 2H).

Part B. Employing methods similar to Example 101 Part D, but using methyl 4-[[2-[4-nitrophenyl]ethyl][3-cyanophenyl]amino]-2-butenoate (0.40 gm, 1.12 mmol), methyl 4-[[2-[4-aminophenyl]ethyl][3-cyanophenyl] amino]-butanoate was prepared as an oil 0.32 gm, (85%) MS 338(M+H)+ $^1$H NMR (CDCl$_3$): 7.2(m, 1H), 6.8–7.0(m, 5H), 6.8(d, 2H), 3.7(s,, 3H), 3.6(bs, 2H), 3.5(t, 2H), 3.2(t, 2H), 2.8(t, 2H), 2.3(t, 2H), 1.8(m, 2H).

Part C. Employing methods similar to Example 13, but using methyl 4-[[2-[4-aminophenyl]ethyl][3-cyanophenyl] amino]butanoate (0.10 gm, 0.3 mmol) the title compound was isolated after HPLC purification on Vydac C-18 column eluting with Solvent A (acetonitrile:water:TFA 80:20:0.2) and solvent B (water:TFA 99.8:2) using a gradient, as a semisolid 0.43 gm, (65%) Mp >200° C. HRMS calc 397.2352, found 397.2351 $^1$H NMR (DMSO-d6): 9.8(s, 1H), 9.2(s, 2H), 9.1(s, 1H), 7.5(bs, 4H), 7.4(m, 3H), 7.2(d, 2H), 7.0(m, 3H), 3.8(s, 3H), 3.75(m, 2H), 3.4(m, 2H), 2.8(m, 2H), 2.4(t, 2H), 1.8(m, 2H).

Example 110

Preparation of methyl 4-[[3-(aminoiminomethyl) phenyl][2-(4-aminophenyl)ethyl]amino]butanoate mono(trifluoroacetate)

Employing methods similar to Example 1 Part D, but using methyl 4-[[2-[4-aminophenyl]ethyl][3-cyanophenyl] amino]butanoate (0.20 gm, 0.59 mmol) the title compound was isolated after HPLC purification on Vydac C-18 column eluting with Solvent A (acetonitrile:water:TFA 80:20:0.2) and solvent B (water:TFA 99.8:2) using a gradient, as a semisolid 0.89 gm, (42%) MS 355(M+H)+ HRMS calc 355.2134, found 355.2119 $^1$H NMR (DMSO-d6): 9.2(s, 2H), 9.0(s, 2H), 7.4(d, 3H), 7.2(d, 2H), 7.0(m, 3H), 3.6(s, 3H), 3.5(t, 2H), 3.3(t, 2H), 2.8(t, 2H). 2.3(t, 2H), 1.8(m, 2H).

Example 111

Preparation of methyl 4-[[3-(aminoiminomethyl) phenyl][2-[4-(aminoiminomethyl)phenyl]ethyl] amino]-2-butenoate bis(trifluoroacetate)

Part A. Employing methods similar to Example 101 Part B, but using 3-amino-benzonitrile (0.79 gm, 6.67 mmol) and 4-cyano phenethyl bromide (1.4 gm, 6.67 mmol), 1-(N-3-cyanophenyl)-2-(4-cyanophenyl)aminoethane was prepared as an oil 1.4 gm, (85%). MS 365(M+NH$_4$)+ $^1$H NMR (CDCl$_3$): 7.6(d, 2H),, 7.3(d, 2H), 7.2(m, 1H), 7.0(d, 1H), 6.8(m, 2H), 3.9(bs, 1H), 3.4(q, 2H), 3.0(t, 2H).

Part B. Employing methods similar to Example 101 Part C, but using 1-(N-3-cyanophenyl)-2-(4-cyanophenyl) aminoethane (0.32 gm, 1.29 mmol) and methyl bromocrotonate (0.22 gm, 2.58 mmol), methyl 4-[[2-[4-cyanophenyl] ethyl][3-cyanophenyl]amino]-2-butenoate was prepared as an oil 0.37 gm, (82%) MS 363(M+NH$_4$)+ $^1$H NMR (CDCl$_3$): 7.6(d, 2H), 7.3 (m, 2H), 7.0(d, 1H), 6.8(m, 3H), 5.8(m, 1H), 4.9(m, 1H), 3.9(m, 2H), 3.75(s, 3H), 3.6(t, 2H), 3.0(t, 2H).

Part C. Employing methods similar to Example 101 Part F, but using methyl 4-[[2-[4-cyanophenyl]ethyl][3-cyanophenyl]amino]-2-butenoate (0.11 gm, 0.45 mmol), the title compound was isolated after HPLC purification on Vydac C-18 column eluting with Solvent A (acetonitrile:water:TFA 80:20:0.2) and solvent B (water:TFA 99.8:2) using a gradient, as a semisolid 0.085 gm, (50%) Mp >230° C. MS 380(M+H)+ HRMS calc 380.2086, found 380.2070 $^1$H NMR (DMSO-d6): 9.2(d, 4H), 9.0(bs, 4H), 7.8(d, 2H), 7.6(d, 2H), 7.4(t, 1H), 7.0(m, 3H), 6.8(m, 1H), 5.8(d, 1H), 4.2(m, 2H), 3.6(m, 5H), 3.0(m, 2H).

Example 112

Preparation of 4-[[3-(aminoiminomethyl)phenyl][2-[4-(aminoiminomethyl)phenyl]ethyl]amino]-2-butenoic acid bis(hydrochloride)

Employing methods similar to Example 6, but using methyl 4-[[3-(aminoiminomethyl)phenyl][2-[4-(aminoiminomethyl)phenyl]ethyl]amino]-2-butenoate bis (trifluoroacetate) (0.50 gm, 0.13 mmol), the title compound was isolated as a semisolid 0.035 gm, (95%). Mp >220° C. MS 366(M+H)$^+$ HRMS calc 366.1930, found 366.1933. $^1$H NMR (DMSO-d6): 9.2(bs, 4H), 9.1(d, 4H), 7.8(d, 2H), 7.6(d, 2H), 7.4(t, 1H), 7.0(m, 1H), 6.8(m, 1H), 5.8(d, 1H), 4.2(m, 2H), 3.6(m, 2H), 3.0(m, 2H).

Example 113

Preparation of methyl 4-[[3-(aminoiminomethyl) phenyl][2-[4-(aminoiminomethyl)phenyl]ethyl] amino]butanoate bis(trifluoroacetate)

Part A. Employing methods similar to Example 101 Part D, but using methyl 4-[[2-[4-cyanophenyl]ethyl][3-cyanophenyl]amino]-2-butenoate (0.20 gm, 0.58 mmol), methyl 4-[[2-[4-cyanophenyl]ethyl][3-cyanophenyl] amino]-butanoate was prepared as an oil 0.19 gm, (95%). MS 348(M+H)$^+$ $^1$H NMR (CDCl$_3$): 7.6(d, 2H), 7.3(m, 3H), 6.9(m, 3H), 3.7(s, 3H), 3.6(t, 2H), 3.2(t, 2H), 2.9(t, 2H), 2.3(t, 2H), 1.8(m,2H).

Part B. Employing methods similar to Example 1 Part D, but using methyl 4-[[2-[4-cyanophenyl]ethyl][3-cyanophenyl]amino]-butanoate (0.12 gm, 0.36 mmol), the title compound was isolated after HPLC purification on Vydac C-18 column eluting with Solvent A (acetonitrile:water:TFA 80:20:0.2) and solvent B (water:TFA 99.8:2) using a gradient, as a semisolid 0.050 gm, (36%) Mp >220° C. MS 382(M+H)$^+$ HRMS calc 382.2243, found 382.2256 $^1$H NMR (DMSO-d6); 9.3(s, 2H), 9.2(s, 2H), 9.1 (s, 2H), 9.0(s, 2H), 7.8(d, 2H), 7.6(d, 2H), 7.4(t, 1H), 7.0(m, 3H), 3.6(m, 5H), 3.4(m, 2H), 3.0(m, 2H), 2.4(t, 2H), 1.8(m, 2H).

Example 114

Preparation of 3-[[3-(aminomethyl)phenyl][4-(4-aminophenyl)butyl]amino]-1-propanol Part A. Carbon tetrabromide (34.01 gm, 102.55 mmol), pyridine (8.3 mL, 102.55 mmol) and triphenylphosphine (25.52 gm, 112.55 mmole) were added sequentially to a solution of 4-(4-nitrophenyl) butanol (20.0 gm, 102.55 mmol) in 400 mL of CH$_2$Cl$_2$ (precooled to 0° C.) and was allowed to stir overnight with warming to room temperature. The volatiles were removed under vacuum and the residue dissolved in ethyl acetate, filtered through a plug of silica and concentrated to dryness. The resulting oil was purified by flash chromatography eluting hexane:ethyl acetate(v:v, 4:1) to give 4-(4-nitrophenyl)butyl bromide as an oil 23.51 gm (88%). $^1$H NMR (CDCl$_3$) 1.95–1.81 (m, 4H), 2.78 (t, 2H), 3.45 (t, 2H), 7.37 (d, 2H), 8.15 (d, 2H).

Part B. Sodium bicarbonate (13.91 gm, 165.60 mmole), 3-aminobenzonitrile (9.78 gm, 82.80 mmol) and 2 mL of the phase transfer agent tris[2-(2-methoxyethoxyethyl]amine (TDA-1) were added sequentially to 4-(4-nitrophenyl)butyl bromide (23.51 gm, 91.08 mmol) and heated to 80° C. for 4 hours. The cooled solution was poured through a plug of silica gel, rinsed with 200 mL of EtOAc and concentrated to dryness. The resulting oil was purified by flash chromatography (hexane/EtOAc, 3:1)to give (N-4-(4-nitro)butyl)-3-aminobenzonitrile as a yellow oil that slowly solidified upon standing 19.9 gm (74%). $^1$H NMR (CDCl$_3$) 1.85–1.63 (m, 4H), 2.80 (m, 2H), 3.17 (m, 2H), 4.10 (br, 1H), 6. 80 (m, 2H), 6.95 (d, 1H), 7.22 (t, 1H), 7.34, (d, 2H), 8.14 (d, 2H).

Part C. Potassium bicarbonate (2.10 gm, 20.99 mmol) and allyl bromide (1.8 mL, 20.99 mmol) were added sequentially to a solution of (N-4-(4-nitro)butyl)-3-aminobenzonitrile (3.1 gm, 10.49 mmol) in 2 mL of TDA-1 and heated to 60° C. for 3 hrs. The solution was allowed to cool to room temperature, diluted with 50 mL of ethyl acetate, filtered through a pad of silica gel and concentrated to dryness. The resulting oil was purified by flash chromatography (hexane/EtOAc, 2:1)to give N-Allyl, N-4(4-nitrophenyl)butyl-3-aminobenzonitrile as an oil 2.75 gm (78%) MS m/e 336 (M+H)$^+$ $^1$H NMR (CD$_3$OD) 1.76–1.64 (m, 4H), 2.78 (t, 2H), 3.36 (t, 2H), 3.94 (s, 2H), 5.10 (d, 1H), 5.81 (dm, 1H), 6.84 (br s, 2H), 6.91 (d, 1H), 7.24 (t, 1H), 7.42 (d, 2H), 8.10 (d, 2H).

Part D. N-Allyl, N-4(4-nitrophenyl)butyl-3-aminobenzonitrile (1.95 gm, 5.8 mmol) was dissolved in 60 mL of THF, followed by the addition of 21.1 mL of borane-THF complex (1 M, 26.1 mmol) and heated at 40° C. for 1 hour. This was followed by the addition of 5 mL of distilled water and 11.63 g (75.6 mmol) of sodium perborate and allowed to stir at room temperature overnight. The solution was then acidified with dilute HCl to pH 2, heated at reflux for 10 minutes and neutralized with aqueous sodium bicarbonate. The organics were extracted with EtOAc, washed with brine (2×), dried over MgSO$_4$, filtered through a pad of silica and dried. The resulting oil was purified by flash chromatography eluting ethyl acetate to give 3-[[3-cyanophenyl][4-(4-nitrophenyl)butyl]amino]-1-propanol as a viscous oil 1.4 gm (68%). MS m/e 354.2 (M+H)$^+$ $^1$H NMR (CDCl$_3$) 1.84–1.52 (br m, 6H), 1.84–1.71 (br m, 2H) 3.22 (dm, 2H), 3.40 (dm, 2H), 3.69 (s, 2H), 6.86 (d, 2H), 7.43–7.19 (br m, 4H), 8.09 (d, 2H).

Part E. 3-[[3-cyanophenyl][4-(4-nitrophenyl)butyl] amino]-1-propanol (1.4 gm, 3.96 mmol) was dissolved in 25 mL of methanol, followed by the addition of 0.14 gm of 20% Pd(OH)$_2$/C and placed under a balloon of hydrogen for 2.5 hours. The resulting solution was filtered through a pad of celite and the volatiles removed under vacuum to give the title compound as a clear semi-solid 1.30 gm, (100%) MS m/e 328.3 (M+H)$^+$ $^1$H NMR (CD$_3$OD) 1.60 (br s, 4H), 1.78 (m, 2H), 2.54 (br s, 2H), 3.32 (s, 2H), 3.42 (t, 2H), 3.62 (t, 2H), 3.99 (s, 2H), 6.71–6.62 (m, 5 H), 6.93 (d, 2H), 7.20 (t, 1H).

Example 115

Preparation of methyl N-[3-(aminoiminomethyl) phenyl]-N-[3-(4-aminophenyl)propyl]glycine bis (trifluoroacetate)

Part A. 3-aminobenzonitrile (7.00 gm, 59.25 mmol) and 4-nitrocinnamaldehyde (12.59 gm, 71.10 mmol) were dissolved in 150 mL of methanol, after stirring at room temperature for 10 minutes, 1 mL of acetic acid and sodium cyanoborohydride (3.72 gm,59.25 mmol) were added sequentially and the resulting solution allowed to stir overnight. The resulting solids were filtered off, washed (3×)

with hexane (50 mL) and dried under vacuum to give N-(4-Nitrophenyl-2-propenyl)-3-aminobenzonitrile as a yellow solid 7.75 gm, (57%). MS m/e 280 (M+H)$^+$ $^1$H NMR (DMSO-d6) 3.93 (s, 2H), 6.65–6.50 (m, 3H), 6.89 (br s, 2H), 7.20 (t, 1H), 7.65 (d, 2H), 8.15 (d, 2H).

Part B. Employing methods similar to Example 114 Part B, but using N-(4-Nitrophenyl-2-propenyl)-3-aminobenzonitrile (3.5 gm, 12.53 mmol) and methylbromoacetate (1.2 mL (12.53 mmol), N-methyl acetate, N-(4-(4-nitrophenypropenyl))-3-aminobenzonitrile was prepared as a yellow brown oil 3.66 gm, (83%). MS m/e 352 (M+H)$^+$ $_1$H NMR (CDCl$_3$) 3.75 (s, 3H), 4.13 (s, 2H), 4.24 (d, 2H), 6.44 (dt, 1H), 6.60 (d, 1H), 6.88 (br s, 2H), 7.02 (d, 2H), 7.28 (t, 1H), 7.45 (d, 2H), 8.14 (d, 2H).

Part C. Employing methods similar to Example 114 Part E, but using N-methyl acetate, N-(4-(4-nitrophenypropenyl))-3-aminobenzonitrile (3.66 gm, 10.41 mmol), N-methyl acetate, N-(4-(4-aminophenypropyl))-3-aminobenzonitrile was prepared as a clear oil 3.36 gm, (100%). MS m/e 324.3 (M+H)$^+$ $^1$H NMR (CDCl$_3$) 1.89 (m, 2H0, 2.55 (t, 2H), 3.34 (t, 2H), 3.61 (br, 2H) 3.72 (s, 3H), 4.01 (s, 2H), 6.73–6.61 (m, 4H), 6.99–6.92 (m, 3H), 7.21 (t, 1H).

Part D. Employing methods similar to Example 1 Part D, but using N-methyl acetate, N-(4-(4-Aminophenypropyl))-3-aminobenzonitrile (1.045 gm, 3.23 mmol) the title compound was isolated after HPLC purification on a Vydac C-18 column eluting Solvent A (acetonitrile:water:TFA 80:20:0.2) and solvent B (water:TFA 99.8:0.2) using a gradient, as a light brown semi-solid. MS m/e 341.2 (M+H)$^+$ $^1$H NMR (CDCl$_3$) 1.82 (t, 2H), 2.53 (t, 2H), 3.22 (m, 2H), 3.25 (s, 2H), 3.63 (s, 3H), 4.00 (br, 3H), 6.46 (s, 1H), 6.62 (s, 1H), 6.84 (s, 1H), 6.96 (2H), 7.09 (d, 2H), 7.17 (t, 1H).

Example 116

Preparation of methyl N-[3-(aminocarbonyl) phenyl]-N-[3-(4-aminophenyl)propyl]glycine mono (trifluoroacetate)

Employing methods similar to Example 1 Part D, but using N-methyl acetate, N-(4-(4-Aminophenypropyl))-3-aminobenzonitrile (1.045 gm, 3.23 mmol) the title compound was isolated after HPLC purification on a Vydac C-18 column eluting Solvent A (acetonitrile:water:TFA 80:20:0.2) and solvent B (water:TFA 99.8:0.2) using a gradient, as a light brown semi-solid. MS m/e 342.2 (M+H)$^+$.

Example 117

Preparation of methyl N-[3-(aminoiminomethyl) phenyl]-N-[3-[2'-(aminosulfonyl)[1,1'-biphenyl]-4-yl]propyl]glycine mono(trifluoroacetate)

Part A. 4-bromobenzaldehyde (9.11 gm, 49.28 mmol) and (triphenylphosphoranylidene) acetaldehyde (15.00 gm, 49.28 mmol) were combined in 250 mL of methylene chloride and stirred overnight at room temperature. The volatiles were removed under vacuum and the residue dissolved in 200 mL of EtOAc, filtered through a pad of silica gel and concentrated to dryness. The resulting residue was purified by flash chromatography on silica gel eluting hexane:ethyl acetate (3:1, v:v) to give 3-(4-bromophenyl) acrolein as a pale yellow solid 3.67 gm, (35%). MS m/e 211 (M+H)$^+$ $^1$H NMR (CDCl$_3$) 6.70 (dd, 1H), 7.43 (m, 3H), 7.54 (d, 2H), 9.69 (d, 1H).

Part B. 3-aminobenzonitrile (2.05 gm, 17.38 mmol) and 3-(4-bromophenyl) acrolein (3.67 gm, 17.38 mmol) were dissolved in 100 mL of methanol. After stirring at room temperature for 10 minutes, 1 mL of acetic acid and sodium cyanoborohydride (1.09 gm 17.38 mmol) were added sequentially and the resulting solution allowed to stir overnight at room temperature. The solution was acidified to pH 2 with 10% HCl and was made basic (pH 10) with sat. Na$_2$CO$_3$. The volatiles were removed under vacuum and the residue dissolved in 200 mL of EtOAc and washed (3×) with brine (50 mL). The organics were dried over MgSO$_4$, filtered through a pad of silica gel and concentrated to dryness to N-(4-bromophenyl-3-propenyl)-3-aminobenzonitrile as an off white solid 4.99 gm,(91%). MS m/e 313.1 (M+H)$^+$ $^1$H NMR (CDCl$_3$) 3.92 (d, 2H), 4.20 (br, 1H), 6.28 (dt, 1H), 6.52 (d, 2H), 6.84 (br s, 2H), 6.99 (d, 1H), 7.24 (m, 3H), 7.45 (d, 2H).

Part C. Employing methods similar to Example 114 Part B, but using N-(4-bromophenyl-3-propenyl)-3-aminobenzonitrile (4.99 gm, 15.93 mmol) and methylbromoacetate (1.60 gm, 19.12 mmol) N-methyl acetate, N-(4-bromophenyl-3-propenyl)-3-aminobenzonitrile was prepared as an oil 3.29 gm, (54%) MS m/e 387 (M+H)$^+$ $^1$H NMR (CDCl$_3$) 3.74 (s, 3H), 4.09 (s, 2H), 4.13 (d, 2H), 6.23 (dt, 1H), 6.50 (d, 1H), 6.88 (m, 2H), 7.00 (d, 1H), 7.20 (d, 2H), 7.26 (t, 1H), 7.41 (d, 2H).

Part D. N-methyl acetate, N-(4-bromophenyl-3-propenyl)-3-aminobenzonitrile (1.69 gm, 4.38 mmol), tetrakis(triphenylphosphine)-palladium (0)(0.253, 0.2 mmol), tetrabutylammonium bromide (0.14 gm, 0.4 mmol), Na$_2$CO$_3$, (0.93 gm, 8.77 mmol) and 2[[(1,1-dimethylethyl) amino]sulfonyl])phenyl boric acid (1.35 gm, 5.26 mmol) were combined sequentially in 40 mL of 4:1 toluene/H$_2$O and stirred at reflux for 4 hrs. The solution was then concentrated to dryness and the residue purified by flash chromatography on silica gel eluting hexane:ethyl acetate (3:2, v:v) to give methyl N-[3-cyanophenyl]-N-[3-[2'-(N-t-butlysulfonylamide)[1,1'-biphenyl]-4-yl]-2-propenyl] glycine as an oil 2.05 gm, (90%) MS m/e 518.3 (M+H)$^+$ $^1$H NMR (CDCl$_3$) 1.33 (s, 9H), 3.78 (s, 3H), 4.13 (s, 2H), 4.22 (d, 2H), 6.33 (dt, 1H), 6.61 (d, 1H), 6.91 (br s, 2H), 7.02 (d, 1H), 7.30 (m, 2H), 7.46 (m, 5H), 7.50 (t, 1H), 8.14 (d, 1H).

Part E. Employing methods similar to Example 114 Part E, but using methyl N-[3-cyanophenyl]-N-[3-[2'-[[(1,1-dimethylethyl)amino]sulfonyl][1,1'-biphenyl]-4-yl]-2-propenyl]glycine (2.05 gm, 3.95 mmol), methyl N-[3-cyanophenyl]-N-[3-2'-[[(1,1-dimethylethyl)amino]sulfonyl] [1,1'-biphenyl]-4-yl]-propyl]glycine was prepared as a clear oil 0.7 gm, (34%). MS m/e 520.4 (M+H)$^+$ $^1$H NMR (CDCl$_3$) 1.19 (s, 9H), 2.02 (t, 2H), 2.70 (t, 2H), 3.42, (t, 2H), 3.73, (s, 3H), 4.05 (s, 2H), 6.78 (br s, 2H), 6.99 (d, 1H), 7.27 (m, 3H), 7.47 (m, 3H), 7.54 (t, 1H), 7.90 (d, 1H), 8.13 (d, 1H).

Part F. Employing methods similar to Example 1 Part D, but using methyl N-[3-cyanophenyl]-N-[3-[2'-[[(1,1-dimethylethyl)amino]sulfonyl][1,1'-biphenyl]-4-yl]propyl] glycine (0.70 gm, 1.34 mmol) the title compound was isolated after HPLC purification on a Vydac C-18 column eluting Solvent A (acetonitrile:water:TFA 80:20:0.2) and solvent B (water:TFA 99.8:0.2) using a gradient, as a light brown semi-solid. MS m/e 481.2 (M+H)$^+$.

Example 118

Preparation of methyl N-[3-(aminoiminomethyl) phenyl]-N-[3-[2'-[[(1,1-dimethylethyl)amino] sulfonyl][1,1'-biphenyl]-4-yl]propyl]glycine mono (trifluoroacetate)

Employing methods similar to Example 1 Part D, but using methyl N-[3-cyanophenyl]-N-[3-[2'-[[(1,1- dimethylethyl)amino]sulfonyl])[1,1'-biphenyl]-4-yl]propyl] glycine (0.70 gm, 1.34 mmol) the title compound was isolated after HPLC purification on a Vydac C-18 column eluting Solvent A (acetonitrile:water:TFA 80:20:0.2) and solvent B (water:TFA 99.8:0.2) using a gradient, as a light brown semi-solid. MS m/e 537.3 (M+H)$^+$.

Example 119

Prepartation of methyl N-[3-(aminoiminomethyl) phenyl]-N-[2-[2'-(aminosulfonyl)[1,1'-biphenyl]-4-yl]ethyl]glycine mono(trifluoroacetate)

Part A. Employing method similar to Example 114 Part A but using 4-bromophenethylalcohol (5.0 gm, 24.9 mmol) 4-bromophenethylbromide was prepared as a clear oil. $^1$H NMR (CDCl$_3$): 3.15 (t, 2H), 3.58 (t, 2H), 7.10 (d, 2H), 7.45 (d, 2H).

Part B. Employing methods similar to Example 114 Part B, but using 3-aminobenzonitrile (3.09 gm, 26.14 mmol) and 4-bromophenethylbromide (6.90 gm, 26.16 mmol) N-(4-bromophenyl)ethyl-3-aminobenzonitrile was prepared as a light yellow solid 6.52 gm (83%).

Part C. Employing methods similar to Example 114 Part B, but using N-(4-bromophenyl)ethyl-3-aminobenzonitrile 6.52 gm (21.65 mmol) and methylbromoacetate (2.46 mL, 25.98 mmol), methyl N-[3-cyanophenyl]-N-[2-[2-bromophenyl]ethyl]glycine was prepared as an oil 2.66 gm (33%). MS m/e 375.1 (M+H)$^+$ $^1$H NMR (CDCl$_3$): 2.85 (t, 2H), 3.59 (t, 2H), 3.70 (s, 3H), 3.90, (s, 2H), 6.80 (br s, 2H), 6.96, (d, 1H), 7.07, (d, 2H), 7.38 (t, 1H), 7.40 (d, 2H).

Part D. Employing methods similar to Example 114 Part D, but using methyl N-[3-cyanophenyl]-N-[2-[2-bromophenyl]ethyl]glycine (1.72 gm, 4.63 mmol) and 2[[(1,1-dimethylethyl)amino]sulfonyl]phenyl boric acid (1.43 gm, 5.26 mmol), methyl N-[3-cyanophenyl]-N-[2-[2'-[[(1,1-dimethylethyl)amino]sulfonyl][1,1'-biphenyl]-4-yl]ethyl] glycine was prepared as an oil 1.69 gm (89%) MS m/e 506.3 (M+H)$^+$ $^1$H NMR (CDCl$_3$): 0.97 (s, 9H), 2.97 (t, 2h), 3.66 (t, 2H), 3.73 (s, 3H), 3.99 (s, 2H), 6.82 (s, 2H), 6.99 (s, 1H), 7.28 (d, 4H), 7.46, (m, 3H), 7.54 (t, 1H), 8.15 (d, 1H).

Part D. Employing methods similar to Example 1 Part D, but using methyl N-[3-cyanophenyl]-N-[2-[2'-[[(1,1-dimethylethyl)amino]sulfonyl][1,1'-biphenyl]-4-yl]ethyl] glycine (1.69 gm, 4.12 mmol) the title compound was isolated after HPLC purification on a Vydac C-18 column eluting Solvent A (acetonitrile:water:TFA 80:20:0.2) and solvent B (water:TFA 99.8:0.2) using a gradient, as a light brown semi-solid. MS.m/e 467.2 (M+H)$^+$.

Example 120

Preparation of methyl N-[3-(aminoiminomethyl) phenyl]-N-[2-[2'-[[(1,1-dimethylethyl)amino] sulfonyl][1,1'-biphenyl]-4-yl]ethyl]glycine mono (trifluoroacetate)

Employing methods similar to Example 1 Part D, but using methyl N-[3-cyanophenyl]-N-[2-[2'-[[(1,1-dimethylethyl)amino]sulfonyl][1,1'-biphenyl]-4-yl]ethyl] glycine (1.69 gm, 4.12 mmol) the title compound was isolated after HPLC purification on a Vydac C-18 column eluting Solvent A (acetonitrile:water:TFA 80:20:0.2) and solvent B (water:TFA 99.8:0.2) using a gradient, as a light brown semi-solid. MS.m/e 523.3 (M+H)$^+$.

Example 121

Preparation of 2-[[3-(aminoiminomethyl)phenyl][4-(4-aminophenyl)butyl]amino]acetamide bis (trifluoroacetate)

Part A. methyl 2-[[3-cyanophenyl][4-(4-nitrophenyl) butyl]amino]glycine (9.05 gm, 24.63 mmol) was dissolved in 150 mL of 3:1 MeOH/H$_2$O containing lithium hydroxide (2.06 gm, 49.26 mmol) and stirred at room temperature for 4 hrs. The solution was dissolved in 250 mL of ethyl acetate, acidified with 10% HCl (pH 2) and washed 2× with 150 mL of brine. The organic were dried over MgSO$_4$, filtered and concentrated to dryness and the solids washed with 100 mL of hot hexane to yield 2-[[3-cyanophenyl][4-(4-nitrophenyl) butyl]amino]glycine acid as a light yellow solid (8.26 gm, 95%). MS m/e 354.2 (M+H)$^+$ $^1$H NMR (CDCl$_3$) 1.70 (m, 4H), 2.77 (t, 2H), 3.39 (t, 4H), 4.11 (s, 2H), 6.81 (m, 2H), 7.01 (d, 1H), 7.26 (m, 1H), 7.31 (d, 2H), 8.14 (d, 2H).

Part B. 2-[[3-cyanophenyl][4-(4-nitrophenyl)butyl] amino]glycine acid (3.2 gm, 9.0 mmol), N-methyl morpholine (2.2 mL, 19.92 mmol) and isobutylchloroformate (1.2 mL, 9.0 mmol) were added sequentially to 300 mL of precooled (−78° C.) CH$_2$Cl$_2$. After stirring at that temperature for 1 hr., 22.6 mL of NH$_3$ (2.0 M in MeOH, 45.28 mmol) was slowly added via syringe and allowed to continue stirring for 2 hrs. while warming to room temperature. The volatiles were removed under vacuum, dissolved in 400 mL of EtOAc, washed sequentially with 150 mL of: 10% HCl, brine, sat. Na$_2$CO$_3$ and brine. The organics were dried over MgSO$_4$, filtered through a plug of silica gel and concentrated to dryness to give 2-[[3-cyanophenyl][4-(4-nitrophenyl)butyl]amino]acetamide as a light yellow solid 2.43 gm (77%). MS m/e 353.2 (M+H)+ $^1$H NMR (CD$_3$OD) 1.67 (m, 4H), 2.78 (t, 2h), 3.45 (t, 2H), 3.94 (s, 2H), 6.95–6.86 (m, 3H), 7.28 (t, 1H), 7.43(d, 2H), 8.11 (d, 2H).

Part C. Employing methods similar to Example 114 Part E, but using 2-[[3-cyanophenyl][4-(4-nitrophenyl)butyl] amino]acetamide (2.43 gm, 6.89 mmol), 2-[[3-cyanophenyl] [4-(4-aminophenyl)butyl]amino]acetamide was prepared as a clear oil 2.54 gm (100%) MS m/e 323.2 (M+H)$^+$ $^1$H NMR (CDCl$_3$) 1.57 (br s, 4H), 2.51 (m, 2H), 3.30 (m, 2H), 3.62 (br, 2H), 3.79 (s, 2H), 6.30 (s, 1H), 6.61 (d, 2H), 6.80 (m, 2H), 6.91 (d, 2H), 7.23 (t, 1H).

Part D. Employing methods similar to Example 1 Part D, but using 2-[[3-cyanophenyl][4-(4-aminophenyl)butyl] amino]acetamide (2.23 gm, 6.89 mmol) the title compound was isolated after HPLC purification on a Vydac C-18 column eluting Solvent A (acetonitrile:water:TFA 80:20:0.2) and solvent B (water:TFA 99.8:0.2) using a gradient, as a light brown semi-solid. MS m/e 170.7 (M+2H)$^{2+}$.

Example 122

Preparation of 3-[(2-amino-2-oxoethyl)[4-(4-aminophenyl)butyl]amino]benzamide mono (trifluoroacetate)

Employing methods similar to Example 1 Part D, but using 2-[[3-cyanophenyl][4-(4-aminophenyl)butyl]amino] acetamide (2.23 gm, 6.89 mmol) the title compound was isolated after HPLC purification on a Vydac C-18 column eluting Solvent A (acetonitrile:water:TFA 80:20:0.2) and solvent B (water:TFA 99.8:0.2) using a gradient, as a light brown semi-solid. MS m/e 341.3 (M+H)$^+$.

Example 201

Preparation of 1-(N-3-aminoimnomethyl)phenyl-N-[4-(4-aminophenyl)butyl]aminopropane tris (trifluoroacetate)

Part A. Employing methods similar to Example 101 Part C, but using 1-(N-3-cyanophenyl)-4-(4-nitrophenyl) aminobutane (3.1 gm, 10.49 mmol) and allyl bromide (2.54 gm, 20.99 mmol), 1 -(N-3-cyanophenyl)-2-(4-nitrophenyl) allyl amine was isolated as an oil, 2.74 gm (78%). MS m/e 336 (M+H)$^+$.

Part B. Employing methods similar to Example 101 Part D, but using 1-(N-3-cyanophenyl)-2-(4-nitrophenyl) allylamine (1.72 gm, 5.12 mmol), 1-(N-3-cyano)phenyl-[4-(4-aminophenyl)butyl]amino-propane was isolated as an oil, 1.41 gm (97%). MS m/e 308.3 (M+H)$^+$.

Part C. Employing methods similar to example 101 Part F, but using 1-(N-3-cyano)phenyl-[4-(4-aminophenyl)butyl] aminopropane (1.41 gm, 5.0 mmol), the title compound was isolated after HPLC purification on Vydac C-18 column eluting with solvent A (acetonitrile:water:TFA 80:20:0.2) and solvent B (water:TFA 99.8:0.2) as a gradient, as a white solid. MS m/e 325.3 (M+H)$^+$.

Example 202

Preparation of N-[3-(aminoiminomethyl)phenyl)-N-[2-[2'-(aminosulfonyl)[1,1'-biphenyl]-4-yl]propyl]-N-2-(hydroxy)ethylamine Part A. Employing methods similar to example 121 Part A, but using methyl N-[3-(cyano)phenyl]-N-[2-[2'-(1,1-dimethylethylaminosulfonyl)[1,1'-biphenyl]-4-yl]propyl] glycine (2.96 gm, 6.38 mmol), N-[3-(cyano)phenyl]-N-[2-[2'-(dimethylethylaminosulfonyl)[1,1'-biphenyl]-4-yl] propyl]glycine acid was isolated as an off white solid 1.25 gm, (44%). MS m/e 450.2 (M+H)$^+$.

Part B. N-[3-(cyano)phenyl]-N-[2-[2'-(1,1-dimethylethylaminosulfonyl)[1,1'-biphenyl]-4-yl]propyl] glycine acid (1.62 gm, 3.60 mmol) and TEA (0.36 gm, 0.50 mL, 3.60 mmol) were dissolved in 100 mL of anhydrous THF and cooled to -15° C. followed by the addition of isobutylchloroformate (0.492 gm, 0.47 mL, 3.60 mmol) and stirred for 15 min. The solution was filtered under a stream of dry nitrogen and the solids washed with an additional 50 mL of anhydrous THF. The solution was cooled to -15° C. and sodium borohydride (dissolved in 4 mL of distilled water) was added slowly over the course of 5 min. The cooled solution was allowed to stir for 30 min, warmed to room temperature and stirred for an additional hour. The solution was slowly quenched with 10% HCl and the solution diluted with 200 mL of ethylacetate. The organics were washed twice with brine (100 mL), dried over MgSO$_4$, filtered through a plug of silica and the volatiles removed in vacuum to give N-[3-(cyano)phenyl]-N-[2-[2'-(1,1-dimethylethylaminosulfonyl)[1,1'-biphenyl]-4-yl]propyl]-N-2-(hydroxy)ethylamine as a semisolid (1.2 gm, 76%). MS m/e 436.2 (M+H)$^+$.

Part C. Employing methods similar to example 101 Part F, but using N-[3 (cyano)phenyl]-N-[2-[2'-(aminosulfonyl) [1,1'-biphenyl]-4-yl]propyl]]-N-2-(hydroxy)ethylamine (1.2 gm, 2.75 mmol), the title compound was isolated after HPLC purification on Vydac C-18 column eluting with solvent A (acetonitrile:water:TFA 80:20:0.2) and solvent B (water:TFA 99.8:0.2) using a gradient, as a white solid. MS m/e 453.2 (M+H)$^+$.

Example 203

Preparation of N-[3-(aminoiminomethyl)phenyl]-N-[2-[2'-(aminosulfonyl)[1,1'-biphenyl]-4-yl]propyl]-N-2-(phenylthio)ethylamine Part A. N-[3 (cyano)phenyl]-N-[2-[2'-dimethylethylaminosulfonyl-1,1'-biphenyl-4-yl]propyl]-N-2-hydroxyethylamine (0.600 gm, 1.22 mmol) was dissolved in anhydrous CH$_2$Cl$_2$ followed by the addition of triphenylphosphine (0.455 gm, 1,73 mmol) and diethylazodicarboxylate (0.30 gm, 0.273 mL, 1.73 mmol). The solution was stirred for 10 min followed by the addition of thiophenol (0.19 gm, 0.18 mL, 1.73 mmol) and stirred overnight at room temperature. The volatiles were removed in vacuo and the residue purified by silica gel chromatography eluting with ethylacetate:hexane (v:v, 50:50) to give N-[2 -(cyano) phenyl]-N-[2-[2'-(1,1-dimethylethylaminosulfonyl)[1,1'-biphenyl]-4-yl]propyl]-N-2-(phenylthio)ethylamine as a pale yellow semisolid (0.500 gm, 76%) MS m/e 584.4 (M+H)$^+$.

Part B. Employing methods similar to example 101 Part F, but using N-[2-(cyano)phenyl]-N-[2-[2'-(1,1-dimethylethylaminosulfonyl)[1,1'-biphenyl]-4-yl]propyl]-N-2-(phenylthio)ethylamine (0.500 gm, 0.856 mmol), the title compound was isolated after HPLC purification on Vydac C-18 column eluting with solvent A (acetonitrile:water:TFA, 80:20:0.2) and solvent B (water:TFA 99.8:0.2) used as a gradient, as an off white solid. MS m/e 545.4 (M+H)$^+$.

Example 204

Preparation of N-[3-(aminoiminomethyl)phenyl]-N-[2-[2'-(aminosulfonyl)[1,1'-biphenyl]-4-yl]propyl]-N-2-(phenoxy)ethylamine Part A. Employing methods similar to Example (203) Part A, but using phenol (0.136 gm, 1.44 mmol), N-[3-(cyano) phenyl]-N-[2-[2'(1,1-dimethylethylaminosulfonyl)[1,1'-biphenyl]-4-yl]propyl]-N-2-(phenoxy)ethylamine was obtained as a semisolid (0.722 gm, 82%). MS m/e 568.3 (M+H)$^+$.

Part B. Employing methods similar to Example 101 Part F, but using N-[3-(cyano)phenyl]-N-[2-[2'(1,1-dimethylethylaminosulfonyl)-1,1'-biphenyl-4-yl]propyl]-N-2-(phenoxy)ethylamine (0.41 gm, 0.722 mmol), the title compound was isolated after HPLC purification on Vydac C-18 column eluting with solvent A (acetonitrile:water:TFA, 80:20:0.2) and solvent B (water:TFA 99.8:0.2) used as a gradient, as an off white solid. MS m/e 529.3 (M+H)$^+$.

Example 205

Preparation of N-[3-(aminoiminomethyl)phenyl]-N-[2-[2'-(aminosulfonyl)[1,1'-biphenyl]-4-yl]propyl]-N-2-(methoxy)ethylamine Part A. N-[3-(cyano)phenyl]-N-[2-[2'-(1,1-dimethylethylaminosulfonyl)[1,1'-biphenyl]-4-yl]propyl]-N-2-(hydroxy)ethylamine (1.00 gm, 2.89 mmol) was dissolved in 100 mL of anhydrous THF followed by the addition of NaH (60% dispersion in mineral oil, 0.23 gm, 5.78 mmol). Once the evolution of gas ceased, iodomethane was added (0.411, 0.18 mL, 2.89 mmol) and the solution was allowed to stir overnight at room temperature. The solution was quenched with dilute HCl, and the volatiles removed in vacuum. N-[3-(Cyano)phenyl]-N-[2-[2'-(1,1-dimethylethylaminosulfonyl)[1,1'-biphenyl]-4-yl]propyl]-N-2-(methoxy)ethylamine was isolated after HPLC purification on Vydac C-18 column eluting with solvent A (acetonitrile:water:TFA 80:20:0.2) and solvent B (water:TFA 99.8:0.2) used as a gradient, as a clear oil (0.100 gm, 7%). MS m/e 506.4 (M+H)$^+$.

Part B. Employing methods similar to Example 101 Part F, but using N-[3-(cyano)phenyl]-N-[2-[2'-(1,1-dimethylethylaminosulfonyl)[1,1'-biphenyl]-4-yl]propyl]-N-2-(methoxy)ethylamine (0.100 gm, 0.197 mmol), the title compound was isolated after HPLC purification on Vydac C-18 column eluting with solvent A (acetonitrile:water:TFA,

Example 206

Preparation of N-[3-(aminoiminomethyl)phenyl]-N-[2-[2'-(aminosulfonyl)[1,1'-biphenyl]-4-yl]propyl]-N-2-(phenylaminocarbamato)ethylamine Part A. N-[3-(cyano)phenyl]-N-[2-[2'-(1,1-dimethylethylaminosulfonyl)[1,1'-biphenyl]-4-yl]propyl]-N-2-(hydroxy)ethylamine (0.220 gm, 0.637 mmol), diisopropylethylamine (0.330 gm, 0.44 mL, 2.55 mmol) and phenylisocyanate (0.228 gm, 0.21 mL, 1.91 mmol) were combined in 100 mL of toluene and refluxed overnight. The volatiles were removed in vacuo and the residue dissolved in 200 mL of ethylacetate and washed with 10% HCl (100 mL), the organics were dried over $MgSO_4$ filtered through a plug of silica gel and the volatiles removed to afford N-[3-(cyano)phenyl]-N-[2-[2'-(1,1-dimethylethylaminosulfonyl)[1,1'-biphenyl]-4-yl]propyl]-N-2-(phenylaminocarbamato)ethylamine (0.20 gm, 51%). MS m/e 611.5 $(M+H)^+$.

Part B. Employing methods similar to example 101 Part F, but using N-[3-(cyano)phenyl]-N-[2-[2'-(1,1-dimethylethylaminosulfonyl)[1,1'-biphenyl]-4-yl]propyl]-N-2-(phenylaminocarbamato)ethylamine (0.20 gm, 0.327 mmol), the title compound was isolated after HPLC purification on Vydac C-18 column eluting with solvent A (acetonitrile:water:TFA, 80:20:0.2) and solvent B (water:TFA 99.8:0.2) used as a gradient, as a tan solid. MS m/e 336 $(M+H)^+$ 572.4.

TABLE 1A

| Ex | D | Z | B | p | R |
|---|---|---|---|---|---|
| 1 | m-Am | $(CH_2)_2$ | p-Am | 1 | $OCH_3$ |
| 2 | m-Am | $(CH_2)_2$ | p-Am | 1 | $OCH_3$ |
| 3 | m-Am | $(CH_2)_2$ | p-Am | 1 | $OCH_3$ |
| 4 | m-Am | $(CH_2)_2$ | p-C(O)$NH_2$ | 1 | $OCH_3$ |
| 5 | m-Am | $(CH_2)_2$ | p-$C_6H_5$ | 1 | $OCH_3$ |
| 6 | m-Am | $(CH_2)_2$ | p-Am | 1 | OH |
| 7 | m-Am | $(CH_2)_2$ | p-Am | 1 | $OCH(CH_3)_2$ |
| 8 | m-Am | $(CH_2)_2$ | p-Am | 1 | $OC_2H_5$ |
| 9 | m-Am | $(CH_2)_2$ | p-Am | 1 | $NHCH_2CH_2Ph$ |
| 10 | m-Am | $(CH_2)_2$ | p-$NH_2$ | 1 | $OCH_3$ |
| 11 | m-Am | $(CH_2)_2$ | p-$NHSO_2C_6H_5$ | 1 | $OCH_3$ |
| 12 | m-Am | $(CH_2)_2$ | p-$NHSO_2CH_3$ | 1 | $OCH_3$ |
| 13 | m-Am | $(CH_2)_2$ | p-Guan | 1 | $OCH_3$ |
| 14 | m-Guan | $(CH_2)_2$ | p-Am | 1 | $OCH_3$ |
| 15 | m-Am | $(CH_2)_4$ | p-Guan | 1 | $OCH_3$ |
| 16 | m-Am | $(CH_2)_4$ | p-$NH_2$ | 1 | $OCH_3$ |
| 17 | m-Am | $(CH_2)_2$ | m-Am | 1 | $OCH_3$ |
| 18 | m-Am | $(CH_2)_2$ | p-$CO_2CH_3$ | 1 | $OCH_3$ |
| 19 | m-Guan | $(CH_2)_2$ | p-Guan | 1 | $OCH_3$ |
| 20 | m-Am | $OCH_2$ | p-Am | 1 | $OC_2H_5$ |
| 21 | m-Am | NHC=$OCH_2$ | m-Guan | 1 | $OC_2H_5$ |
| 22 | m-Am | $OCH_2$ | p-Am | 2 | $OCH_3$ |
| 23 | m-Am | $(CH_2)_2$ | p-Am | 1 | $NHOCH_3$ |
| 24 | m-Am | $(CH_2)_2$ | p-Am | 1 | $NHCH_2CO_2CH_3$ |
| 25 | m-Am | $(CH_2)_2$ | p-Am | 1 | $NHCH_3$ |
| 26 | m-Am | $(CH_2)_2$ | p-Am | 1 | $NC_4H_8$ |
| 27 | p-Am | $(CH_2)_2$ | m-Am | 1 | $OC_2H_5$ |
| 28 | p-Am | $(CH_2)_2$ | m-Am | 1 | OH |
| 29 | p-Am | $(CH_2)_2$ | p-Am | 1 | $OC_2H_5$ |
| 30 | m-Am | $NHSO_2$ | p-Am | 1 | $OC_2H_5$ |
| 31 | m-Am | $NHSO_2$ | p-$CH_3$ | 1 | $OC_2H_5$ |
| 32 | m-Am | $OCH_2$ | p-H | 1 | $OCH_3$ |

TABLE 1B

| Ex | D | Z | B | A' | A" | p | R |
|---|---|---|---|---|---|---|---|
| 101 | m-Am | $(CH_2)_4$ | p-Guan | CH | CH | 1 | $OC_2H_5$ |
| 102 | m-Am | $(CH_2)_4$ | p-$NH_2$ | CH | CH | 1 | $OC_2H_5$ |
| 103 | m-Am | $(CH_2)_4$ | p-Guan | CH | CH | 1 | OH |
| 104 | m-Am | $(CH_2)_2$ | p-Guan | CH | CH | 1 | $OCH_3$ |
| 105 | m-Am | $(CH_2)_2$ | p-$NH_2$ | CH | CH | 1 | $OCH_3$ |
| 106 | m-Am | $(CH_2)_2$ | p-Am | CH | CH | 1 | $OCH_3$ |
| 107 | m-Am | $(CH_2)_2$ | p-Am | CH | CH | 1 | OH |
| 108 | m-Am | $(CH_2)_2$ | p-H | CH | CH | 1 | $OCH_3$ |
| 109 | m-Am | $(CH_2)_2$ | p-Guan | CH | CH | 2 | $OCH_3$ |
| 110 | m-Am | $(CH_2)_2$ | p-$NH_2$ | CH | CH | 2 | $OCH_3$ |
| 111 | m-Am | $(CH_2)_2$ | p-Am | CH | CH | * | $OCH_3$ |
| 112 | m-Am | $(CH_2)_2$ | p-Am | CH | CH | * | OH |
| 113 | m-Am | $(CH_2)_2$ | p-Am | CH | CH | 2 | $OCH_3$ |
| 115 | m-Am | $(CH_2)_4$ | p-$NH_2$ | CH | CH | 1 | $OCH_3$ |
| 116 | m-C=$ONH_2$ | $(CH_2)_3$ | p-$NH_2$ | CH | CH | 1 | $OCH_3$ |
| 117 | m-Am | $(CH_2)_3$ | p-(2-$SO_2NH_2$)Ph | CH | CH | 1 | $OCH_3$ |
| 118 | m-C=$ONH_2$ | $(CH_2)_3$ | p-(2-$SO_2NH_2$)Ph | CH | CH | 1 | $OCH_3$ |
| 119 | m-Am | $(CH_2)_2$ | p-(2-$SO_2NH_2$)Ph | CH | CH | 1 | $OCH_3$ |
| 120 | m-Am | $(CH_2)_3$ | p-(2-$SO_2$NH-t-Bu)Ph | CH | CH | 1 | $OCH_3$ |
| 121 | m-Am | $(CH_2)_4$ | p-$NH_2$ | CH | CH | 1 | $NH_2$ |
| 122 | m-C=$ONH_2$ | $(CH_2)_4$ | p-$NH_2$ | CH | CH | 1 | $NH_2$ |
| 123 | m-Am | $(CH_2)_2$ | p-(2-$SO_2CH_3$)Ph | CH | CH | 1 | $OC_2H_5$ |
| 124 | m-Am | $(CH_2)_2$ | p-(2-$SO_2CF_3$)Ph | CH | CH | 1 | $OCH_3$ |
| 125 | m-C=$ONH_2$ | $(CH_2)_2$ | p-(2-$CF_3$)Ph | CH | CH | 1 | $OC_2H_5$ |
| 126 | m-Am | $(CH_2)_2$ | p-(2-$SO_2NH_2$)Ph | N | CH | 1 | $OC_2H_5$ |
| 127 | m-Am | $(CH_2)_3$ | p-(2-$SO_2NH_2$)Ph | N | CH | 1 | OH |
| 128 | m-Am | $(CH_2)_2$ | p-(2-$SO_2NH_2$)Ph | N | CH | 1 | $OCH_3$ |
| 129 | m-C=$ONH_2$ | $(CH_2)_3$ | p-(2-$SO_2NH_2$)Ph | N | CH | 1 | OH |
| 130 | m-C=$ONH_2$ | $(CH_2)_2$ | p-(2-$SO_2NH_2$)Ph | N | CH | 1 | $OCH_3$ |
| 131 | m-C=$ONH_2$ | $(CH_2)_3$ | p-(2-$SO_2NH_2$)Ph | N | CH | 1 | $NH_2$ |
| 132 | m-Am | $(CH_2)_2$ | p-(2-$SO_2CH_3$)Ph | N | CH | 1 | $OC_2H_5$ |
| 133 | m-Am | $(CH_2)_3$ | p-(2-$SO_2CH_3$)Ph | N | CH | 1 | OH |
| 134 | m-Am | $(CH_2)_3$ | p-(2-$SO_2CH_3$)Ph | N | CH | 1 | $OCH_3$ |
| 135 | m-C=$ONH_2$ | $(CH_2)_3$ | p-(2-$SO_2CH_3$)Ph | N | CH | 1 | OH |
| 136 | m-C=$ONH_2$ | $(CH_2)_3$ | p-(2-$SO_2CH_3$)Ph | N | CH | 1 | $OCH_3$ |
| 137 | m-C=$ONH_2$ | $(CH_2)_3$ | p-(2-$SO_2CH_3$)Ph | N | CH | 1 | $NH_2$ |
| 138 | m-Am | $(CH_2)_2$ | p-(2-$SO_2CF_3$)Ph | N | CH | 1 | $OC_2H_5$ |
| 139 | m-Am | $(CH_2)_3$ | p-(2-$SO_2CF_3$)Ph | N | CH | 1 | OH |

TABLE 1B-continued

![Structure: R-C(=O)-(CH2)p-N(phenyl-D)-Z-[ring with A', A'', B]]

| Ex | D | Z | B | A' | A" | p | R |
|---|---|---|---|---|---|---|---|
| 140 | m-Am | (CH₂)₂ | p-(2-SO₂CF₃)Ph | N | CH | 1 | OCH₃ |
| 141 | m-C=ONH₂ | (CH₂)₃ | p-(2-SO₂CF₃)Ph | N | CH | 1 | OH |
| 142 | m-C=ONH₂ | (CH₂)₂ | p-(2-SO₂CF₃)Ph | N | CH | 1 | OCH₃ |
| 143 | m-C=ONH₂ | (CH₂)₃ | p-(2-CF₃)Ph | N | CH | 1 | NH₂ |
| 144 | m-Am | (CH₂)₂ | p-(2-CF₃)Ph | N | CH | 1 | OC₂H₅ |
| 145 | m-Am | (CH₂)₃ | p-(2-CF₃)Ph | N | CH | 1 | OH |
| 146 | m-Am | (CH₂)₂ | p-(2-CF₃)Ph | N | CH | 1 | OCH₃ |
| 147 | m-C=ONH₂ | (CH₂)₃ | p-(2-CF₃)Ph | N | CH | 1 | OH |
| 148 | m-C=ONH₂ | (CH₂)₂ | p-(2-CF₃)Ph | N | CH | 1 | OCH₃ |
| 149 | m-C=ONH₂ | (CH₂)₃ | p-(2-CF₃)Ph | N | CH | 1 | NH₂ |
| 150 | m-Am | (CH₂)₂ | p-(2-SO₂NH₂)Ph | N | N | 1 | OC₂H₅ |
| 151 | m-Am | (CH₂)₃ | p-(2-SO₂NH₂)Ph | N | N | 1 | OH |
| 152 | m-Am | (CH₂)₂ | p-(2-SO₂NH₂)Ph | N | N | 1 | OCH₃ |
| 153 | m-C=ONH₂ | (CH₂)₃ | p-(2-SO₂NH₂)Ph | N | N | 1 | OH |
| 154 | m-C=ONH₂ | (CH₂)₂ | p-(2-SO₂NH₂)Ph | N | N | 1 | OCH₃ |
| 155 | m-C=ONH₂ | (CH₂)₃ | p-(2-SO₂NH₂)Ph | N | N | 1 | NH₂ |
| 156 | m-Am | (CH₂)₂ | p-(2-SO₂CH₃)Ph | N | N | 1 | OC₂H₅ |
| 157 | m-Am | (CH₂)₃ | p-(2-SO₂CH₃)Ph | N | N | 1 | OH |
| 158 | m-Am | (CH₂)₂ | p-(2-SO₂CH₃)Ph | N | N | 1 | OCH₃ |
| 159 | m-C=ONH₂ | (CH₂)₃ | p-(2-SO₂CH₃)Ph | N | N | 1 | OH |
| 160 | m-C=ONH₂ | (CH₂)₂ | p-(2-SO₂CH₃)Ph | N | N | 1 | OCH₃ |
| 161 | m-C=ONH₂ | (CH₂)₃ | p-(2-SO₂CH₃)Ph | N | N | 1 | NH₂ |
| 162 | m-Am | (CH₂)₂ | p-(2-SO₂CF₃)Ph | N | N | 1 | OC₂H₅ |
| 163 | m-Am | (CH₂)₃ | p-(2-SO₂CF₃)Ph | N | N | 1 | OH |
| 164 | m-Am | (CH₂)₂ | p-(2-SO₂CF₃)Ph | N | N | 1 | OCH₃ |
| 165 | m-C=ONH₂ | (CH₂)₃ | p-(2-SO₂CF₃)Ph | N | N | 1 | OH |
| 166 | m-C=ONH₂ | (CH₂)₂ | p-(2-SO₂CF₃)Ph | N | N | 1 | OCH₃ |
| 167 | m-C=ONH₂ | (CH₂)₃ | p-(2-CF₃)Ph | N | N | 1 | NH₂ |
| 168 | m-Am | (CH₂)₂ | p-(2-CF₃)Ph | N | N | 1 | OC₂H₅ |
| 169 | m-Am | (CH₂)₃ | p-(2-CF₃)Ph | N | N | 1 | OH |
| 170 | m-Am | (CH₂)₂ | p-(2-CF₃)Ph | N | N | 1 | OCH₃ |
| 171 | m-C=ONH₂ | (CH₂)₃ | p-(2-CF₃)Ph | N | N | 1 | OH |
| 172 | m-C=ONH₂ | (CH₂)₂ | p-(2-CF₃)Ph | N | N | 1 | OCH₃ |
| 173 | m-C=ONH₂ | (CH₂)₃ | p-(2-CF₃)Ph | N | N | 1 | NH₂ |
| 174 | m-Am | (CH₂)₂ | p-(2-SO₂NH₂)Ph | CF | CH | 1 | OC₂H₅ |
| 175 | m-Am | (CH₂)₃ | p-(2-SO₂NH₂)Ph | CF | CH | 1 | OH |
| 176 | m-Am | (CH₂)₂ | p-(2-SO₂NH₂)Ph | CF | CH | 1 | OCH₃ |
| 177 | m-C=ONH₂ | (CH₂)₃ | p-(2-SO₂NH₂)Ph | CF | CH | 1 | OH |
| 178 | m-C=ONH₂ | (CH₂)₂ | p-(2-SO₂NH₂)Ph | CF | CH | 1 | OCH₃ |
| 179 | m-C=ONH₂ | (CH₂)₃ | p-(2-SO₂NH₂)Ph | CF | CH | 1 | NH₂ |
| 180 | m-Am | (CH₂)₂ | p-(2-SO₂CH₃)Ph | CF | CH | 1 | OC₂H₅ |
| 181 | m-Am | (CH₂)₃ | p-(2-SO₂CH₃)Ph | CF | CH | 1 | OH |
| 182 | m-Am | (CH₂)₂ | p-(2-SO₂CH₃)Ph | CF | CH | 1 | OCH₃ |
| 183 | m-C=ONH₂ | (CH₂)₃ | p-(2-SO₂CH₃)Ph | CF | CH | 1 | OH |
| 184 | m-C=ONH₂ | (CH₂)₂ | p-(2-SO₂CH₃)Ph | CF | CH | 1 | OCH₃ |
| 185 | m-C=ONH₂ | (CH₂)₃ | p-(2-SO₂CH₃)Ph | CF | CH | 1 | NH₂ |
| 186 | m-Am | (CH₂)₂ | p-(2-SO₂CF₃)Ph | CF | CH | 1 | OC₂H₅ |
| 187 | m-Am | (CH₂)₃ | p-(2-SO₂CF₃)Ph | CF | CH | 1 | OH |
| 188 | m-Am | (CH₂)₂ | p-(2-SO₂CF₃)Ph | CF | CH | 1 | OCH₃ |
| 189 | m-C=ONH₂ | (CH₂)₃ | p-(2-SO₂CF₃)Ph | CF | CH | 1 | OH |
| 190 | m-C=ONH₂ | (CH₂)₂ | p-(2-SO₂CF₃)Ph | CF | CH | 1 | OCH₃ |
| 191 | m-C=ONH₂ | (CH₂)₃ | p-(2-CF₃)Ph | CF | CH | 1 | NH₂ |
| 192 | m-Am | (CH₂)₂ | p-(2-CF₃)Ph | CF | CH | 1 | OC₂H₅ |
| 193 | m-Am | (CH₂)₃ | p-(2-CF₃)Ph | CF | CH | 1 | OH |
| 194 | m-Am | (CH₂)₂ | p-(2-CF₃)Ph | CF | CH | 1 | OCH₃ |
| 195 | m-C=ONH₂ | (CH₂)₃ | p-(2-CF₃)Ph | CF | CH | 1 | OH |
| 196 | m-C=ONH₂ | (CH₂)₂ | p-(2-CF₃)Ph | CF | CH | 1 | OCH₃ |
| 197 | m-C=ONH₂ | (CH₂)₃ | p-(2-CF₃)Ph | CF | CH | 1 | NH₂ |

*p = CH₂CH=CH

TABLE 2

![Structure: Y-(CH2)p-N(phenyl-D)(phenyl-Z-phenyl-B)]

| Ex | D | Z | B | p | Y |
|---|---|---|---|---|---|
| 201 | m-Am | (CH₂)₄ | p-NH₂ | 3 | H |
| 202 | m-Am | (CH₂)₃ | p-(2-SO₂NH₂)C₆H₅ | 2 | HO |
| 203 | m-Am | (CH₂)₃ | p-(2-SO₂NH₂)C₆H₅ | 2 | C₆H₅S |
| 204 | m-Am | (CH₂)₃ | p-(2-SO₂NH₂)C₆H₅ | 2 | C₆H₅O |
| 205 | m-Am | (CH₂)₃ | p-(2-SO₂NH₂)C₆H₅ | 2 | OCH3 |
| 206 | m-Am | (CH₂)₃ | p-(2-SO₂NH₂)C₆H₅ | 2 | C₆H₅NHC(O)O |
| 207 | m-Am | (CH₂)₃ | p-(2-SO₂NH₂)C₆H₅ | 2 | H |
| 208 | m-Am | (CH₂)₃ | p-(2-SO₂NH₂)C₆H₅ | 2 | OH |
| 209 | m-Am | (CH₂)₃ | p-(2-SO₂NH₂)C₆H₅ | 2 | C₆H₅S |
| 210 | m-Am | (CH₂)₃ | p-(2-SO₂NH₂)C₆H₅ | 2 | SCH₃ |
| 211 | m-Am | (CH₂)₃ | p-(2-SO₂NH₂)C₆H₅ | 2 | OCH₃ |
| 212 | m-Am | (CH₂)₃ | p-(2-SO₂NH₂)C₆H₅ | 2 | C₆H₅O |
| 213 | m-Am | (CH₂)₃ | p-(2-SO₂NH₂)C₆H₅ | 2 | N(H)CH₃ |
| 214 | m-Am | (CH₂)₃ | p-(2-SO₂NH₂)C₆H₅ | 2 | N(CH₃)₂ |
| 215 | m-Am | (CH₂)₃ | p-(2-SO₂NH₂)C₆H₅ | 2 | C₆H₅NC(O)O |
| 216 | m-Am | (CH₂)₃ | p-(2-SO₂NH₂)C₆H₅ | 2 | C₆H₅ |
| 217 | m-Am | (CH₂)₃ | p-(2-SO₂NH₂)C₆H₅ | 3 | H |
| 218 | m-Am | (CH₂)₃ | p-(2-SO₂NH₂)C₆H₅ | 3 | OH |
| 219 | m-Am | (CH₂)₃ | p-(2-SO₂NH₂)C₆H₅ | 3 | C₆H₅S |
| 220 | m-Am | (CH₂)₃ | p-(2-SO₂NH₂)C₆H₅ | 3 | SCH₃ |
| 221 | m-Am | (CH₂)₃ | p-(2-SO₂NH₂)C₆H₅ | 3 | OCH₃ |
| 222 | m-Am | (CH₂)₃ | p-(2-SO₂NH₂)C₆H₅ | 3 | C₆H₅O |
| 223 | m-Am | (CH₂)₃ | p-(2-SO₂NH₂)C₆H₅ | 3 | N(H)CH₃ |
| 224 | m-Am | (CH₂)₃ | p-(2-SO₂NH₂)C₆H₅ | 3 | N(CH₃)₂ |
| 225 | m-Am | (CH₂)₃ | p-(2-SO₂NH₂)C₆H₅ | 3 | C₆H₅NC(O)O |
| 226 | m-Am | (CH₂)₃ | p-(2-SO₂NH₂)C₆H₅ | 3 | C₆H₅ |
| 227 | m-Am | (CH₂)₃ | p-(2-SO₂CH₃)C₆H₅ | 2 | H |
| 228 | m-Am | (CH₂)₃ | p-(2-SO₂CH₃)C₆H₅ | 2 | OH |
| 229 | m-Am | (CH₂)₃ | p-(2-SO₂CH₃)C₆H₅ | 2 | C₆H₅S |
| 230 | m-Am | (CH₂)₃ | p-(2-SO₂CH₃)C₆H₅ | 2 | SCH₃ |
| 231 | m-Am | (CH₂)₃ | p-(2-SO₂CH₃)C₆H₅ | 2 | OCH₃ |
| 232 | m-Am | (CH₂)₃ | p-(2-SO₂CH₃)C₆H₅ | 2 | C₆H₅O |
| 233 | m-Am | (CH₂)₃ | p-(2-SO₂CH₃)C₆H₅ | 2 | N(H)CH₃ |
| 234 | m-Am | (CH₂)₃ | p-(2-SO₂CH₃)C₆H₅ | 2 | N(CH₃)₂ |
| 235 | m-Am | (CH₂)₃ | p-(2-SO₂CH₃)C₆H₅ | 2 | C₆H₅NC(O)O |
| 236 | m-Am | (CH₂)₃ | p-(2-SO₂CH₃)C₆H₅ | 2 | C₆H₅ |
| 237 | m-Am | (CH₂)₃ | p-(2-SO₂CH₃)C₆H₅ | 3 | H |
| 238 | m-Am | (CH₂)₃ | p-(2-SO₂CH₃)C₆H₅ | 3 | OH |
| 239 | m-Am | (CH₂)₃ | p-(2-SO₂CH₃)C₆H₅ | 3 | C₆H₅S |
| 240 | m-Am | (CH₂)₃ | p-(2-SO₂CH₃)C₆H₅ | 3 | SCH₃ |
| 241 | m-Am | (CH₂)₃ | p-(2-SO₂CH₃)C₆H₅ | 3 | OCH₃ |
| 242 | m-Am | (CH₂)₃ | p-(2-SO₂CH₃)C₆H₅ | 3 | C₆H₅O |
| 243 | m-Am | (CH₂)₃ | p-(2-SO₂CH₃)C₆H₅ | 3 | N(H)CH₃ |
| 244 | m-Am | (CH₂)₃ | p-(2-SO₂CH₃)C₆H₅ | 3 | N(CH₃)₂ |
| 245 | m-Am | (CH₂)₃ | p-(2-SO₂CH₃)C₆H₅ | 3 | C₆H₅NC(O)O |
| 246 | m-Am | (CH₂)₃ | p-(2-SO₂CH₃)C₆H₅ | 3 | C₆H₅ |
| 247 | m-Am | (CH₂)₃ | p-(2-CF₃)C₆H₅ | 2 | H |
| 248 | m-Am | (CH₂)₃ | p-(2-CF₃)C₆H₅ | 2 | OH |
| 249 | m-Am | (CH₂)₃ | p-(2-CF₃)C₆H₅ | 2 | C₆H₅S |
| 250 | m-Am | (CH₂)₃ | p-(2-CF₃)C₆H₅ | 2 | SCH₃ |
| 251 | m-Am | (CH₂)₃ | p-(2-CF₃)C₆H₅ | 2 | OCH₃ |
| 252 | m-Am | (CH₂)₃ | p-(2-CF₃)C₆H₅ | 2 | C₆H₅O |
| 253 | m-Am | (CH₂)₃ | p-(2-CF₃)C₆H₅ | 2 | N(H)CH₃ |
| 254 | m-Am | (CH₂)₃ | p-(2-CF₃)C₆H₅ | 2 | N(CH₃)₂ |
| 255 | m-Am | (CH₂)₃ | p-(2-CF₃)C₆H₅ | 2 | C₆H₅NC(O)O |
| 256 | m-Am | (CH₂)₃ | p-(2-CF₃)C₆H₅ | 2 | C₆H₅ |
| 257 | m-Am | (CH₂)₃ | p-(2-CF₃)C₆H₅ | 3 | H |
| 258 | m-Am | (CH₂)₃ | p-(2-CF₃)C₆H₅ | 3 | OH |
| 259 | m-Am | (CH₂)₃ | p-(2-CF₃)C₆H₅ | 3 | C₆H₅S |
| 260 | m-Am | (CH₂)₃ | p-(2-CF₃)C₆H₅ | 3 | SCH₃ |
| 261 | m-Am | (CH₂)₃ | p-(2-CF₃)C₆H₅ | 3 | OCH₃ |
| 262 | m-Am | (CH₂)₃ | p-(2-CF₃)C₆H₅ | 3 | C₆H₅O |
| 263 | m-Am | (CH₂)₃ | p-(2-CF₃)C₆H₅ | 3 | N(H)CH₃ |

TABLE 2-continued

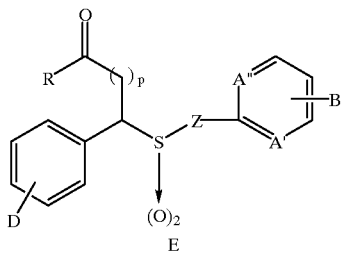

| Ex | D | Z | B | p | Y |
|---|---|---|---|---|---|
| 264 | m-Am | (CH$_2$)$_3$ | p-(2-CF$_3$)C$_6$H$_5$ | 3 | N(CH$_3$)$_2$ |
| 265 | m-Am | (CH$_2$)$_3$ | p-(2-CF$_3$)C$_6$H$_5$ | 3 | C$_6$H$_5$NC(O)O |
| 266 | m-Am | (CH$_2$)$_3$ | p-(2-CF$_3$)C$_6$H$_5$ | 3 | C$_6$H$_5$ |

Additional representative compounds are shown in Table 3. Each of Examples 301–392 are intended to correspond to each of formulae A–G.

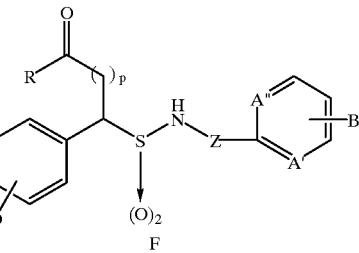

A

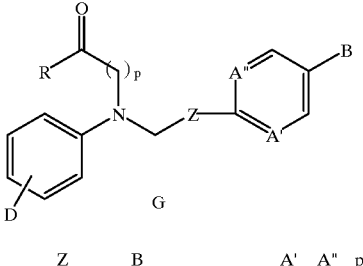

B

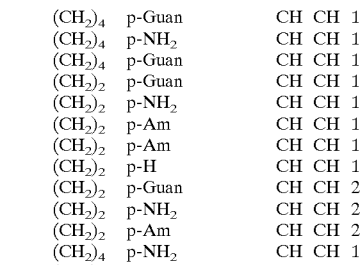

C

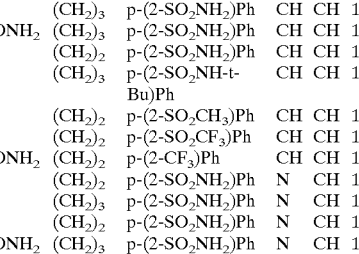

D

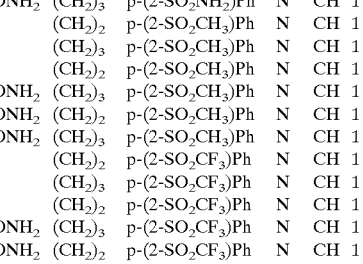

E

F

G

| Ex | D | Z | B | A' | A" | p | R |
|---|---|---|---|---|---|---|---|
| 301 | m-Am | (CH$_2$)$_4$ | p-Guan | CH | CH | 1 | OC$_2$H$_5$ |
| 302 | m-Am | (CH$_2$)$_4$ | p-NH$_2$ | CH | CH | 1 | OC$_2$H$_5$ |
| 303 | m-Am | (CH$_2$)$_4$ | p-Guan | CH | CH | 1 | OH |
| 304 | m-Am | (CH$_2$)$_2$ | p-Guan | CH | CH | 1 | OCH$_3$ |
| 305 | m-Am | (CH$_2$)$_2$ | p-NH$_2$ | CH | CH | 1 | OCH$_3$ |
| 306 | m-Am | (CH$_2$)$_2$ | p-Am | CH | CH | 1 | OCH$_3$ |
| 307 | m-Am | (CH$_2$)$_2$ | p-Am | CH | CH | 1 | OH |
| 308 | m-Am | (CH$_2$)$_2$ | p-H | CH | CH | 1 | OCH$_3$ |
| 309 | m-Am | (CH$_2$)$_2$ | p-Guan | CH | CH | 2 | OCH$_3$ |
| 310 | m-Am | (CH$_2$)$_2$ | p-NH$_2$ | CH | CH | 2 | OCH$_3$ |
| 311 | m-Am | (CH$_2$)$_2$ | p-Am | CH | CH | 2 | OCH$_3$ |
| 312 | m-Am | (CH$_2$)$_4$ | p-NH$_2$ | CH | CH | 1 | OCH$_3$ |
| 313 | m-C=ONH$_2$ | (CH$_2$)$_3$ | p-NH$_2$ | CH | CH | 1 | OCH$_3$ |
| 314 | m-Am | (CH$_2$)$_3$ | p-(2-SO$_2$NH$_2$)Ph | CH | CH | 1 | OCH$_3$ |
| 315 | m-C=ONH$_2$ | (CH$_2$)$_3$ | p-(2-SO$_2$NH$_2$)Ph | CH | CH | 1 | OCH$_3$ |
| 316 | m-Am | (CH$_2$)$_2$ | p-(2-SO$_2$NH$_2$)Ph | CH | CH | 1 | OCH$_3$ |
| 317 | m-Am | (CH$_2$)$_3$ | p-(2-SO$_2$NH-t-Bu)Ph | CH | CH | 1 | OCH$_3$ |
| 318 | m-Am | (CH$_2$)$_3$ | p-(2-SO$_2$CH$_3$)Ph | CH | CH | 1 | OC$_2$H$_5$ |
| 319 | m-Am | (CH$_2$)$_2$ | p-(2-SO$_2$CF$_3$)Ph | CH | CH | 1 | OCH$_3$ |
| 320 | m-C=ONH$_2$ | (CH$_2$)$_2$ | p-(2-CF$_3$)Ph | CH | CH | 1 | OC$_2$H$_5$ |
| 321 | m-Am | (CH$_2$)$_2$ | p-(2-SO$_2$NH$_2$)Ph | N | CH | 1 | OC$_2$H$_5$ |
| 322 | m-Am | (CH$_2$)$_2$ | p-(2-SO$_2$NH$_2$)Ph | N | CH | 1 | OH |
| 323 | m-Am | (CH$_2$)$_3$ | p-(2-SO$_2$NH$_2$)Ph | N | CH | 1 | OCH$_3$ |
| 324 | m-C=ONH$_2$ | (CH$_2$)$_3$ | p-(2-SO$_2$NH$_2$)Ph | N | CH | 1 | OH |
| 325 | m-C=ONH$_2$ | (CH$_2$)$_2$ | p-(2-SO$_2$NH$_2$)Ph | N | CH | 1 | OCH$_3$ |
| 326 | m-C=ONH$_2$ | (CH$_2$)$_2$ | p-(2-SO$_2$NH$_2$)Ph | N | CH | 1 | NHCH$_3$ |
| 327 | m-Am | (CH$_2$)$_2$ | p-(2-SO$_2$CH$_3$)Ph | N | CH | 1 | OC$_2$H$_5$ |
| 328 | m-Am | (CH$_2$)$_3$ | p-(2-SO$_2$CH$_3$)Ph | N | CH | 1 | OH |
| 329 | m-Am | (CH$_2$)$_2$ | p-(2-SO$_2$CH$_3$)Ph | N | CH | 1 | OCH$_3$ |
| 330 | m-C=ONH$_2$ | (CH$_2$)$_3$ | p-(2-SO$_2$CH$_3$)Ph | N | CH | 1 | OH |
| 331 | m-C=ONH$_2$ | (CH$_2$)$_2$ | p-(2-SO$_2$CH$_3$)Ph | N | CH | 1 | OCH$_3$ |
| 332 | m-C=ONH$_2$ | (CH$_2$)$_2$ | p-(2-SO$_2$CH$_3$)Ph | N | CH | 1 | NHCH$_3$ |
| 333 | m-Am | (CH$_2$)$_2$ | p-(2-SO$_2$CF$_3$)Ph | N | CH | 1 | OC$_2$H$_5$ |
| 334 | m-Am | (CH$_2$)$_3$ | p-(2-SO$_2$CF$_3$)Ph | N | CH | 1 | OH |
| 335 | m-Am | (CH$_2$)$_2$ | p-(2-SO$_2$CF$_3$)Ph | N | CH | 1 | OCH$_3$ |
| 336 | m-C=ONH$_2$ | (CH$_2$)$_3$ | p-(2-SO$_2$CF$_3$)Ph | N | CH | 1 | OH |
| 337 | m-C=ONH$_2$ | (CH$_2$)$_3$ | p-(2-SO$_2$CF$_3$)Ph | N | CH | 1 | OCH$_3$ |
| 338 | m-C=ONH$_2$ | (CH$_2$)$_3$ | p-(2-CF$_3$)Ph | N | CH | 1 | NHCH$_3$ |

-continued

| | | | | | | |
|---|---|---|---|---|---|---|
| 339 | m-Am | (CH$_2$)$_2$ | p-(2-CF$_3$)Ph | N | CH 1 | OC$_2$H$_5$ |
| 340 | m-Am | (CH$_2$)$_3$ | p-(2-CF$_3$)Ph | N | CH 1 | OH |
| 341 | m-Am | (CH$_2$)$_2$ | p-(2-CF$_3$)Ph | N | CH 1 | OCH$_3$ |
| 342 | m-C=ONH$_2$ | (CH$_2$)$_3$ | p-(2-CF$_3$)Ph | N | CH 1 | OH |
| 343 | m-C=ONH$_2$ | (CH$_2$)$_2$ | p-(2-CF$_3$)Ph | N | CH 1 | OCH$_3$ |
| 344 | m-C=ONH$_2$ | (CH$_2$)$_3$ | p-(2-CF$_3$)Ph | N | CH 1 | NHCH$_3$ |
| 345 | m-Am | (CH$_2$)$_2$ | p-(2-SO$_2$NH$_2$)Ph | N | N 1 | OC$_2$H$_5$ |
| 346 | m-Am | (CH$_2$)$_3$ | p-(2-SO$_2$NH$_2$)Ph | N | N 1 | OH |
| 347 | m-Am | (CH$_2$)$_2$ | p-(2-SO$_2$NH$_2$)Ph | N | N 1 | OCH$_3$ |
| 348 | m-C=ONH$_2$ | (CH$_2$)$_3$ | p-(2-SO$_2$NH$_2$)Ph | N | N 1 | OH |
| 349 | m-C=ONH$_2$ | (CH$_2$)$_2$ | p-(2-SO$_2$NH$_2$)Ph | N | N 1 | OCH$_3$ |
| 350 | m-C=ONH$_2$ | (CH$_2$)$_3$ | p-(2-SO$_2$NH$_2$)Ph | N | N 1 | NHCH$_3$ |
| 351 | m-Am | (CH$_2$)$_2$ | p-(2-SO$_2$CH$_3$)Ph | N | N 1 | OC$_2$H$_5$ |
| 352 | m-Am | (CH$_2$)$_3$ | p-(2-SO$_2$CH$_3$)Ph | N | N 1 | OH |
| 353 | m-Am | (CH$_2$)$_2$ | p-(2-SO$_2$CH$_3$)Ph | N | N 1 | OCH$_3$ |
| 354 | m-C=ONH$_2$ | (CH$_2$)$_3$ | p-(2-SO$_2$CH$_3$)Ph | N | N 1 | OH |
| 355 | m-C=ONH$_2$ | (CH$_2$)$_2$ | p-(2-SO$_2$CH$_3$)Ph | N | N 1 | OCH$_3$ |
| 356 | m-C=ONH$_2$ | (CH$_2$)$_3$ | p-(2-SO$_2$CH$_3$)Ph | N | N 1 | NHCH$_3$ |
| 357 | m-Am | (CH$_2$)$_2$ | p-(2-SO$_2$CF$_3$)Ph | N | N 1 | OC$_2$H$_5$ |
| 358 | m-Am | (CH$_2$)$_3$ | p-(2-SO$_2$CF$_3$)Ph | N | N 1 | OH |
| 359 | m-Am | (CH$_2$)$_2$ | p-(2-SO$_2$CF$_3$)Ph | N | N 1 | OCH$_3$ |
| 360 | m-C=ONH$_2$ | (CH$_2$)$_3$ | p-(2-SO$_2$CF$_3$)Ph | N | N 1 | OH |
| 361 | m-C=ONH$_2$ | (CH$_2$)$_2$ | p-(2-SO$_2$CF$_3$)Ph | N | N 1 | OCH$_3$ |
| 362 | m-C=ONH$_2$ | (CH$_2$)$_3$ | p-(2-CF$_3$)Ph | N | N 1 | NHCH$_3$ |
| 363 | m-Am | (CH$_2$)$_2$ | p-(2-CF$_3$)Ph | N | N 1 | OC$_2$H$_5$ |
| 364 | m-Am | (CH$_2$)$_3$ | p-(2-CF$_3$)Ph | N | N 1 | OH |
| 365 | m-Am | (CH$_2$)$_2$ | p-(2-CF$_3$)Ph | N | N 1 | OCH$_3$ |
| 366 | m-C=ONH$_2$ | (CH$_2$)$_3$ | p-(2-CF$_3$)Ph | N | N 1 | OH |
| 367 | m-C=ONH$_2$ | (CH$_2$)$_2$ | p-(2-CF$_3$)Ph | N | N 1 | OCH$_3$ |
| 368 | m-C=ONH$_2$ | (CH$_2$)$_3$ | p-(2-CF$_3$)Ph | N | N 1 | NHCH$_3$ |
| 369 | m-Am | (CH$_2$)$_2$ | p-(2-SO$_2$NH$_2$)Ph | CF | CH 1 | OC$_2$H$_5$ |
| 370 | m-Am | (CH$_2$)$_3$ | p-(2-SO$_2$NH$_2$)Ph | CF | CH 1 | OH |
| 371 | m-Am | (CH$_2$)$_2$ | p-(2-SO$_2$NH$_2$)Ph | CF | CH 1 | OCH$_3$ |
| 372 | m-C=ONH$_2$ | (CH$_2$)$_3$ | p-(2-SO$_2$NH$_2$)Ph | CF | CH 1 | OH |
| 373 | m-C=ONH$_2$ | (CH$_2$)$_2$ | p-(2-SO$_2$NH$_2$)Ph | CF | CH 1 | OCH$_3$ |
| 374 | m-C=ONH$_2$ | (CH$_2$)$_3$ | p-(2-SO$_2$NH$_2$)Ph | CF | CH 1 | NHCH$_3$ |
| 375 | m-Am | (CH$_2$)$_2$ | p-(2-SO$_2$CH$_3$)Ph | CF | CH 1 | OC$_2$H$_5$ |
| 376 | m-Am | (CH$_2$)$_3$ | p-(2-SO$_2$CH$_3$)Ph | CF | CH 1 | OH |
| 377 | m-Am | (CH$_2$)$_2$ | p-(2-SO$_2$CH$_3$)Ph | CF | CH 1 | OCH$_3$ |
| 378 | m-C=ONH$_2$ | (CH$_2$)$_3$ | p-(2-SO$_2$CH$_3$)Ph | CF | CH 1 | OH |
| 379 | m-C=ONH$_2$ | (CH$_2$)$_2$ | p-(2-SO$_2$CH$_3$)Ph | CF | CH 1 | OCH$_3$ |
| 380 | m-C=ONH$_2$ | (CH$_2$)$_3$ | p-(2-SO$_2$CH$_3$)Ph | CF | CH 1 | NHCH$_3$ |
| 381 | m-Am | (CH$_2$)$_2$ | p-(2-SO$_2$CF$_3$)Ph | CF | CH 1 | OC$_2$H$_5$ |
| 382 | m-Am | (CH$_2$)$_3$ | p-(2-SO$_2$CF$_3$)Ph | CF | CH 1 | OH |
| 383 | m-Am | (CH$_2$)$_2$ | p-(2-SO$_2$CF$_3$)Ph | CF | CH 1 | OCH$_3$ |
| 384 | m-C=ONH$_2$ | (CH$_2$)$_3$ | p-(2-SO$_2$CF$_3$)Ph | CF | CH 1 | OH |
| 385 | m-C=ONH$_2$ | (CH$_2$)$_2$ | p-(2-SO$_2$CF$_3$)Ph | CF | CH 1 | OCH$_3$ |
| 386 | m-C=ONH$_2$ | (CH$_2$)$_3$ | p-(2-CF$_3$)Ph | CF | CH 1 | NHCH$_3$ |
| 387 | m-Am | (CH$_2$)$_2$ | p-(2-CF$_3$)Ph | CF | CH 1 | OC$_2$H$_5$ |
| 388 | m-Am | (CH$_2$)$_3$ | p-(2-CF$_3$)Ph | CF | CH 1 | OH |
| 389 | m-Am | (CH$_2$)$_2$ | p-(2-CF$_3$)Ph | CF | CH 1 | OCH$_3$ |
| 390 | m-C=ONH$_2$ | (CH$_2$)$_3$ | p-(2-CF$_3$)Ph | CF | CH 1 | OH |
| 391 | m-C=ONH$_2$ | (CH$_2$)$_2$ | p-(2-CF$_3$)Ph | CF | CH 1 | OCH$_3$ |
| 392 | m-C=ONH$_2$ | (CH$_2$)$_3$ | p-(2-CF$_3$)Ph | CF | CH 1 | NHCH$_3$ |

TABLE 4

| Ex | D | Z | B | p | R |
|---|---|---|---|---|---|
| 401 | m-Am | (CH$_2$)$_4$ | p-Guan | 1 | OC$_2$H$_5$ |
| 402 | m-Am | (CH$_2$)$_4$ | p-NH$_2$ | 1 | OC$_2$H$_5$ |
| 403 | m-Am | (CH$_2$)$_4$ | p-Guan | 1 | OH |
| 404 | m-Am | (CH$_2$)$_2$ | p-Guan | 1 | OCH$_3$ |
| 405 | m-Am | (CH$_2$)$_2$ | p-NH$_2$ | 1 | OCH$_3$ |
| 406 | m-Am | (CH$_2$)$_2$ | p-Am | 1 | OCH$_3$ |

TABLE 4-continued

| Ex | D | Z | B | p | R |
|---|---|---|---|---|---|
| 407 | m-Am | (CH$_2$)$_2$ | p-Am | 1 | OH |
| 408 | m-Am | (CH$_2$)$_2$ | p-H | 1 | OCH$_3$ |
| 409 | m-Am | (CH$_2$)$_2$ | p-Guan | 2 | OCH$_3$ |
| 410 | m-Am | (CH$_2$)$_2$ | p-NH$_2$ | 2 | OCH$_3$ |
| 411 | m-Am | (CH$_2$)$_2$ | p-Am | 2 | OCH$_3$ |
| 412 | m-Am | (CH$_2$)$_4$ | p-NH$_2$ | 1 | OCH$_3$ |
| 413 | m-C=ONH$_2$ | (CH$_2$)$_3$ | p-NH$_2$ | 1 | OCH$_3$ |
| 414 | m-Am | (CH$_2$)$_3$ | p-(2-SO$_2$NH$_2$)Ph | 1 | OCH$_3$ |
| 415 | m-C=ONH$_2$ | (CH$_2$)$_3$ | p-(2-SO$_2$NH$_2$)Ph | 1 | OCH$_3$ |
| 416 | m-Am | (CH$_2$)$_2$ | p-(2-SO$_2$NH$_2$)Ph | 1 | OCH$_3$ |
| 417 | m-Am | (CH$_2$)$_3$ | p-(2-SO$_2$NH-t-Bu)Ph | 1 | OCH$_3$ |
| 418 | m-Am | (CH$_2$)$_2$ | p-(2-SO$_2$CH$_3$)Ph | 1 | OC$_2$H$_5$ |
| 419 | m-Am | (CH$_2$)$_2$ | p-(2-SO$_2$CF$_3$)Ph | 1 | OCH$_3$ |
| 420 | m-C=ONH$_2$ | (CH$_2$)$_2$ | p-(2-CF$_3$)Ph | 1 | OC$_2$H$_5$ |

Utility

The compounds of this invention are useful as anticoagulants for the treatment or prevention of thromboembolic disorders in mammals. The term "thromboembolic disorders" as used herein includes arterial or venous cardiovascular or cerebrovascular thromboembolic disorders, including, for example, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, cerebral embolism, kidney embolisms, and pulmonary embolisms.

The anticoagulant effect of compounds of the present invention is due to inhibition of factor Xa. The effectiveness of compounds of the present invention as inhibitors of factor Xa was determined using purified human factor Xa and synthetic substrate. The rate of factor Xa hydrolysis of chromogenic substrate S2222 (Kabi Pharmacia, Franklin, Ohio) was measured both in the absence and presence of compounds of the present invention. Hydrolysis of the substrate resulted in the release of pNA, which was monitored spectrophotometrically by measuring the increase in absorbance at 405 nM. A decrease in the rate of absorbance change at 405 nm in the presence of inhibitor is indicative of enzyme inhibition. The results of this assay are expressed as inhibitory constant, $K_i$.

Factor Xa determinations were made in 0.10 M sodium phosphate buffer, pH 7.5, containing 0.20 M NaCl, and 0.5% PEG 8000. The Michaelis constant, $K_m$, for substrate hydrolysis was determined at 25° C. using the method of Lineweaver and Burk. Values of $K_i$ were determined by allowing 0.2–0.5 nM human factor Xa (Enzyme Research Laboratories, South Bend, Ind.) to react with the substrate (0.20 mM–1 mM) in the presence of inhibitor. Reactions were allowed to go for 30 minutes and the velocities (rate of absorbance change vs time) were measured in the time frame of 25–30 minutes. The following relationship was used to calculate $K_i$ values:

$$(v_o - v_s)/v_s = I/(K_i (1 + S/K_m))$$

where:
- $v_o$ is the velocity of the control in the absence of inhibitor;
- $v_s$ is the velocity in the presence of inhibitor;
- I is the concentration of inhibitor;
- $K_i$ is the dissociation constant of the enzyme:inhibitor complex;
- S is the concentration of substrate;
- $K_m$ is the Michaelis constant.

Using the methodology described above, a number of compounds of the present invention were found to exhibit a $K_i$ of $\leq 1$ μm, thereby confirming the utility of the compounds of the present invention as effective thrombin inhibitors.

The antithrombotic effect of the compounds of the present invention can be demonstrated in a rat vena cava thrombosis model. In this model Male Sprague-Dawley rats weighing 350–450 grams anesthetized with a mixture of xylazine (10 mg/kg i.m.) and ketamine (110 mg/kg i.m.) are used. A carotid artery, a jugular vein and a femoral vein are cannulated for blood sampling, drug infusion and hypotonic saline injection, respectively. The abdominal vena cava is isolated and all its side-branches are ligated beneath the left renal vein. Thrombus formation is induced by rapid injection of 1 mL hypotonic saline (0.225%) into the vena cava. This is followed 15 seconds later by a 15-minute stasis of an isolated segment (about 1 cm) of the vena cava. The formed thrombus in the vena cava is removed and immediately weighed.

Test compounds or vehicle are given as continuous intravenous infusions or orally starting 1 hour before the injection of hypotonic saline. Arterial blood samples (1.5 mL) for the determination of clotting times are collected before and 1 hour after the infusion or oral dosing of test compounds or vehicle. The percentage inhibition of thrombus formation is determined for each treatment group. The ID50 values (dose which produces 50% inhibition of thrombus formation) are estimated by linear regression.

The compounds of formula (I) are also considered to be useful as inhibitors of serine proteases, notably human thrombin, plasma kallikrein and plasmin. Because of their inhibitory action, these compounds are indicated for use in the prevention or treatment of physiological reactions, blood coagulation and inflammation, catalyzed by the aforesaid class of enzymes.

Compounds of the present invention were shown to be direct acting inhibitors of the serine protease thrombin by their ability to inhibit the cleavage of small molecule substrates by thrombin in a purified system. In vitro inhibition constants were determined by the method described by Kettner et al. in *J. Biol. Chem.* 265, 18289–18297 (1990), herein incorporated by reference. In these assays, thrombin-mediated hydrolysis of the chromogenic substrate S2238 (Helena Laboratories, Beaumont, Tex.) was monitored spectrophotometrically. Addition of an inhibitor to the assay mixture results in decreased absorbance and is indicative of thrombin inhibition. Human thrombin (Enzyme Research Laboratories, Inc., South Bend, Ind.) at a concentration of 0.2 nM in 0.10 M sodium phosphate buffer, pH 7.5, 0.20 M NaCl, and 0.5% polyethylene glycol 6000, was incubated with various substrate concentrations ranging from 0.20 to 0.02 mM. After 25 to 30 minutes of incubation, thrombin activity was assayed by monitoring the rate of increase in absorbance at 405 nm which arises owing to substrate hydrolysis. Inhibition constants were derived from reciprocal plots of the reaction velocity as a function of substrate concentration using the standard method of Lineweaver and Burk. Using the methodology described above, some compounds of this invention were evaluated and found to exhibit a $K_i$ of less than 10 μm, thereby confirming the utility of the compounds of the invention as effective thrombin inhibitors.

The compounds of the present invention can be administered alone or in combination with one or more additional therapeutic agents. These include other anti-coagulant or coagulation inhibitory agents, anti-platelet or platelet inhibitory agents, thrombin inhibitors, or thrombolytic or fibrinolytic agents.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

By "administered in combination" or "combination therapy" it is meant that the compound of Formula I and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. Other anticoagulant agents (or coagulation inhibitory agents) that may be used in combination with the compounds of this invention include warfarin and heparin, as well as other factor Xa inhibitors such as those described in the publications identified above under Background of the Invention.

The term anti-platelet agents (or platelet inhibitory agents), as used herein, denotes agents that inhibit platelet function such as by inhibiting the aggregation, adhesion or granular secretion of platelets. Such agents include the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), and piroxicam are preferred. Other suitable anti-platelet agents include ticlopidine, including pharmaceutically acceptable salts or prodrugs thereof. Ticlopidine is also a preferred compound since it is known to be gentle on the gastro-intestinal tract in use. Still other suitable platelet inhibitory agents include thromboxane-A2-receptor antagonists and thromboxane-A2-synthetase inhibitors, as well as pharmaceutically acceptable salts or prodrugs thereof.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/ or serotonin) and/or fibrin formation are disrupted. Such inhibitors include boroarginine derivatives and boropeptides, hirudin and argatroban, including pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. Boropeptide thrombin inhibitors include compounds described in Kettner et al., U.S. Pat. No. 5,187,157 and European Patent Application Publication Number 293 881 A2, the disclosures of which are hereby incorporated herein by reference. Other suitable boroarginine derivatives and boropeptide thrombin inhibitors include those disclosed in PCT Application Publication Number 92/07869 and European Patent Application Publication Number 471 651 A2, the disclosures of which are hereby incorporated herein by reference.

The term thrombolytics (or fibrinolytic) agents (or thrombolytics or fibrinolytics), as used herein, denotes agents that lyse blood clots (thrombi). Such agents include tissue plasminogen activator, anistreplase, urokinase or streptokinase, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Administration of the compounds of Formula I of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

The compounds of the present invention are also useful as standard or reference compounds, for example as a quality standard or control, in tests or assays involving the inhibition of factor Xa. Such compounds may be provided in a commercial kit, for example, for use in pharmaceutical research involving factor Xa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor Xa. For example, the presence of factor Xa in an unknown sample could be determined by addition of chromogenic substrate S2222 to a series of solutions containing test sample and optionally one of the compounds of the present invention. If a production of pNA is observed in the solutions containing test sample, but no compound of the present invention, then one would conclude factor Xa was present.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences,* Mack Publishing Company, a standard reference text in this field.

Representative useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of Formula I are administered in combination with an anti-platelet agent, by way of general guidance, typically a daily dosage may be about 0.01 to 25 milligrams of the compound of Formula I and about 50 to 150 milligrams of the anti-platelet agent, preferably about 0.1 to 1 milligrams of the compound of Formula I and about 1 to 3 milligrams of antiplatelet agents, per kilogram of patient body weight.

Where the compounds of Formula I are adminstered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Obviously, numerous modifications and variations of the present invention are possible in light of the above teachings. It is therefore to be understood that within the scope of the appended claims, the invention may be practiced otherwise that as specifically described herein.

What is claimed as new and desired to be secured by Letter Patent of United States is:

1. A compound of formula I:

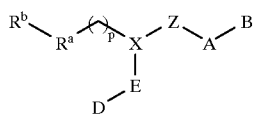

I or stereoisomers or pharmaceutically acceptable salt forms thereof, wherein:

D is selected from CN, $C(=NR^7)NR^8R^9$, $NHC(=NR^7)NR^8R^9$, $NR^8CH(=NR^7)$, $C(O)NR^8R^9$, and $(CH_2)_t NR^8R^9$, provided that D is substituted meta or para to X;

E is phenyl substituted with 1 $R^2$;

$R^a$ is a bond or CH=CH;

$R^b$ is C(O)R or G

G is selected from $OG^1$, $SG^1$, $NG^1G^2$, $OC(O)NG^2G^3$, $C_{3-10}$ carbocyclic residue substituted with 0–2 $R^4$, and a 5–10 membered heterocyclic system containing from 1–3 heteroatoms selected from the group consisting of N, O, and S substituted with 0–2 $R^4$;

$G^1$ is selected from H, $C_{1-6}$ alkyl, $C_{3-6}$ carbocyclic residue substituted with 0–2 $R^4$, and a 5–6 membered heterocyclic system containing from 1–3 heteroatoms selected from the group consisting of N, O, and S substituted with 0–2 $R^4$ provided that if $G^1$ is a heterocyclic system, then it is not attached to G through one of the heteroatoms of the heterocyclic system;

$G^2$ is selected from H and $C_{1-6}$ alkyl;

$G^3$ is selected from $C_{3-6}$ carbocyclic residue substituted with 0–2 $R^4$ and a 5–6 membered heterocyclic system containing from 1–3 heteroatoms selected from the group consisting of N, O, and S substituted with 0–2 $R^4$;

R is selected from H, OH, $C_{1-6}$ alkoxy, $C_{3-6}$ cycloalkoxy, $C_{6-10}$ aryloxy substituted with 0–2 $R^4$, $C_{1-6}$ alkyl substituted with 0–2 $R^5$, $NH_2$, $NR^1R^{1a}$, and $C_{3-6}$ carbocyclic residue substituted with 0–2 $R^4$;

$R^1$ and $R^{1a}$ are independently selected from H, $C_{1-6}$ alkoxy, $C_{1-6}$ alkyl substituted with 0–2 $R^5$, and $C_{3-10}$ carbocyclic residue substituted with 0–2 $R^4$;

$R^1$ and $R^{1a}$ together can be $C_{3-5}$ alkylene substituted with 0–2 $R^3$;

$R^2$ is selected from H, $OR^1$, halo, $C_{1-6}$ alkyl, $NR^1R^{1a}$, $C(=O)R^6$, and $SO_2NR^1R^{1a}$;

$R^3$ is selected from CN, $NO_2$, $C_{1-6}$ alkoxy, OH, $C_{1-6}$ alkyl, phenyl and halo;

$R^4$ is selected from H, OH, $C_{1-6}$ alkoxy, halo, $C_{1-6}$ alkyl, $C_{1-2}$ haloalkyl, CN, $NO_2$, $NR^6R^{6a}$, $(CH_2)_nNR^6R^{6a}$, $SO_2$—$C_{1-6}$ alkyl, $C(=O)R^6$, $SO_2$—$C_{6-10}$ aryl, $N(R^6)SO_2$—$C_{1-6}$ alkyl, and $SO_2NR^6R^{6a}$;

$R^5$ is selected from H, OH, $C_{1-6}$ alkoxy, phenyl, halo, $C_{1-6}$ alkyl, $C_{1-2}$ haloalkyl, CN, $NO_2$, $NR^6R^{6a}$, $(CH_2)_n NR^6R^{6a}$, $C(=O)R^6$, and $SO_2NR^6R^{6a}$;

$R^6$ and $R^{6a}$ are independently selected from H, $C_{1-6}$ alkyl, OH, $C_{1-6}$ alkoxy, $C_{3-6}$ cycloalkoxy, $C_{6-10}$ aryloxy;

$R^6$ and $R^{6a}$ together can be $C_{3-5}$ alkylene substituted with 0–2 $R^3$;

$R^7$ is selected from H, OH, $C_{1-6}$ alkyl, $C_{1-6}$ alkylcarbonyl, $C_{1-6}$ alkoxy, $C_{1-4}$ alkoxycarbonyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^8$ is selected from H, $C_{1-6}$ alkyl and $(CH_2)_n$-phenyl;

$R^9$ is selected from H, $C_{1-6}$ alkyl and $(CH_2)_n$-phenyl;

X is selected from $CR^1$ and N;

Z is $(CH_2)_n$;

n is 1, 2, 3 or 4;

p is 1, 2, 3, or 4;

q is 0, 1, or 2;

t is selected from 0 and 1;

A is selected from:
phenyl substituted with 0–2 $R^4$; and,
pyridyl substituted with 0–2 $R^4$; and, B is selected from H, $NR^1R^4$, $C(O)R^6$, $C(O)NR^6R^{6a}$, $C_{1-6}$ alkyl, $C(=NR^1)NR^1R^{1a}$, $NR^1C(=NR^1)NR^1R^{1a}$, and $B^1$–$B^2$;

$B^1$ is selected from $C_{1-4}$ alkylene, —C(O)—, —C(O)$CR^{10}R^{10a}$—, —$CR^{10}R^{10a}C(O)$, —$S(O)_q$—, —$S(O)_qCR^{10}R^{10a}$—, —$CR^{10}R^{10a}S(O)_q$—, —$C(O)NR^{10}$—, —$NR^{10}C(O)$—, —$C(O)NR^{10}CR^{10}R^{10a}$—, —$NR^{10}C(O)CR^{10}R^{10a}$—, —$CR^{10}R^{10a}C(O)NR^{10}$—, and —$CR^{10}R^{10a}NR^{10}C(O)$—;

$B^2$ is selected from:
$C_{3-10}$ carbocyclic residue substituted with 0–2 $R^4$, and 5–6 membered heterocyclic system containing from 1–4 heteroatoms selected from the group consisting of N, O, and S substituted with 0–2 $R^4$;

$R^{10}$ is selected from H, $CF_3$, $C_{1-6}$ alkyl, $C_{3-6}$ carbocyclic residue substituted with 0–2 $R^4$, and 5–6 membered heterocyclic system containing from 1–4 heteroatoms selected from the group consisting of N, O, and S substituted with 0–2 $R^4$;

$R^{10a}$ is selected from H, $CF_3$, $C_{1-6}$ alkyl, $C_{3-6}$ carbocyclic residue substituted with 0–2 $R^4$, and 5–6 membered heterocyclic system containing from 1–4 heteroatoms selected from the group consisting of N, O, and S substituted with 0–2 $R^4$;

provided that when: when BG is hydrogen A is substituted with $R^4$ and $R^4$ is other than hydrogen.

2. A compound according to claim 1, wherein:

G is selected from $OG^1$, $SG^1$, $NG^1G^2$, $OC(O)NG^2G^3$, $C_{5-6}$ carbocyclic residue substituted with 0–2 $R^4$, and a 5–6 membered heterocyclic system containing from 1–3 heteroatoms selected from the group consisting of N, O, and S substituted with 0–2 $R^4$;

$G^1$ is selected from H, $C_{1-6}$ alkyl, $C_{5-6}$ carbocyclic residue substituted with 0–2 $R^4$, and a 5–6 membered heterocyclic system containing from 1–3 heteroatoms selected from the group consisting of N, O, and S substituted with 0–2 $R^4$ provided that if $G^1$ is a heterocyclic system, then it is not attached to G through one of the heteroatoms of the heterocyclic system;

$G^3$ is selected from $C_{5-6}$ carbocyclic residue substituted with 0–2 $R^4$ and a 5–6 membered heterocyclic system containing from 1–3 heteroatoms selected from the group consisting of N, O, and S substituted with 0–2 $R^4$;

B is selected from $B^2$, $B^1$–$B^2$, $NR^1R^4$, $C(O)R^6$, $C(O)NR^6R^{6a}$, $C_{1-6}$ alkyl, $C(=NR^1)NR^1R^{1a}$, and $NR^1C(=NR^1)NR^1R^{1a}$;

$B^1$ is selected from $C_{1-4}$ alkylene, —C(O)—, —C(O)$CR^{10}R^{10a}$—, —$CR^{10}R^{10a}$C(O), —S(O)$_q$—, —S(O)$_q$ $CR^{10}R^{10a}$—, —$CR^{10}R^{10a}$S(O)$_q$—, —C(O)$NR^{10}$—, and —$NR^{10}$C(O)—;

$B^2$ is selected from one of the following carbocyclic and heterocyclic systems which are substituted with 0–2 $R^{4a}$;
phenyl, piperidinyl, piperazinyl, pyridyl, pyrimidyl, furanyl, thiophenyl, pyrrolyl, oxazolyl, isoxazolyl, thiazolyl, isothiazolyl, pyrazolyl, imidazolyl, oxadiazole, thiadiazole, triazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2,3-triazole, 1,2,4-triazole, 1,2,5-triazole, and 1,3,4-triazole.

3. A compound according to claim 2, wherein the compound is of formula II:

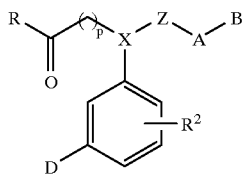

II wherein:
R is selected from OH, $C_{1-6}$ alkoxy, $C_{3-6}$ cycloalkoxy, $C_{6-10}$ aryloxy substituted with 0–2 $R^4$, $C_{1-6}$ alkyl substituted with 0–2 $R^5$, and $NR^1R^{1a}$;

$R^2$ is selected from H, $OR^1$, halo, and $C_{1-6}$ alkyl;

$R^3$ is selected from $C_{1-6}$ alkoxy, $C_{1-6}$ alkyl, and halo;

$R^5$ is selected from H, OH, $C_{1-6}$ alkoxy, phenyl, halo, CN, $NO_2$, $NR^6R^{6a}$, and $C(=O)R^6$.

4. A compound according to claim 3, wherein:
D is $C(=NH)NH_2$ or $CH_2NR^8R^9$;

R is selected from OH, $C_{1-3}$ alkoxy, $C_{1-3}$ alkyl, $NH_2$, and $NHR^1$;

$R^1$ is $C_{1-3}$ alkyl substituted with 0–2 $R^5$;

$R^5$ is selected from OH, $C_{1-3}$ alkoxy, phenyl, CN, and $NH_2$;

p is 1, 2, or 3;

B is selected from $B^2$ and $B^1$–$B^2$;

$B^1$ is selected from $C_{1-4}$ alkylene, —C(O)—, —C(O)$CR^{10}R^{10a}$—, —$CR^{10}R^{10a}$C(O), —C(O)$NR^{10}$—, and —$NR^{10}$C(O)—; and, $B^2$ is selected from one of the following carbocyclic and heterocyclic systems which are substituted with 0–2 $R^{4a}$;
phenyl, piperidinyl, piperazinyl, pyridyl, pyrimidyl, furanyl, thiophenyl, pyrrolyl, oxazolyl, isoxazolyl, thiazolyl, isothiazolyl, pyrazolyl, imidazolyl, oxadiazole, thiadiazole, triazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2,3-triazole, 1,2,4-triazole, 1,2,5-triazole, and 1,3,4-triazole.

5. A compound according to claim 4, wherein:
$R^6$ and $R^{6a}$ are independently selected from H, $C_{1-3}$ alkyl, $C_{1-3}$ alkoxy, $C_{3-6}$ cycloalkoxy, phenoxy;

X is selected from CH and N;

p is 1;

A is phenyl substituted with 0–1 $R^4$; and,

B is selected from $NH_2$, $C(=NH)NH_2$, $NHC(=NH)NH_2$, and phenyl substituted with 0–1 $R^4$.

6. A compound according to claim 1, wherein the compound is selected from the group:
methyl 4-(aminoiminomethyl)-beta-[3-(aminoiminomethyl)phenyl]benzene pentanoate;
ethyl 4-(aminoiminomethyl)-beta-[3-(aminoiminomethyl)phenyl]benzene pentanoate;
methyl 4-[(aminoiminomethyl)amino]-beta-[3-(aminoiminomethyl)phenyl]benzenepentanoate;
methyl 4-[(aminoiminomethyl)amino]-beta-[3-(aminoiminomethyl)phenyl]benzeneheptanoate;
ethyl 3-(aminoiminomethyl)-beta-[[4-(aminoiminomethyl)phenyl]methoxy]benzenepropanoate;
N-[4-[4-[(aminoiminomethyl)amino]phenyl]butyl]-N-[3-(aminoiminomethyl)phenyl]glycine;
ethyl N-[3-(aminoiminomethyl)phenyl]-N-[4-(4-aminophenyl)butyl]glycine;
ethyl N-[4-[4-[(aminoiminomethyl)amino]phenyl]butyl]-N-[3-(aminoiminomethyl)phenyl]glycine;
methyl N-[3-(aminoiminomethyl)phenyl]-N-[3-[2'-(aminosulfonyl)[1,1'-biphenyl]-4-yl]propyl]glycine;
methyl N-[3-(aminoiminomethyl)phenyl]-N-[3-[2'-[[(1,1-dimethylethyl)amino]sulfonyl][1,1'-biphenyl]-4-yl]propyl]glycine;
methyl N-[3-(aminoiminomethyl)phenyl]-N-[2-[2'-(aminosulfonyl)[1,1'-biphenyl]-4-yl]ethyl]glycine; and,
methyl N-[3-(aminoiminomethyl)phenyl]-N-[2-[2'-[[(1,1-dimethylethyl)amino]sulfonyl][1,1'-biphenyl]-4-yl]ethyl]glycine; or,
stereoisomers or pharmaceutically acceptable salt forms thereof.

7. A pharmaceutical composition, comprising: a pharmaceutically acceptable carrier and a therapeutically effective amount of a compound of claim 1 or a pharmaceutically acceptable salt form thereof.

8. A pharmaceutical composition, comprising: a pharmaceutically acceptable carrier and a therapeutically effective amount of a compound of claim 2 or a pharmaceutically acceptable salt form thereof.

9. A pharmaceutical composition, comprising: a pharmaceutically acceptable carrier and a therapeutically effective amount of a compound of claim 3 or a pharmaceutically acceptable salt form thereof.

10. A pharmaceutical composition, comprising: a pharmaceutically acceptable carrier and a therapeutically effective amount of a compound of claim 4 or a pharmaceutically acceptable salt form thereof.

11. A pharmaceutical composition, comprising: a pharmaceutically acceptable carrier and a therapeutically effective amount of a compound of claim 5 or a pharmaceutically acceptable salt form thereof.

12. A pharmaceutical composition, comprising: a pharmaceutically acceptable carrier and a therapeutically effective amount of a compound of claim 6 or a pharmaceutically acceptable salt form thereof.

13. A method for treating or preventing a thromboembolic disorder, comprising: administering to a patient in need thereof a therapeutically effective amount of a compound of claim 1 or a pharmaceutically acceptable salt form thereof.

14. A method for treating or preventing a thromboembolic disorder, comprising: administering to a patient in need thereof a therapeutically effective amount of a compound of claim 2 or a pharmaceutically acceptable salt form thereof.

15. A method for treating or preventing a thromboembolic disorder, comprising: administering to a patient in need thereof a therapeutically effective amount of a compound of claim 3 or a pharmaceutically acceptable salt form thereof.

16. A method for treating or preventing a thromboembolic disorder, comprising: administering to a patient in need thereof a therapeutically effective amount of a compound of claim 4 or a pharmaceutically acceptable salt form thereof.

17. A method for treating or preventing a thromboembolic disorder, comprising: administering to a patient in need thereof a therapeutically effective amount of a compound of claim 5 or a pharmaceutically acceptable salt form thereof.

18. A method for treating or preventing a thromboembolic disorder, comprising: administering to a patient in need thereof a therapeutically effective amount of a compound of claim 6 or a pharmaceutically acceptable salt form thereof.

* * * * *